(12) United States Patent
Goutopoulos et al.

(10) Patent No.: US 8,076,486 B2
(45) Date of Patent: *Dec. 13, 2011

(54) HETEROARYL-SUBSTITUTED ARYLAMINOPYRIDINE DERIVATIVES AS MEK INHIBITORS

(75) Inventors: Andreas Goutopoulos, Boston, MA (US); Benny C. Askew, Jr., Marshfield, MA (US); Xiaoling Chen, Newton, MA (US); Srinivasa Karra, Pembroke, MA (US); Henry Yu, Wellesley, MA (US)

(73) Assignee: Merck Serono S.A., Coinsins, Vaud (CH)

( * ) Notice: Subject to any disclaimer, the term of this patent is extended or adjusted under 35 U.S.C. 154(b) by 324 days.

This patent is subject to a terminal disclaimer.

(21) Appl. No.: 11/788,032

(22) Filed: Apr. 18, 2007

(65) Prior Publication Data

US 2007/0287737 A1    Dec. 13, 2007

Related U.S. Application Data

(60) Provisional application No. 60/793,073, filed on Apr. 19, 2006.

(51) Int. Cl.
C07D 417/00 (2006.01)
C07D 413/04 (2006.01)
C07D 401/00 (2006.01)

(52) U.S. Cl. ............... 546/268.7; 546/269.7; 546/275.4

(58) Field of Classification Search ............... 546/268.7, 546/269.4, 275.4
See application file for complete search history.

(56) References Cited

FOREIGN PATENT DOCUMENTS

| WO | WO 00/42029 | | 7/2000 |
|---|---|---|---|
| WO | WO 00/42029 A1 | | 7/2000 |
| WO | WO 02/072571 A2 | | 9/2002 |
| WO | WO 2004/024711 A1 | | 3/2004 |
| WO | WO 2004/052280 A2 | | 6/2004 |
| WO | WO 2004/056789 | | 7/2004 |
| WO | WO 2004/056789 A1 | | 7/2004 |
| WO | WO 2004091480 | * | 10/2004 |
| WO | WO 2005/000818 | | 1/2005 |
| WO | WO 2005/004818 A2 | | 1/2005 |
| WO | WO 2005/051301 | | 6/2005 |
| WO | WO 2006045514 | * | 4/2006 |
| WO | WO 2006/045514 A1 | | 5/2006 |

OTHER PUBLICATIONS

Chang, et al., "Signal Transduction Mediated by the Ras/Raf/MEK/ERK pathway from Cytokine Receptors to Transcription Factors: Potential Targeting for Therapeutic Intervention," *MTT Leukemia*, 17:1263-1293 (2003).

Crews, et al., "The Primary Structure of MEK, a Protein Kinase That Phosphorylates the ERK Gene Product," *Science*, 258:478-480 (1992).

Lee, et al., "Regulation of Hepatocyte Growth Factor-Mediated Urokinase Plasminogen Activator Secretion by MEK/ERK Activation in Human Stomach Cancer Cell Lines," *Experimental and Molecular Medicine*, 38:27-35 (2006).

Reddy, el al., "Role of MAP Kinase in Tumor Progression and Invasion," *Cancer and Metastasis Reviews*, 22:395-403 (2003).

\* cited by examiner

*Primary Examiner* — Nizal Chandrakumar
(74) *Attorney, Agent, or Firm* — Thomas W. Brown; EMD Serono Research Institute

(57) ABSTRACT

The invention provides novel heteroaryl-substituted arylaminopyridine derivative MEK inhibitors of Formula (Ia)

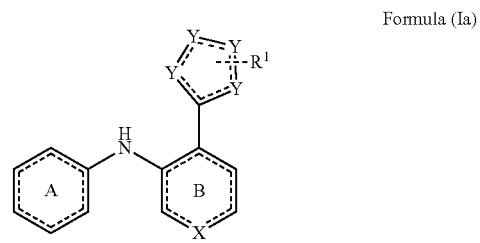

Formula (Ia)

Such compounds are MEK inhibitors that are useful in the treatment of hyperproliferative diseases, such as cancer and inflammation. Also disclosed is the treatment of a hyperproliferative disease in mammals, and pharmaceutical compositions containing such compounds.

21 Claims, No Drawings

HETEROARYL-SUBSTITUTED ARYLAMINOPYRIDINE DERIVATIVES AS MEK INHIBITORS

RELATED APPLICATION

This application claims the benefit of U.S. Provisional Application No. 60/793,073, filed on Apr. 19, 2006. The entire teachings of the above application are incorporated herein by reference.

FIELD OF THE INVENTION

The invention relates to novel heteroaryl-substituted arylaminopyridine derivative MEK inhibitors, which are useful in the treatment of hyperproliferative diseases, such as cancer and inflammation, in mammals. The invention also relates to a method of treating a mammal suffering from or susceptible to a hyperproliferative disease, such as cancer and inflammation, comprising administering a therapeutically effective amount of a heteroaryl-substituted arylaminopyridine derivative according to the invention. Furthermore, the invention relates to pharmaceutical compositions containing such MEK inhibitors.

BACKGROUND OF THE INVENTION

The Ras/Raf/MEK/MAPK cascade is one of the major pathways transmitting signals from the cell surface to the nucleus. The Ras family of G-proteins relay signals from activated growth factor receptors to the downstream intracellular Raf family kinases, which, in turn, trigger the activation of MEK1 and MEK2 extracellular signal-regulated kinase (ERK1/ERK2) pathway. The MEK family of genes consists of five genes: MEK1, MEK2, MEK3, MEK4 and MEK5. The structure of MEK consists of an amino-terminal negative regulatory domain and a carboxy-terminal MAP kinase-binding domain, which is necessary for binding and activation of ERKs. MEK1 is a 393-amino-acid protein with a molecular weight of 44 kDa (Crews et al., Science 1992, 258, 478-80).

Upstream and downstream signalling of the Ras/Raf/MEK/MAPK cascade involves multiple pathways, however MEK appears to specifically phosphorylate MAPK. The role of MAPK in cancer (Reddy et al. Cancer Metastasis Rev. 2004, 22, 395-403), and the dysfunctional activation of signalling components in the MAPK pathway in a high proportion of tumor types, has lead to an extended interest in MEK as a cancer target and the development of MEK inhibitors (Chang et al., Leukemia 2003, 17,1263-93; Lee et al., Exp. Mol. Med. 2006, 38, 27-35)

Among the furthest advanced MEK inhibitors is Pfizer's PD-0325901, a diarylamine derived MEK inhibitor, that has entered phase II clinical trials for the potential oral treatment of cancer.

Array Biopharma's ARRY142886, a phenylamino-2-pyridone derived MEK inhibitor, is currently in Phase I clinical trials.

WO 00/42029 (Warner-Lambert Company) further reports about diarylamines (A) that exhibit MEK inhibitory activity and are potentially useful for the treatment of cancer and other proliferative diseases.

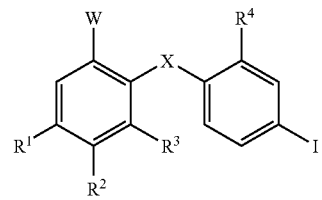

(A)

WO 04/056789 (Warner-Lambert Company) reports about oxadiazole- and thiadiazole-phenylamine derivatives (B) as MEK inhibitors for the potential treatment of inflammation and proliferative diseases.

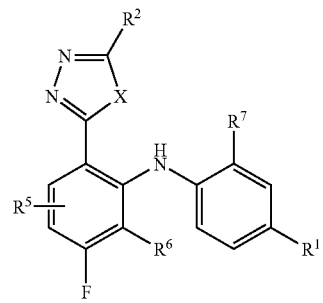

(B)

WO 05/051301 (Array Biopharma Inc.) relates to heterocyclic compounds, which are MEK inhibitors and useful for the potential treatment of hyperproliferative diseases.

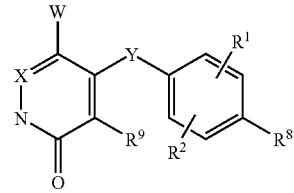

(C)

WO 05/000818 (Warner-Lambert Company) relates to phenylamino-2-pyridone derivatives as MEK inhibitors that might be useful for the treatment of proliferative diseases.

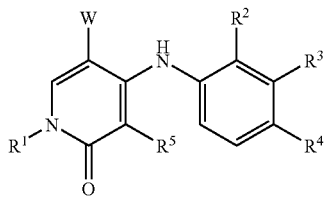

(D)

SUMMARY OF THE INVENTION

The invention provides in one aspect MEK inhibitors according to Formula (Ia). These compounds are suitable for the treatment of hyperproliferative diseases such as cancer and inflammation.

It is another aspect of the present invention to provide MEK inhibitors according to Formula (Ia), which are able to downregulate, especially inhibit the activity or function of MEK, especially in mammals.

It is another aspect of the present invention to provide a method for treating a mammal suffering from or susceptible to a hyperproliferative disease, comprising administering to the mammal a therapeutically effective amount of a MEK inhibitor according to Formula (Ia). Said diseases include cancer and inflammation It is another aspect of the present invention to provide a MEK inhibitor according to Formula (Ia) for use as a medicament.

It is another aspect of the present invention to provide a MEK inhibitor according to Formula (Ia) for the preparation of a medicament for the treatment of a hyperproliferative disease.

It is furthermore an aspect of the present invention to provide a pharmaceutical formulation, which comprises a MEK inhibitor according to Formula (Ia) and a pharmaceutically acceptable carrier.

It is finally another aspect of the present invention to provide a process for making compounds according to Formula (Ia).

MEK inhibitors of the invention have the following general formula:

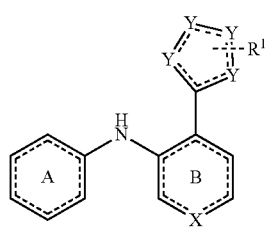

Formula (Ia)

wherein rings A and B, X, Y and $R^1$ are as defined in the detailed description.

DETAILED DESCRIPTION OF THE INVENTION

In view of the foregoing it is one aspect of the present invention to provide novel compounds according to Formula (Ia) that are useful in the treatment of hyperproliferative diseases. Specifically, hyperproliferative diseases related to the hyperactivity of MEK as well as diseases associated to MEK, such as cancer and inflammation, in mammals.

As a result, this invention provides in a first aspect novel compounds as well as pharmaceutically acceptable salts and pharmaceutically active derivatives thereof, that are useful for the treatment of hyperproliferative diseases, such as cancer and inflammation.

The compounds are defined by Formula (Ia):

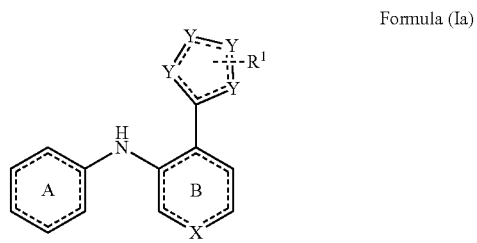

Formula (Ia)

as well as tautomers, pharmaceutically acceptable salts and pharmaceutically active derivatives thereof,
wherein:
rings A and B are optionally and independently substituted at any one or more substitutable ring carbon atoms with halogen, trimethylsilyl, cyano, $C_1$-$C_6$ alkyl, $C_1$-$C_6$ haloalkyl, $C_2$-$C_6$ alkenyl, $C_2$-$C_6$ alkynyl, $C_1$-$C_6$ alkoxy, $C_1$-$C_6$ haloalkoxy, or phenyl wherein the phenyl is optionally substituted at any one or more substitutable ring carbon atoms with halogen, trimethylsilyl, cyano, $C_1$-$C_6$ alkyl, $C_1$-$C_6$ haloalkyl, $C_2$-$C_6$ alkenyl, $C_2$-$C_6$ alkynyl, or $C_1$-$C_6$ alkoxy, $C_1$-$C_6$ haloalkoxy;

X is N or N→O;

Y is independently selected from NR', CR', S or O, whereby at least one Y is NR';

$R^1$ is selected from hydrogen, trimethylsilyl, $C_1$-$C_6$-alkyl, $OR^6$, $C(O)OR^6$, $NR^7R^8$, $SR^6$ $NR^7S(O)(O)R'$, $NR^7C(O)R^6$, $NR^7C(O)NR^7R^6$, $NR^7C(O)OR^6$, $NR^7C(O)C(O)OR^6$, $C_1$-$C_4$-alkyl-NR'R", $C_1$-$C_4$-alkyl-heterocycloalkyl or $C_1$-$C_4$ alkyl-$(OR')_n$;

$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR', $C_1$-$C_4$-alkyl-NR'R", $C_1$-$C_4$-alkyl-heterocycloalkyl, $C_1$-$C_4$ alkyl-$(OR')_n$ or $C_1$-$C_4$ alkyl-C(O)NR'R", wherein said alkyl, cycloalkyl, aryl, heteroaryl heterocycloalkyl, and alkyl-heterocycloalkyl is substituted or unsubstituted; or $R^7$ and $R^8$ can be taken together with the atom to which they are attached to form a 4 to 10-membered heteroaryl or heterocyclic ring, each of which is substituted or unsubstituted;

R' and R" are independently selected from hydrogen, $C_1$-$C_6$-alkyl or aryl, wherein said alkyl or aryl is substituted or unsubstituted; or R' and R" can be taken together with the atom to which they are attached to form a 4 to 10-membered heteroaryl or heterocyclic ring, each of which is substituted or unsubstituted; and n is 0 to 2.

In preferred embodiments, the variants have the following meanings:

$R^1$ is selected from $OR^6$, $NR^7R^8$, $NR^7C(O)R^6$ or $SR^6$;

rings A and B are optionally and independently substituted at any one or more substitutable ring carbon atoms with F, Cl, I, Br or phenyl; preferably F or I;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR', $C_1$-$C_4$ alkyl-$(OR')_n$, $C_1$-$C_4$-alkyl-NR'R", $C_1$-$C_4$ alkyl-C(O)NR'R" or $C_1$-$C_4$ alkyl-C(O)NR'R", wherein said alkyl is substituted or unsubstituted; or $R^7$ and $R^8$ can be taken together with the atom to which they are attached to form a 6-membered heterocyclic ring with 1 or 2 N atoms and optionally an O atom, which is substituted or unsubstituted; preferably said cyclic ring is morpholinyl, piperidinyl or piperazinyl;

R' and R" are independently either hydrogen or $C_1$-$C_6$-alkyl; or

R' and R" can be taken together with the atom to which they are attached to form a 6-membered heterocyclic ring with 1 or 2 N atoms and optionally an O atom, which is substituted or unsubstituted.

As set forth above, the variants of each of $R^1$, $R^6$, $R^7$, $R^8$, R' and R" are optionally substituted. In this case they are independently substituted with 1 to 5, preferably 1 to 3, more preferably 1 or 2 groups, independently selected from halogen, cyano, nitro, $CF_3$, $CHF_2$, $CH_2F$, $OCF_3$, $OCHF_2$, $OCH_2F$, $SCF_3$, $SCHF_2$, $SCH_2F$, azido, amino, aminosulfonyl, sulfonylamine, sulfanyl, sulfonyl, sulfinyl, sulfonyloxy, acyl, acyloxy, carboxy, alkoxy or hydroxyl, preferably halogen, cyano, nitro, alkoxy, hydroxyl, $CF_3$, $CHF_2$, $CH_2F$, $OCF_3$, $OCHF_2$, $OCH_2F$, $SCF_3$, $SCHF_2$, $SCH_2F$, azido, more preferably halogen, cyano, nitro, $CF_3$, $CHF_2$, $CH_2F$, $OCF_3$, $OCHF_2$, $OCH_2F$, $SCF_3$, $SCHF_2$, $SCH_2F$, OH, methoxy, $NH_2$ or $N(methyl)_2$.

In one embodiment, the invention provides compounds of Formula (I):

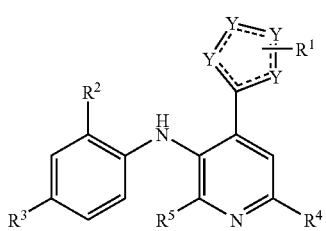

Formula (I)

as well as tautomers, pharmaceutically acceptable salts and pharmaceutically active derivatives thereof,
wherein:
Each Y is independently selected from NR', CR" or O, whereby at least one Y is NR';

$R^1$ is selected from hydrogen, $C_1$-$C_6$-alkyl, $OR^6$, $NR^7R^8$, $SR^6$ or $NR^7S(O)(O)R'$, $NR^7C(O)R^6$; $NR^7C(O)NR^7R^6$; $NR^7C(O)OR^6$;

$R^2$ is halogen;

$R^3$ is selected from Cl, F or I;

$R^4$ and $R^5$ are independently selected from hydrogen, halogen, $C_1$-$C_6$ alkyl or $C_1$-$C_6$ alkoxy, wherein said alkyl or alkoxy is substituted or unsubstituted;

$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR' or $C_1$-$C_4$ alkyl-C(O)NR'R", wherein said alkyl, cycloalkyl, aryl, heteroaryl and heterocyclyl is substituted or unsubstituted; or $R^7$ and $R^8$ can be taken together with the atom to which they are attached to form a 4 to 10-membered heteroaryl or heterocyclic ring, each of which is substituted or unsubstituted; and R' and R" are independently selected from hydrogen, $C_1$-$C_6$ alkyl or aryl, wherein said alkyl or aryl is substituted or unsubstituted.

In preferred embodiments, the variants have the following meanings:
$R^1$ is selected from $OR^6$, $NR^7R^8$ or $SR^6$;
$R^2$ is selected from F, Cl, I or Br; preferably $R^2$ is F;

$R^3$ is selected from F, Cl, I or $C_1$-$C_6$ alkyl, preferably $R^3$ is I;

$R^4$ and $R^5$ are independently either hydrogen or $C_1$-$C_6$ alkyl, preferably $R^4$ and $R^5$ are hydrogen;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR' or $C_1$-$C_4$ alkyl-C(O)NR'R", wherein said alkyl is substituted or unsubstituted; or $R^7$ and $R^8$ can be taken together with the atom to which they are attached to form a 6-membered heterocyclic ring with 1 or 2 N atoms and optionally an O atom, which is substituted or unsubstituted; preferably said cyclic ring is morpholinyl, piperidinyl or piperazinyl;

R' and R" are independently either hydrogen or $C_1$-$C_6$-alkyl.

As set forth above, the variants of each of $R^4$, $R^5$, $R^6$, $R^7$, $R^8$, R' and R" are optionally substituted. In this case they are independently substituted with 1 to 5, preferably 1 to 3, more preferably 1 or 2 groups, independently selected from halogen, cyano, nitro, $CF_3$, $CHF_2$, $CH_2F$, $OCF_3$, $OCHF_2$, $OCH_2F$, $SCF_3$, $SCHF_2$, $SCH_2F$, azido, amino, aminosulfonyl, sulfonylamine, sulfanyl, sulfonyl, sulfinyl, sulfonyloxy, acyl, acyloxy, carboxy, alkoxy or hydroxyl, preferably halogen, cyano, nitro, alkoxy, hydroxyl, $CF_3$, $CHF_2$, $CH_2F$, $OCF_3$, $OCHF_2$, $OCH_2F$, $SCF_3$, $SCHF_2$, $SCH_2F$, azido, more preferably halogen, cyano, nitro, $CF_3$, $CHF_2$, $CH_2F$, $OCF_3$, $OCHF_2$, $OCH_2F$, $SCF_3$, $SCHF_2$, $SCH_2F$, OH, methoxy, $NH_2$ or $N(methyl)_2$.

In one embodiment, the invention provides compounds of Formula (II):

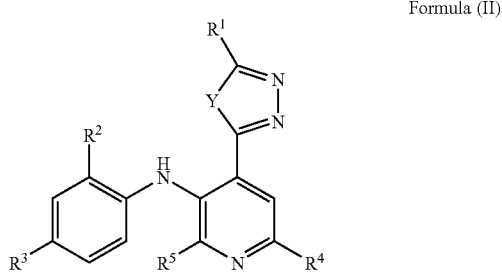

Formula (II)

or alternatively compounds of Formula (IIa) or Formula (IIb)

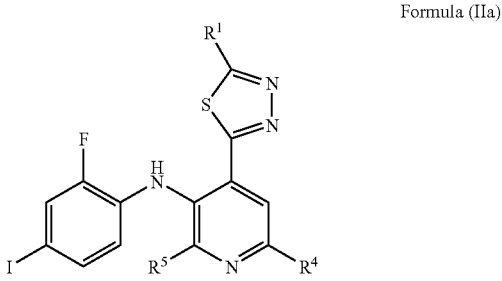

Formula (IIa)

-continued

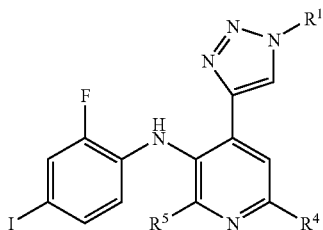

Formula (IIb)

as well as tautomers, pharmaceutically acceptable salts and pharmaceutically active derivatives thereof,
the variables in Formula (II), Formula (IIa) and Formula (IIb) are defined as follows:

Y in Formula (II) is either NR' or O;

$R^1$ is selected from hydrogen, trimethylsilyl, $C_1$-$C_6$-alkyl, $OR^6$, $C(O)OR^6$, $NR^7R^8$, $SR^6$, $NR^7S(O)(O)R'$, $NR^7C(O)R^6$, $NR^7C(O)NR^7R^6$, $NR^7C(O)OR^6$, $NR^7C(O)C(O)OR^6$, $C_1$-$C_4$-alkyl-NR'R", $C_1$-$C_4$-alkyl-heterocycloalkyl or $C_1$-$C_4$ alkyl-$(OR')_n$;

$R^2$ is selected from halogen, $C_1$-$C_6$-alkyl or $OR^6$;

$R^3$ is selected from halogen, trimethylsilyl, $C_1$-$C_6$-alkyl or $OR^6$;

$R^4$ and $R^5$ are independently selected from hydrogen, halogen, $C_1$-$C_6$ alkyl or $C_1$-$C_6$ alkoxy, wherein said alkyl or alkoxy is substituted or unsubstituted;

$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR', $C_1$-$C_4$-alkyl-NR'R", $C_1$-$C_4$-alkyl-heterocycloalkyl, $C_1$-$C_4$ alkyl-$(OR')_n$ or $C_1$-$C_4$ alkyl-C(O)NR'R", wherein said alkyl, cycloalkyl, aryl, heteroaryl, heterocycloalkyl, and alkyl-heterocycloalkyl is substituted or unsubstituted; or $R^7$ and $R^8$ can be taken together with the atom to which they are attached to form a 4 to 10-membered heteroaryl or heterocyclic ring, each of which is substituted or unsubstituted;

R' and R" are independently selected from hydrogen, $C_1$-$C_6$-alkyl or aryl, wherein said alkyl or aryl is substituted or unsubstituted; or R' and R" can be taken together with the atom to which they are attached to form a 4 to 10-membered heteroaryl or heterocyclic ring, each of which is substituted or unsubstituted; and n is 0 to 2.

In preferred embodiments, the variants in Formula (IIa) and Formula (IIb) have the following meanings:

$R^1$ is selected from $OR^6$, $NR^7R^8$ or $SR^6$;

$R^2$ is selected from F, Cl, I or Br; preferably $R^2$ is F;

$R^3$ is selected from F, Cl or I, preferably $R^3$ is I;

$R^4$ and $R^5$ are independently either hydrogen or $C_1$-$C_6$ alkyl, preferably $R^4$ and $R^5$ are hydrogen;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR' or $C_1$-$C_4$ alkyl-C(O)NR'R", wherein said alkyl is substituted or unsubstituted; or $R^7$ and $R^8$ can be taken together with the atom to which they are attached to form a 6-membered heterocyclic ring with 1 or 2 N atoms and optionally an O atom, which is substituted or unsubstituted; preferably said cyclic ring is morpholinyl, piperidinyl or piperazinyl;

R' and R" are independently either hydrogen or $C_1$-$C_6$-alkyl; or

R' and R" can be taken together with the atom to which they are attached to form a 6-membered heterocyclic ring with 1 or 2 N atoms and optionally an O atom, which is substituted or unsubstituted.

As set forth above, the variants of each of $R^4$, $R^5$, $R^6$, $R^7$, $R^8$, R' and R" are optionally substituted. In this case they are independently substituted with 1 to 5, preferably 1 to 3, more preferably 1 or 2 groups, independently selected from halogen, cyano, nitro, $CF_3$, $CHF_2$, $CH_2F$, $OCF_3$, $OCHF_2$, $OCH_2F$, $SCF_3$, $SCHF_2$, $SCH_2F$, azido, amino, aminosulfonyl, sulfonylamine, sulfanyl, sulfonyl, sulfinyl, sulfonyloxy, acyl, acyloxy, carboxy, alkoxy or hydroxyl, preferably halogen, cyano, nitro, alkoxy, hydroxyl, $CF_3$, $CHF_2$, $CH_2F$, $OCF_3$, $OCHF_2$, $OCH_2F$, $SCF_3$, $SCHF_2$, $SCH_2F$, azido, more preferably halogen, cyano, nitro, $CF_3$, $CHF_2$, $CH_2F$, $OCF_3$, $OCHF_2$, $OCH_2F$, $SCF_3$, $SCHF_2$, $SCH_2F$, OH, methoxy, $NH_2$ or $N(methyl)_2$.

In another embodiment, the invention provides compounds of Formula (III):

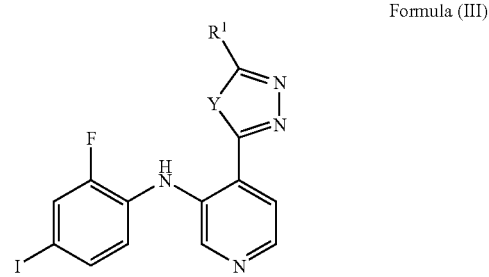

Formula (III)

or alternatively compounds of Formula (IIIa) or Formula (IIIb)

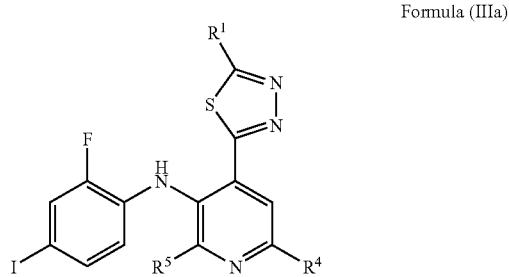

Formula (IIIa)

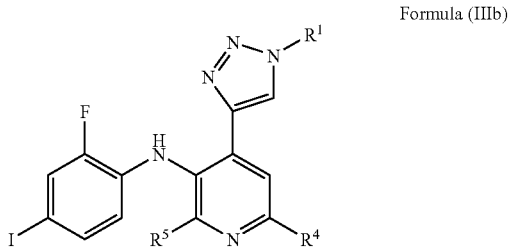

Formula (IIIb)

as well as tautomers, pharmaceutically acceptable salts and pharmaceutically active derivatives thereof,
the variables in Formula (III), Formula (IIIa) and Formula (IIIb) are defined as follows:

Y in Formula (III) is either O or NR';

$R^1$ is selected from hydrogen, trimethylsilyl, $C_1$-$C_6$-alkyl, $OR^6$, $C(O)OR^6$, $NR^7R^8$, $SR^6$, $NR^7S(O)(O)R'$, $NR^7C(O)R^6$, $NR^7C(O)NR^7R^6$, $NR^7C(O)OR^6$, $NR^7C(O)C(O)OR^6$, $C_1$-$C_4$-alkyl-NR'R", $C_1$-$C_4$-alkyl-heterocycloalkyl or $C_1$-$C_4$ alkyl-$(OR')_n$;

$R^4$ and $R^5$ are independently selected from hydrogen, halogen, $C_1$-$C_6$ alkyl or $C_1$-$C_6$ alkoxy, wherein said alkyl or alkoxy is substituted or unsubstituted;

$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR', $C_1$-$C_4$-alkyl-NR'R", $C_1$-$C_4$-alkyl-heterocycloalkyl, $C_1$-$C_4$ alkyl-(OR')$_n$ or $C_1$-$C_4$ alkyl-C(O)NR'R", wherein said alkyl, cycloalkyl, aryl, heteroaryl, heterocycloalkyl, and alkyl-heterocycloalkyl is substituted or unsubstituted; or $R^7$ and $R^8$ can be taken together with the atom to which they are attached to form a 4 to 10-membered heteroaryl or heterocyclic ring, each of which is substituted or unsubstituted; and R' and R" are independently selected from hydrogen, $C_1$-$C_6$-alkyl or aryl, wherein said alkyl or aryl is substituted or unsubstituted; or R' and R" can be taken together with the atom to which they are attached to form a 4 to 10-membered heteroaryl or heterocyclic ring, each of which is substituted or unsubstituted; and n is 0 to 2.

In preferred embodiments, the variants in Formula (IIIa) and Formula (IIIb) have the following meanings:

$R^1$ is selected from $OR^6$, $NR^7R^8$ or $SR^6$;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR' or $C_1$-$C_4$ alkyl-C(O)NR'R", wherein said alkyl is substituted or unsubstituted; or $R^7$ and $R^8$ can be taken together with the atom to which they are attached to form a 6 membered heterocyclic ring with 1 or 2 N atoms and optionally an O atom, which is substituted or unsubstituted; preferably said cyclic ring is morpholinyl, piperidinyl or piperazinyl;

R' and R" are independently either hydrogen or $C_1$-$C_6$-alkyl.

As said above $R^6$, $R^7$, $R^8$, R' and R" are optionally substituted. In this case they are independently substituted as described above.

In a preferred embodiment, the invention provides compounds of the Formulae (IVa) or (IVb):

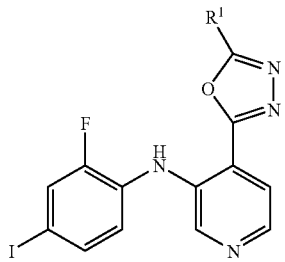

Formula (IVa)

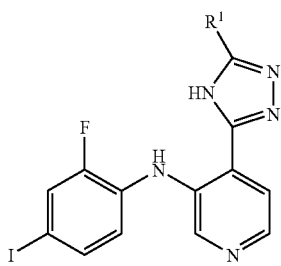

Formula (IVb)

as well as tautomers, pharmaceutically acceptable salts and pharmaceutically active derivatives thereof, wherein $R^1$ is selected from hydrogen, trimethylsilyl, $C_1$-$C_6$-alkyl, $OR^6$, $C(O)OR^6$, $NR^7R^8$, $SR^6$, $NR^7S(O)(O)R'$, $NR^7C(O)R^6$, $NR^7C(O)NR^7R^6$, $NR^7C(O)OR^6$, $NR^7C(O)C(O)OR^6$, $C_1$-$C_4$-alkyl-NR'R", $C_1$-$C_4$-alkyl-heterocycloalkyl or $C_1$-$C_4$ alkyl-(OR')$_n$;

$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR', $C_1$-$C_4$-alkyl-NR'R", $C_1$-$C_4$-alkyl-heterocycloalkyl, $C_1$-$C_4$ alkyl-(OR')$_n$ or $C_1$-$C_4$ alkyl-C(O)NR'R", wherein said alkyl, cycloalkyl, aryl, heteroaryl, heterocycloalkyl, and alkyl-heterocycloalkyl is substituted or unsubstituted; or $R^7$ and $R^8$ can be taken together with the atom to which they are attached to form a 4 to 10-membered heteroaryl or heterocyclic ring, each of which is substituted or unsubstituted; and R' and R" are independently selected from hydrogen, $C_1$-$C_6$-alkyl or aryl, wherein said alkyl or aryl is substituted or unsubstituted; or R' and R" can be taken together with the atom to which they are attached to form a 4 to 10-membered heteroaryl or heterocyclic ring, each of which is substituted or unsubstituted; and n is 0 to 2.

In preferred embodiments, the variants in Formula (IVa) and Formula (IVb) have the following meanings:

$R^1$ is selected from $OR^6$, $NR^7R^8$ or $SR^6$;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR', $C_1$-$C_4$ alkyl-C(O)NR'R", wherein said alkyl is substituted or unsubstituted; or $R^7$ and $R^8$ can be taken together with the atom to which they are attached to form a 6-membered heterocyclic ring with 1 or 2 N atoms and optionally an O atom, which is substituted or unsubstituted; preferably said cyclic ring is morpholinyl, piperidinyl or piperazinyl;

R' and R" are independently either hydrogen or $C_1$-$C_6$-alkyl; or

R' and R" can be taken together with the atom to which they are attached to form a 6-membered heterocyclic ring with 1 or 2 N atoms and optionally an O atom, which is substituted or unsubstituted.

As said above $R^6$, $R^7$, $R^8$, R' and R" are optionally substituted. In this case they are independently substituted as described above.

Compounds according to Formula (I) include in particular those selected from of the group consisting of:

5-[3-(2-Fluoro-4-iodo-phenylamino)-pyridin-4-yl]-3H-[1,3,4]oxadiazol-2-one,

[4-(5-Amino-[1,3,4]oxadiazol-2-yl)-pyridin-3-yl]-(2-fluoro-4-iodo-phenyl)-amine, 5-[3-(2-Fluoro-4-iodo-phenylamino)-pyridin-4-yl]-3H-[1,3,4]oxadiazole-2-thione, 5-[3-(2-Fluoro-4-iodo-phenylamino)-pyridin-4-yl]-2,4-dihydro-[1,2,4]triazol-3-one, (2-Fluoro-4-iodo-phenyl)-[4-(5-methylsulfanyl-[1,3,4]oxadiazol-2-yl)-pyridin-3-yl]-amine, and (2-Fluoro-4-iodo-phenyl)-[4-(5-morpholin-4-yl-[1,3,4]oxadiazol-2-yl)-pyridin-3-yl]-amine.

The employed terms have independently the meaning as described below:

A "substitutable ring carbon atom" in an aromatic group is a ring carbon bonded to a hydrogen atom. The hydrogen can be optionally replaced with a suitable substituent group. Thus, the term "substitutable ring carbon atom" does not include ring carbon atoms which are shared when two aromatic rings are fused. In addition, "substitutable ring atom" does not include ring carbon atoms when the structure depicts that they are already attached to a moiety other than hydrogen. Thus, the carbon atom bonded to $R^2$ in Structural Formula (II) is not a "substitutable ring atom" within the meaning of the term, as it is used herein.

"$C_1$-$C_{10}$-alkyl" refers to monovalent alkyl groups having 1 to 10 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl or benzoquinolyl.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"Acyl" refers to the group —C(O)R where R includes "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Alkoxy" refers to the group —O—R where R includes "$C_1$-$C_6$-alkyl" or "aryl" or "hetero-aryl" or "aryl $C_1$-$C_6$-alkyl" or "heteroaryl $C_1$-$C_6$-alkyl". Preferred alkoxy groups include for example, methoxy, ethoxy, phenoxy and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R and R' is independently hydrogen or "$C_1$-$C_6$-alkyl", or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy" refers to a group —$OSO_2$—R wherein R is selected from H, "$C_1$-$C_6$-alkyl", "$C_1$-$C_6$-alkyl" substituted with halogens, e.g., an —$OSO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$- alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfanyl" refers to groups —S—R where R includes H, "$C_1$-$C_6$-alkyl", "$C_1$-$C_6$-alkyl" optionally substituted with halogens, e.g. a —S—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"Halogen" refers to fluoro, chloro, bromo and iodo.

"Cyano" refers to C≡N.

Where tautomerism, like e.g. keto-enol tautomerism, of compounds of the present invention or their prodrugs may occur, the individual forms, like e.g. the keto and enol form, are claimed separately and together as mixtures in any ratio. The same applies for stereoisomers, like e.g. enantiomers, cis/trans isomers, conformers and the like. Tautomers include but are not limited to the following structures:

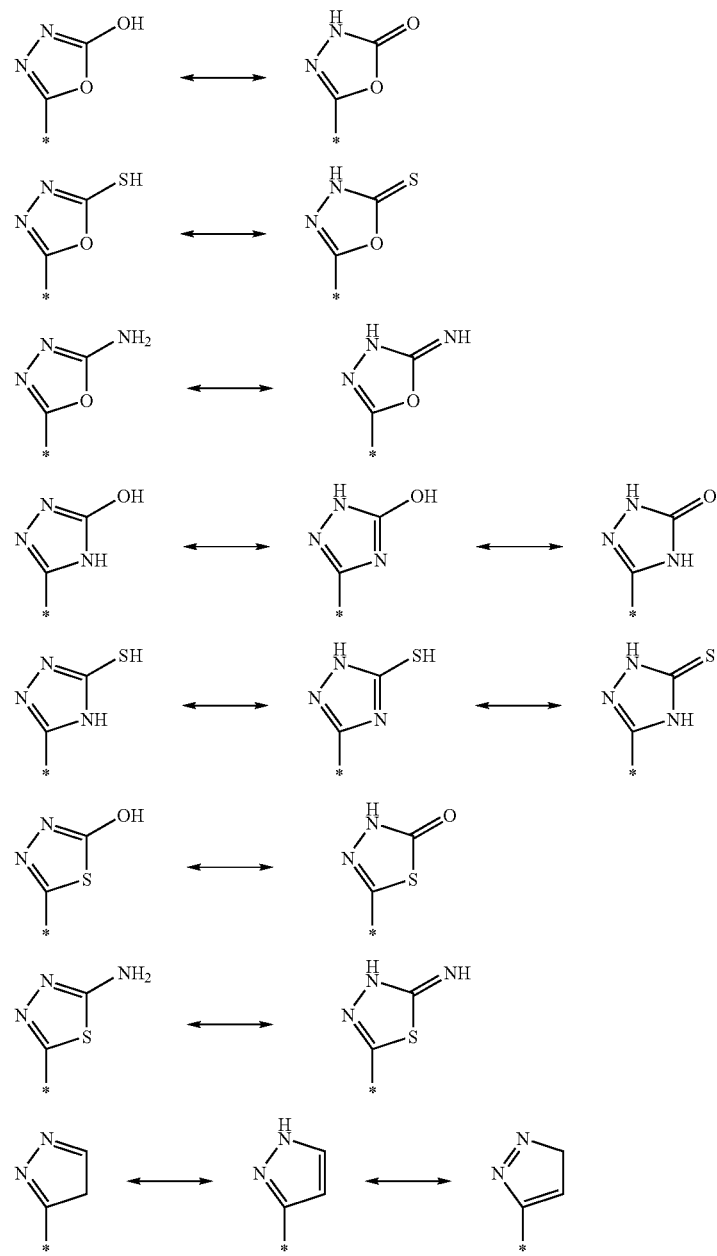

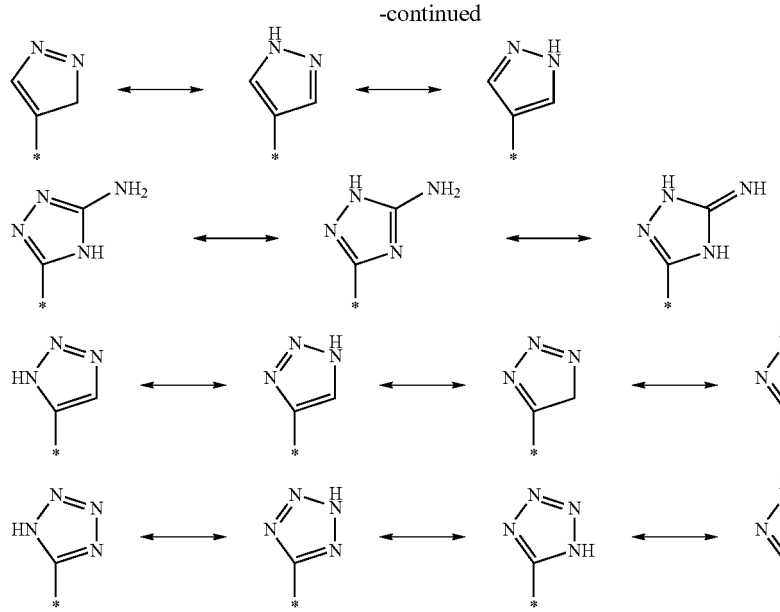

Metabolites of compounds of the present invention are also within the scope of the present invention.

In one embodiment the MEK inhibitor, in particular any of the cited MEK inhibitors inhibits the activity of MEK1 at a concentration of less than 100 µM. In another embodiment the MEK inhibitor inhibits the activity of MEK1 at a concentration of less than 10 µM. In another embodiment the MEK inhibitor inhibits the activity of MEK1 at a concentration of less than 1 µM. In another embodiment the MEK inhibitor inhibits the activity of MEK1 at a concentration of less than 0.1 µM.

The invention relates in a second aspect to a method of treating a mammal suffering from or susceptible to a hyperproliferative disease comprising administering to the mammal a therapeutically effective amount of a compound of Formula (I) or a pharmaceutically acceptable salt or a pharmaceutically active derivative thereof.

A hyperproliferative disease may be a cancerous disease including but not limiting to cancer types such as brain, lung, squamous cell, bladder, gastic, pancreatic, breast, head, neck, renal, kidney, ovarian, prostate, colorectal, esophageal, testicular, gynecological or thyroid cancer, or a non cancerous hyperproliferative disease such as benign hyperplasia of the skin (e.g., psoriasis), restenosis, or prostate (e.g., benign prostatic hypertrophy (BPH)).

In one embodiment the hyperproliferative disease is related to the hyperactivity of MEK as well as diseases associated to MEK in mammals, or diseases mediated by aberrant cell proliferation, such as cancer or inflammation.

A disease related to the "hyperactivity of MEK" refers to a disease, which can be treated by using any compound according to Formula (I) and which encompasses all diseases in which the upregulation and/or activity of MEK needs to be decreased irrespective of the cause of such disease.

"Pharmaceutically acceptable salts or complexes" refer to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention. Also comprised are salts, which are formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, methane sulfonic acid, naphthalene disulfonic acid, and polygalacturonic acid, as well as salts formed with basic amino acids such as Lysine or Arginine.

A "pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. For example, a chemical masking group for alcohol derivatives could be selected from carboxylic acid ester (e.g. acetate, lysine ester) or phosphoric acid esters (e.g. phosphoric acid monoester).

In a preferred embodiment the invention relates to method of treating a mammal suffering from or susceptible to a hyperproliferative disease comprising administering to the mammal a therapeutically effective amount of a compound of Formulae (II), (IIIa) or (IIIb) or a pharmaceutically acceptable salt or a pharmaceutically active derivative thereof. In one embodiment said hyperproliferative disease is cancer.

The invention also relates to the treatment of a hyperproliferative disease in a mammal that comprises administering to said mammal a therapeutically effective amount of a compound of Formula (I), in combination with an anti-tumor agent selected from the group consisting of mitotic inhibitors, alkylating agents, antimetabolites, intercalating antibiotics, growth factor inhibitors, cell cycle inhibitors, enzyme inhibitors, topoisomerase inhibitors, biological response modifiers, antihormones, angiogenesis inhibitors, and anti-androgens. It is well known in the art, which anti-tumor agent can be selected from combination. In a preferred embodiment, a compound of Formulae (II), (III), (IVa) or (IVb) is administered in combination with an anti-tumor agent as described above.

The invention relates in a third aspect to the use of a MEK inhibitor according to Formula (I) or a pharmaceutically acceptable salt or a pharmaceutically active derivative thereof as a medicament.

In a preferred embodiment, the invention relates to the use of a compound according to Formulae (II), (III), (IVa) or (IVb) or a pharmaceutically acceptable salt or a pharmaceutically active derivative thereof as a medicament. In one embodiment the invention relates to the use of a compound selected from the group of 5-[3-(2-Fluoro-4-iodo-phenylamino)-pyridin-4-yl]-3H-[1,3,4]oxadiazol-2-one,
[4-(5-Amino-[1,3,4]oxadiazol-2-yl)-pyridin-3-yl]-(2-fluoro-4-iodo-phenyl)-amine,
5-[3-(2-Fluoro-4-iodo-phenylamino)-pyridin-4-yl]-3H-[1,3,4]oxadiazole-2-thione,
5-[3-(2-Fluoro-4-iodo-phenylamino)-pyridin-4-yl]-2,4-dihydro-[1,2,4]triazol-3-one,
(2-Fluoro-4-iodo-phenyl)-[4-(5-methylsulfanyl-[1,3,4]oxadiazol-2-yl)-pyridin-3-yl]-amine, and
(2-Fluoro-4-iodo-phenyl)-[4-(5-morpholin-4-yl-[1,3,4]oxadiazol-2-yl)-pyridin-3-yl]-amine as a medicament.

The invention relates to all of the compounds disclosed in the examples.

The invention relates in a forth aspect to the use of a MEK inhibitor according to Formula (I) or a pharmaceutically acceptable salt or a pharmaceutically active derivative thereof for the preparation of a medicament for the treatment of a hyperproliferative disease. In one embodiment, said use relates to the preparation of a medicament for the treatment of cancer.

In a preferred embodiment the invention relates to the use of a compound according to Formulae (II), (III), (IVa) or (IVb) or a pharmaceutically acceptable salt or a pharmaceutically active derivative thereof for the preparation of a medicament for the treatment of a hyperproliferative disease. In one embodiment, said use relates to the preparation of a medicament for the treatment of cancer.

The invention relates in a fifth aspect to the use of a MEK inhibitor according to Formula (I) or a pharmaceutically acceptable salt or a pharmaceutically active derivative thereof for the treatment of a hyperproliferative disease. In one embodiment, said use relates to the treatment of cancer.

In a preferred embodiment the invention relates to the use of a compound according to Formulae (II), (III), (IVa) or (IVb) or a pharmaceutically acceptable salt or a pharmaceutically active derivative thereof for the treatment of a hyperproliferative disease. In one embodiment, said use relates to the preparation of a medicament for the treatment of cancer.

Furthermore, the invention provides in a sixth aspect pharmaceutical compositions comprising a compound of Formula (I), or a pharmaceutically acceptable salt or a pharmaceutically active derivative thereof, as active ingredient together with a pharmaceutically acceptable carrier.

In a preferred embodiment the invention relates to a pharmaceutical composition comprising a compound of Formulae (II), (III), (IVa) or (IVb), or a pharmaceutically acceptable salt or a pharmaceutically active derivative thereof, as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients like one or more additional compounds of the present invention, or a prodrug compound or other MEK inhibitors.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula (I) can be combined as the active ingredient in admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound (a compound of Formulae (I), (II), (III), (IVa) or (IVb) in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds according to Formulae (I), (II), (III), (IVa) or (IVb) may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating cancer or other hyperproliferative diseases for which compounds of Formulae (I), (II), (III), (IVa) or (IVb) are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Furthermore, the invention provides in a seventh aspect a method of preparing a compound of Formula (I).

In a preferred embodiment the invention relates to a method of preparing compounds of Formulae (II), (III), (IVa) or (IVb).

The compounds according to Formula (I) can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds according to Formula (I). Those skilled in the art will readily understand that known variations of the conditions and processes of the following preparative procedures can be used to prepare these compounds. The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

Illustrations of the preparation of compounds according to Formula (Ia) are shown in the following schemes. Unless otherwise indicated in the schemes, the variables have the same meaning as described above.

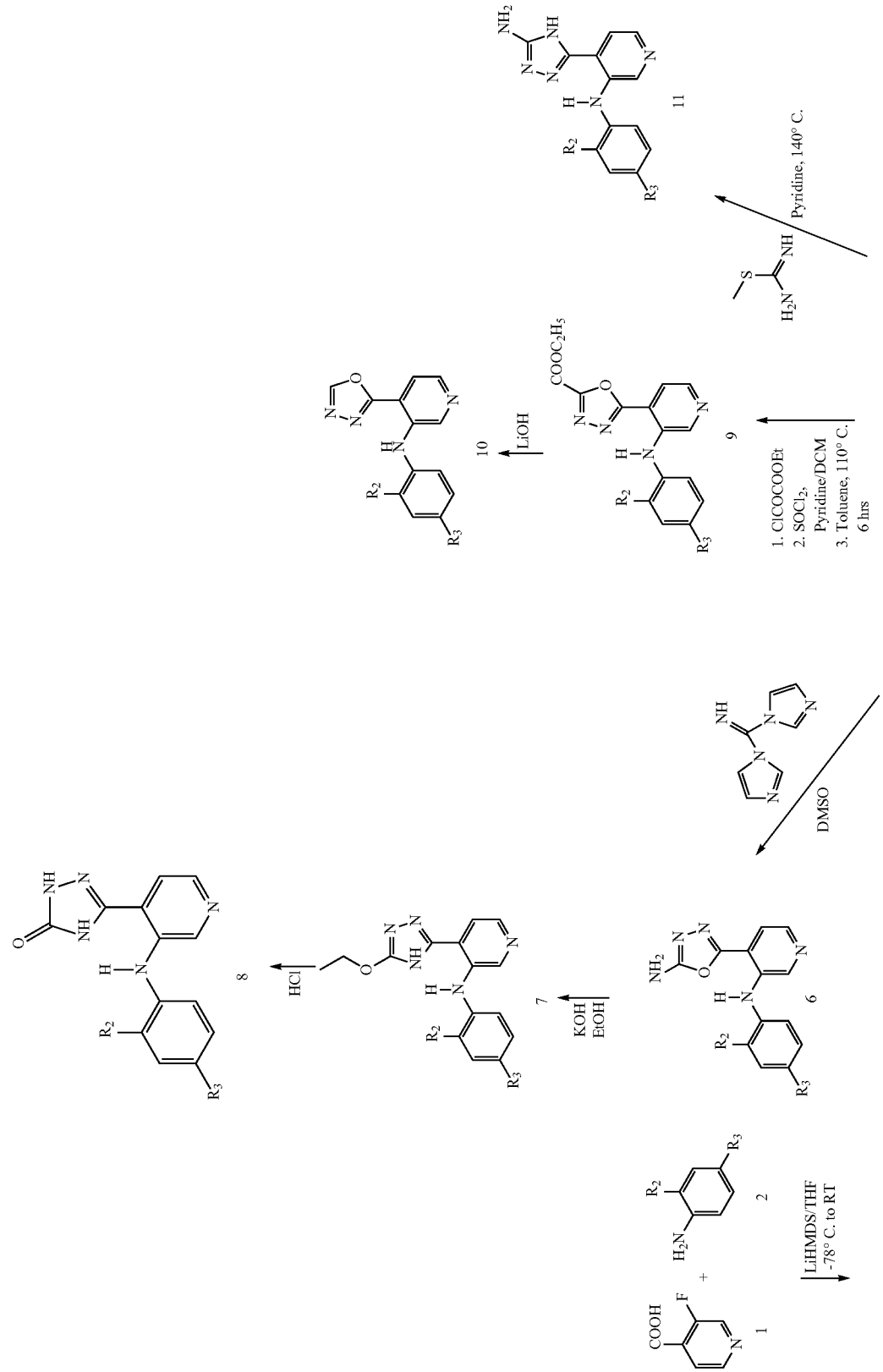

-continued
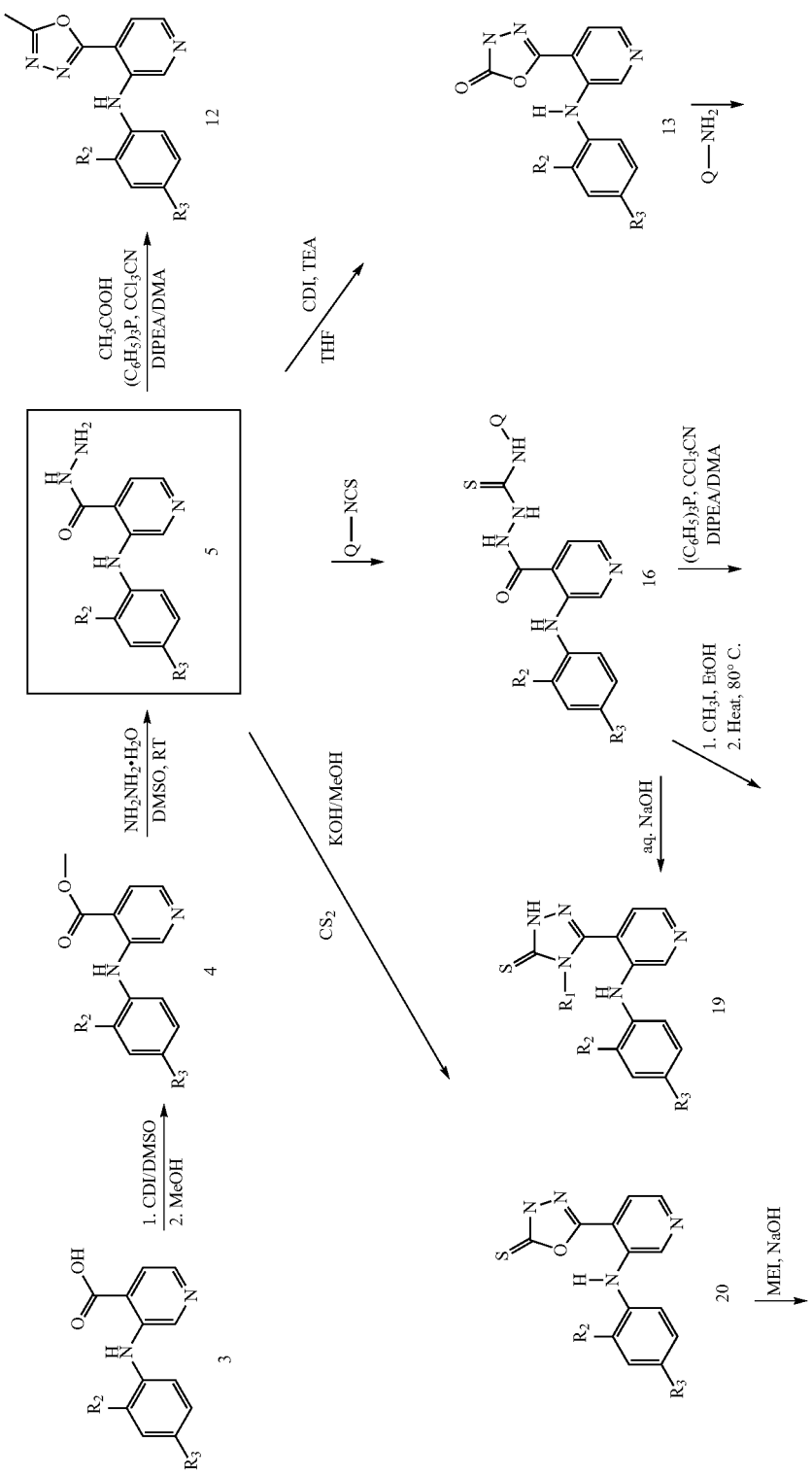

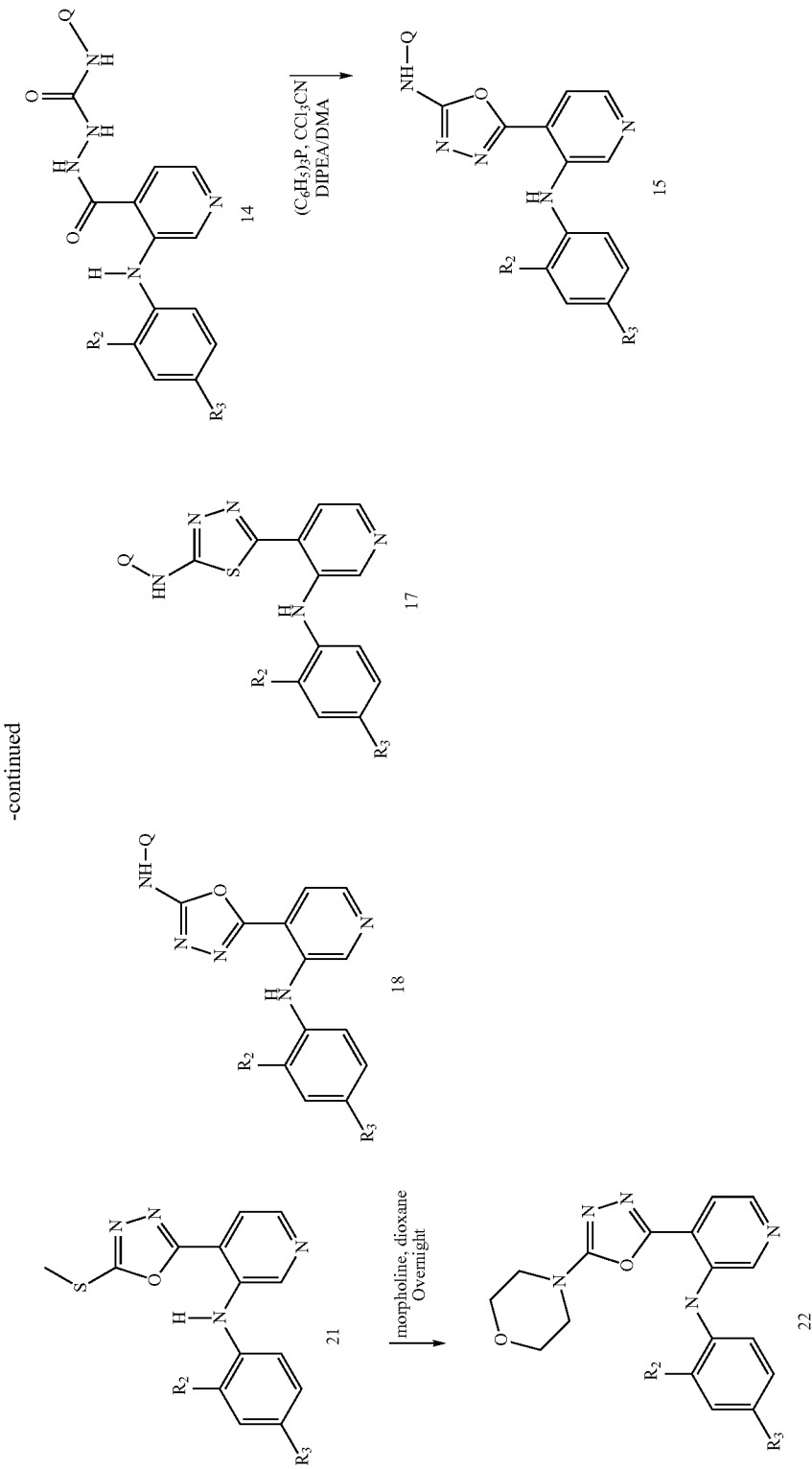

Scheme 1 illustrates the synthesis of a group of example compounds in the present invention. In first step anilines (2) are reacted with 3-fluoro isonicotinic acids (1) in inert solvents, preferably THF, by addition of a base, preferably but not limited to LiHMDS. In step 2 the 3-anilino isonicotinic acids (3) are transformed to simple esters such as methyl ester (4) by employing coupling agents such as PyBOP; CDI etc. and simple alcohols, e.g. methanol. The resulting esters are easily converted to hydrazides (5) by heating with the corresponding hydrazines in alcoholic solvents. These hydrazides, as illustrated in Scheme 1, serve as key intermediates for the formation of a great variety of heterocyclic rings. For example, treatment with 1,1-di-1H-imidazol-1-yl-methyleneamine affords [1,3,4]oxadiazol-2-amines such as compound 6 in Scheme 1. These compounds can be rearranged by heating in alcoholic solutions of KOH to 5-alcoxy-[1,2,4]triazoles (7) which can be in turn hydrolyzed with acid to the corresponding triazolones (8). Hydrazides (5) can also react with 3-Chloro-2-oxo-propionic acetates and then can be cyclized into [1,3,4]oxadiazole-2-carboxylate derivatives (9), which in turn can be decarboxylated to unsubstituted oxadiazoles (10) with treatment with lithium or sodium hydroxide or other similar reagents. Coupling/cyclization of 5 with 2-amino-thioacetimidic acid esters affords [1,2,4]triazoles-3-amines (11). Condensations of 5 with acids in the presence of triphenylphosphine/trichloroacetonitrile affords 2-alkyl-[1,3,4]oxadiazoles (12). Condensation of 5 with carbonyldiimidazole results in [1,3,4]oxadiazol-2-ones (13). The latter can be ring-opened with amines to analogs such as 14, which in turn can be cyclized into N-substituted [1,3,4]oxadiazoles-2-amines (15). Reaction of 5 with isothiocyanates affords analogs such as 16 which can be cyclized into either substituted [1,3,4]thiazodiazoles-3-amines (17), or [1,3,4]oxadiazoles-2-amines (18), or [1,2,4]triazole-3-thiones (19). Condensation of 5 with carbon disulfide under basic conditions afforded [1,3,4]oxadiazol-2-thiones (20), which can be S-alkylated to compounds 21, which in turn can react with various nucleophiles to afford 2-substituted [1,3,4]oxadiazole analogs, such as 22.

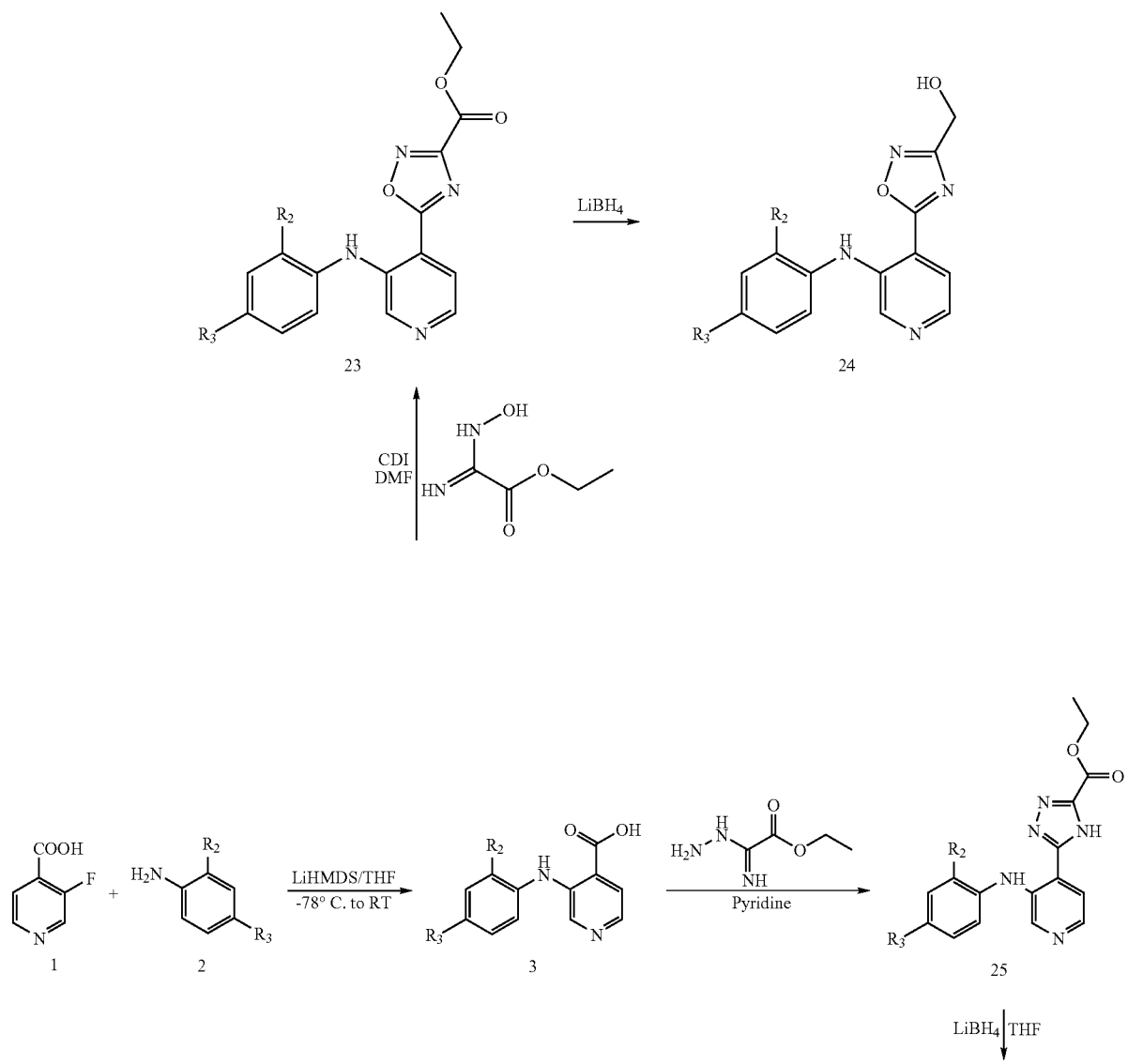

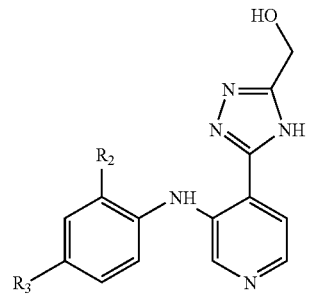

Scheme 2 illustrates the general synthesis of examples with various heterocyclic systems stemming from intermediate acids 3 instead of hydrizides 5. Acids 3 can be coupled with hydroxylamino-imino-acetates and eventually cyclize into 1,2,4-oxadiazole-3-carboxylic acid esters (23) which in turn can be reduced to the corresponding hydroxylmethyl derivatives (24). Finally, intermediate 3, similarly to the reactions that formed 23, and 24 can react with hydrazine-imino-acetates to form 1,2,4-triazole-3-carboxylic acid esters (25) and the corresponding alcohols (26) after borohydride reduction.

Scheme 3

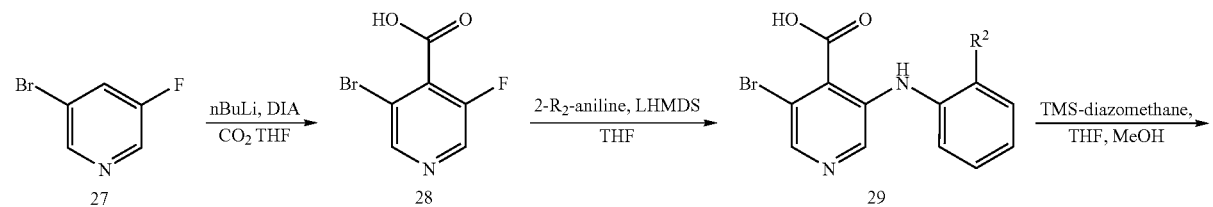

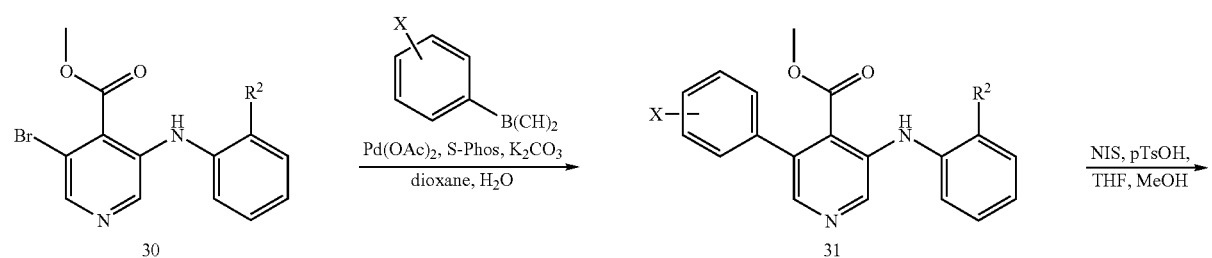

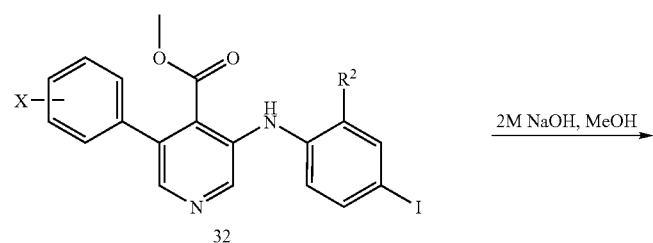

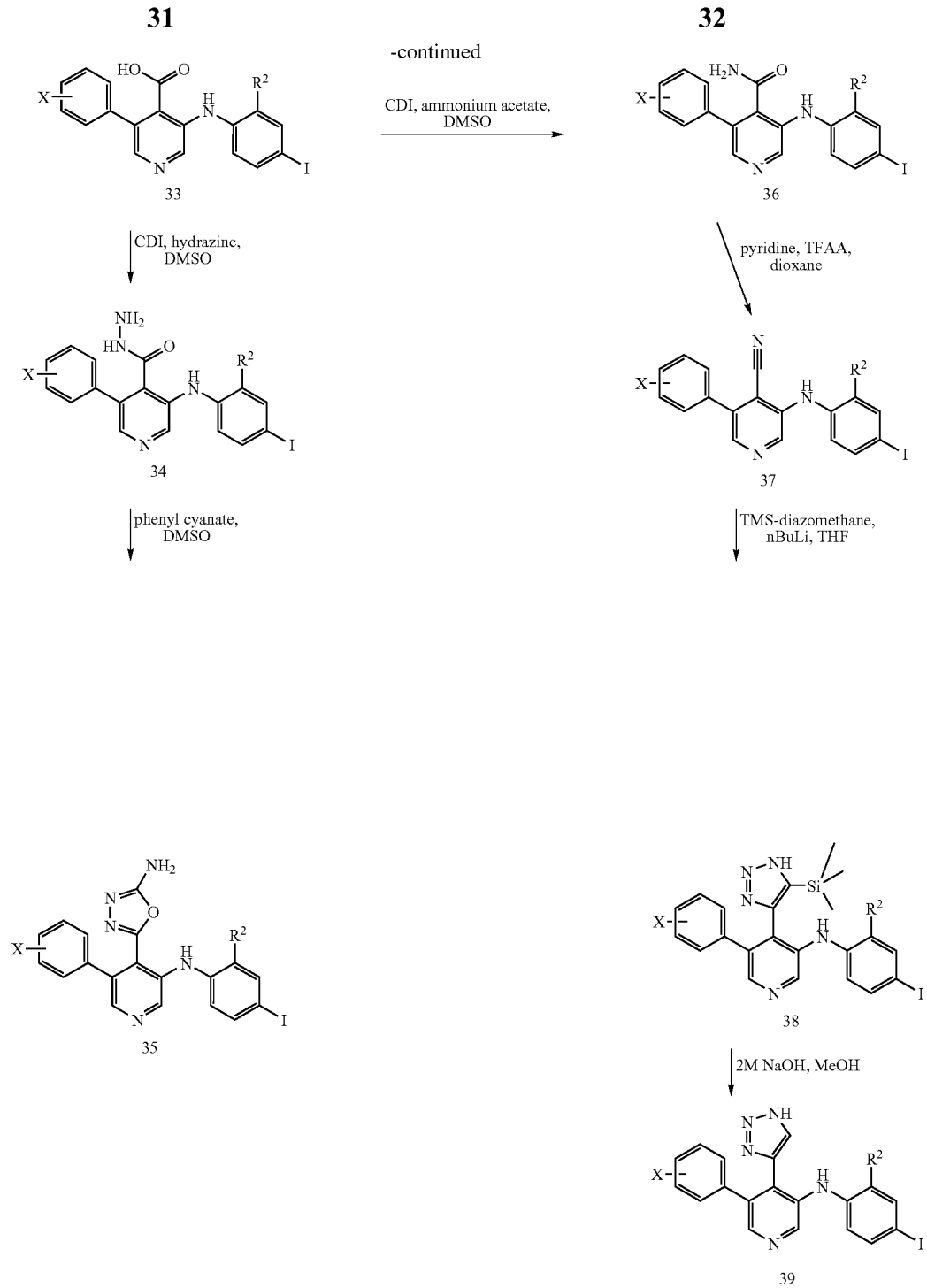

Scheme 3 illustrates the synthesis of examples with substitutions in the 5 position of the pyridine core, and in particularly phenyl substitutions. 3-Bromo-5-Fluoro-pyridine (27) is first 4-lithiated and then treated with $CO_2$ to form the isonicotinic acid (28), which in turn is coupled with various anilines to afford biaryl systems such as 29. The acid functionality is first protected as simple esters (30) and then reacted under Suzuki or other palladium-catalyzed coupling conditions to afford a variety of 5-substituted analogs, including the ones described with structure 31. Halogenation, such as iodination with NIS under acidic conditions, gives rise to compounds under structure 32, which are deprotected to the free acids (33). These acids are activated with typical coupling reagents, such as CDI or others, to react with either hydrazines or amines to produce hydrazides (34) or amides (36) respectively. The former are in turn cyclized into systems similar to the ones described in Scheme 1, including aminoxadiazoles such as structure 35. Amides 36 can typically be first dehydrated to the corresponding nitriles (37), which are useful intermediates in the construction of various heterocyclic compounds. The example shown in Scheme 3 is the conversion of nitrile 37 into triazoles 38 and 39 by reaction with diazomethane.

Scheme 4

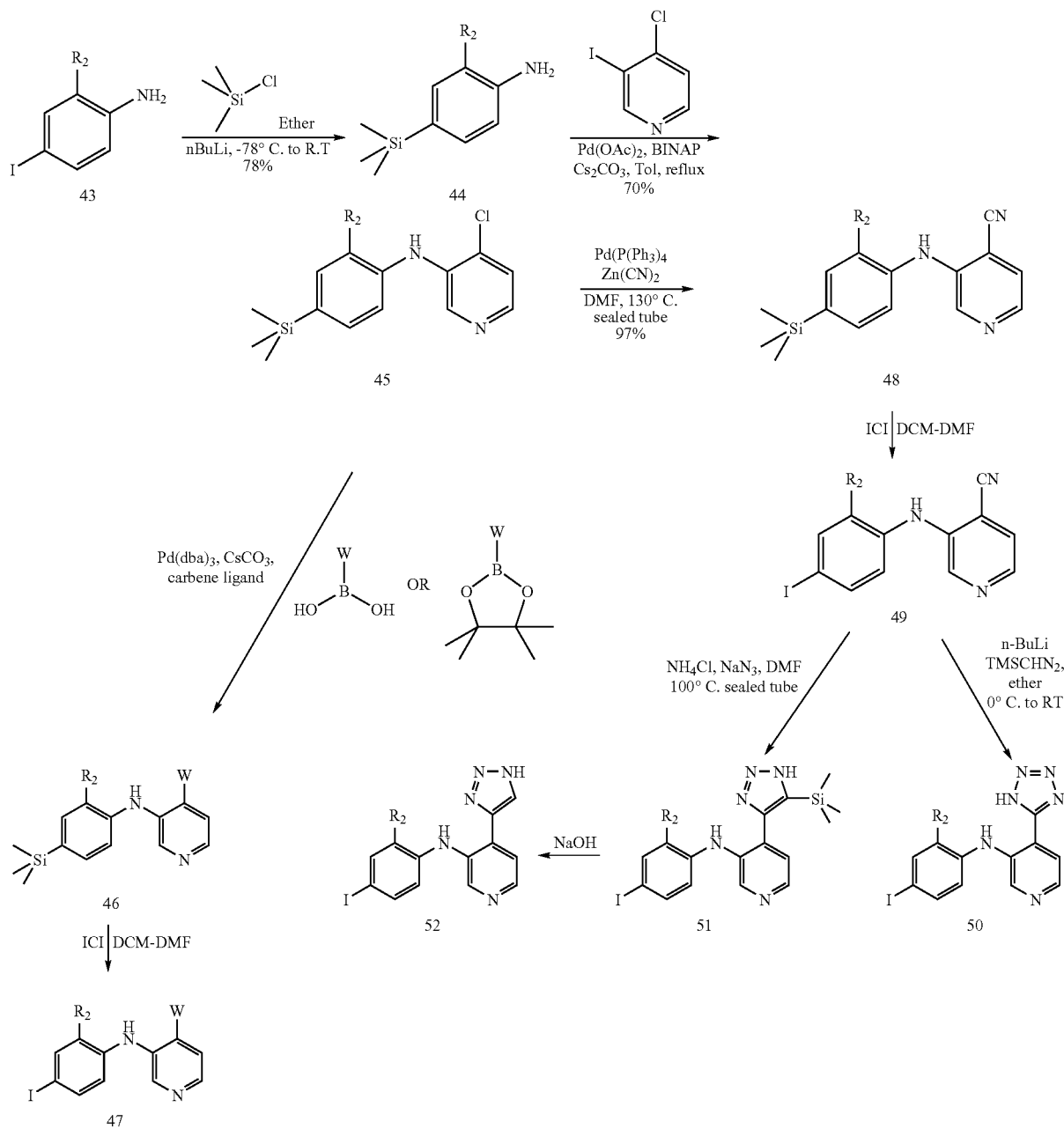

Scheme 4 illustrates the general synthesis of additional examples with various types of W substituents. According to this scheme, various 4-iodo-anilines (43) are converted to the corresponding 4-trimethylsilyl derivatives (44), which in turn are coupled under palladium-catalyzed conditions with various 4-cholro-pyridines to form key (4-chloro-pyridin-3-yl-phenyl)-amines (45). These intermediates are functionalised using a variety of either Suzuki or other palladium-catalyzed coupling reactions to introduce a great variety of W groups in the 4-pyridyl position (46). These compounds are typically converted to their halogenated analogs (47) (e.g. iodo or other) by displacement of the trimethylsilyl group. Alternatively, the 4-cholopyridyl group of 45 can be converted to a 4-cyanopyridyl group by heating in sealed tube in the presence of $Pd(PPh_3)_4$ and $Zn(CN)_2$. This cyano intermediate (48) allows the access of various compounds with certain heterocyclic ring systems in the 4-pyridyl position, such as tertazoles (50), triazoles (51, 52), and others.

Suitable anilines, pyridines, and other derivatives, reagents, and starting materials are commercially available from Alpha Aesar, Ward Hill, Mass., USA; Sigma-Aldrich Milwakee, Wis., USA; or from Acros Organics, Morris Plains, N.J., USA; or can be routinely prepared by procedures described in "March's Advanced Organic Chemistry: Reactions, Mechanisms, and Structure", 5th Edition; John Wiley & Sons.

Unless otherwise noted, all non-aqueous reactions were carried out either under an argon or nitrogen atmosphere with commercial dry solvents. Compounds were typically purified using flash column chromatography using Merck silica gel 60 (230-400 mesh). In certain cases reverse phase preparative HPLC was used for purification. The ¹H-NMR spectra were recorded on a Joel ECP-400 (400 MHz for ¹H-NMR) using typically $d_6$-dimethylsulfoxide or $d_4$-methanol as solvent; chemical shifts are reported in ppm relative to tetramethylsilane.

Analytical LC/MS was performed using the following two methods:

Method A: A Discovery® $C^{18}$, 5 µm, 3×30 mm column was used at a flow rate of 400 µL/min, sample loop 5 µL, mobile phase: (A) water with 0.1% formic acid, mobile phase, (B) methanol with 0.1% formic acid; retention times are given in minutes. Method details: (I) runs on a Quaternary Pump G1311A (Agilent) with UV/V is diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry® $C^{18}$, 3.5 µm, 4.6×75 mm column at a flow rate of 1 mL/min, sample loop 10 µL, mobile phase (A) is water with 0.05% TFA, mobile phase (B) is ACN with 0.05% TFA; retention times are given in minutes. Methods details: (I) runs on a Binary Pump G1312A (Agilent) with UV/V is diode array detector G1315B (Agilent) and Applied Biosystems API3000 MS detector in ESI+modus with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

| Abbreviations | Designation |
|---|---|
| CDI | N,N-Carbonyldiimidazole |
| DCM | Dichloromethane |
| DIPEA | N-Ethyldiisopropylamine |
| DMF | N,N-Dimethylformamide |
| DMSO | Dimethylsulfoxide |
| EDC | 1-(3-Dimethylaminopropyl)-3-ethylcarbodiimide hydrochloride |
| HPLC | High pressure liquid chromatography |
| LC/MS | Liquid chromatography/Mass Spectrometry |
| LiHMDS. | Lithium hexamethyldisilazide |
| MCPBA | 3-Chloroperoxybenzoic acid |
| NT | Not Tested |
| NMR | Nuclear Magnetic Resonance |
| PyBOP | Benzotriazole-1-yl-oxy-trispyrrolidinophosphonium hexafluorophosphate |
| RT | Room Temperature |
| TEA | Triethylamine |
| Tert | Tertiary-butyl |
| TFA | Trifluoroacetic acid |
| THF | Tetrahydrofurane |
| TLC | Thin Layer Chromatography |

Literature:
Crews et al., Science 1992, 258, 478-80
Reddy et al., Cancer Metastasis Rev. 2003, 22, 395-403
Chang et al., Leukemia 2003, 17,1263-93,
Lee et al., Exp. Mol. Med. 2006, 38, 27-35
WO 00/42029,
WO 04/056789
WO 05/051301

EXAMPLES

The examples presented below are intended to illustrate particular embodiments of the invention, and are not intended to limit the scope of the specification or the claims in any way. The example and intermediate numbering used in this section are independent of the numbering used in Schemes 1-4.

Intermediate 1

3-(2-Fluoro-4-iodo-phenylamino)-isonicotinic acid

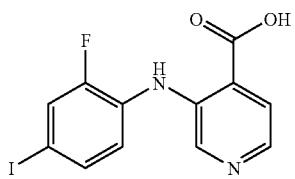

A mixture of 4-iodo-2-fluoroaniline (20.0 g, 84.38 mmol) in anhydrous tetrahydrofuran (80 mL) was cooled to −65° C. under an inert atmosphere, prior to slow addition of 1.0 M lithium bis(trimethylsilyl)amide (255 mL, 255 mmol) at a rate that maintained the internal temperature below −55° C. After final addition, the thick slurry was stirred for 30 minutes and then treated with 3-fluoro-isonicotinic acid (8.0 g, 56.69 mmol). The mixture was stirred at room temperature for 4 days and then poured into aqueous 2.0 N sodium hydroxide (1000 mL) and ethyl acetate (250 mL). The layers were separated and the organics were again extracted with aqueous sodium hydroxide (2×1000 mL). The pH of the combined aqueous fractions was adjusted to 2 with concentrated hydrochloric acid, which effected precipitation of a solid. The material was filtered, washed with water (300 mL) and dried under high vacuum at 40° C. for 18 h to afford 3 (19.05 g, 53.19 mmol, 94%) as a yellow solid. MS [359 (M+1)]. ¹H NMR (400 MHz, DMSO-$D_6$): 7.3565 (t, J=8.8 Hz, 1H), 7.5509 (d, J=8.4 Hz, 1H), 7.7521 (m, 2H), 8.1175 (d, J=4.7 Hz, 1H), 8.4472 (s, 1H), 9.2184 (s, 1H)

Intermediate 2

3-(2-Fluoro-4-iodo-phenylamino)-isonicotinic acid methyl ester

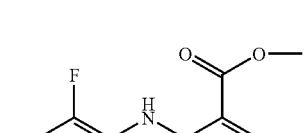

A suspension of 3-(2-Fluoro-4-iodo-phenylamino)-isonicotinic acid (12.0 g, 33.51 mmol) and CDI (7.0 g, 43.17 mmol) in anhydrous dimethyl sulfoxide (120 mL) was stirred at room temperature for 16 h, prior to addition of methanol (15.0 g, 468.15 mmol). The dark-yellow solution was stirred at room temperature for 2 h and then slowly poured into water (900 mL). The resultant precipitate was filtered and the cake was washed with water (2×300 mL) and dried under high vacuum at 40° C. for 16 h to afford 2 (12.11 g, 32.54 mmol, 97%) as a salmon-colored solid. ¹H-NMR: δ 3.88 (s, 3H);

7.30 (dd, 1H); 7.54 (ddd, 1H); 7.70 (d, 1H); 7.74 (dd, 1H); 8.13 (d, 1H); 8.41 (d, 1H); 8.88 (br s, 1H).

Intermediate 3

3-(2-Fluoro-4-iodo-phenylamino)-isonicotinic acid hydrazide

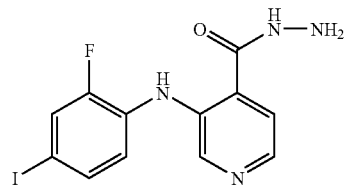

A suspension of 3-(2-Fluoro-4-iodo-phenylamino)-isonicotinic acid methyl ester (11.50 g, 30.90 mmol) in isopropanol (200 mL) was treated with hydrazine hydrate (6 mL) and the mixture was heated to gentle reflux for 17 h. The resultant precipitate was filtered, washed with isopropanol (50 mL) and dried under high vacuum for 14 h to give 3 (9.46 g, 25.42 mmol, 82%) as a yellow, crystalline solid. $^1$H-NMR: δ 4.65 (br s, 2H); 7.28 (dd, 1H); 7.49 (m, 2H); 7.68 (dd, 1H); 8.14 (d, 1H); 8.52 (s, 1H); 9.34 (brs, 1H); 10.22 (brs, 1H).

Example 1

5-[3-(2-Fluoro-4-iodo-phenylamino)-pyridin-4-yl]-3H-[1,3,4]oxadiazol-2-one

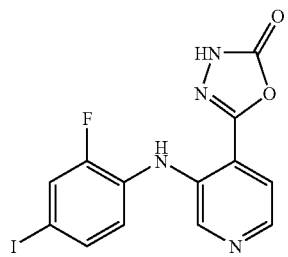

To a solution of 3-(2-Fluoro-4-iodo-phenylamino)-isonicotinic acid hydrazide (152 mg, 0.41 mmol) in THF (6 mL) contained TEA (60 μl, 0.43 mmol) were added Di-imidazol-1-yl-methanone (95 mg, 0.57 mmol) at 0° C. The reaction mixture was warmed to RT and stirred for 5 h, additional TEA (40 μl) and CDI (50 mg) were added, and the reaction mixture was stirred overnight at RT. The precipitate was filtered, the solid washed with MeOH. Yield: yellow solid 123 mg. LC-MS (Method A) [5.50 min; 399(M+1)].

Example 2

[4-(5-Amino-[1,3,4]oxadiazol-2-yl)-pyridin-3-yl]-(2-fluoro-4-iodo-phenyl)-amine

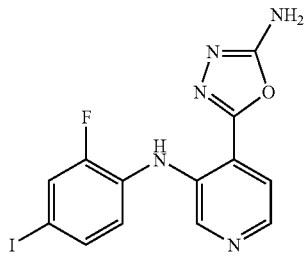

To a solution of 3-(2-Fluoro-4-iodo-phenylamino)-isonicotinic acid hydrazide (1 g, 2.68 mmol) in DMSO (6 mL) were added 1,1-di-1H-imidazol-1-yl-methyleneamine (864 mg, 5.36 mmol). The reaction mixture was stirred at RT for 18 h. Quenching of the reaction by adding water (60 mL). A solid precipitated out. The solid was filtered, washed with water and cold methanol. Yield: white solid 1.0 g. LC-MS (Method A) [4.66 min; 398(M+1)].

Synthesis of 1,1-di-1H-imidazol-1-yl-methyleneamine

To a solution of 1H-imidazole (3.52 g, 51.6 mmol), in DCM (250 mL) cyanic bromide was added (1.82 g, 17.2 mmol). The reaction mixture was stirred at 40° C. for 30 min. Part of the solvent was evaporated, leaving around 30 mL, then cooled at 0° C. for 1 h resulting in a white precipitate which was filtered to afford the expected product 3.3 g.

Example 3

5-[3-(2-Fluoro-4-iodo-phenylamino)-pyridin-4-yl]-3H-[1,3,4]oxadiazole-2-thione

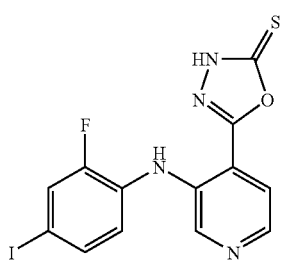

To a solution of 3-(2-Fluoro-4-iodo-phenylamino)-isonicotinic acid hydrazide (744 mg, 2.ommol) in methanol (15 mL) were added dithiomethane (0.22 mL, 4.66 mmol), followed by potassium hydroxide (2.51 mL, 2.13 mmol). The reaction mixture was stirred at 60° C. for 7 h. The solvent was evaporated and the residue was dissolved in ethyl acetate (50 mL), washed with Brine (15 mL×3), dried over anhydrous MgSO$_4$, filtered, removed off solvent. Residue was subjected to silica gel column (EtOAc:Hexane=1:1) collected product 210 mg. LC-MS (Method A) [5.71 min; 415(M+1)]

Example 4

5-[3-(2-Fluoro-4-iodo-phenylamino)-pyridin-4-yl]-2,4-dihydro-[1,2,4]triazol-3-one

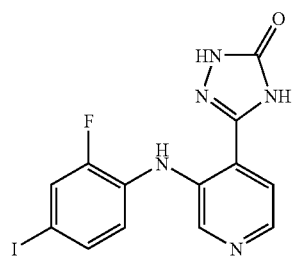

[4-(5-Ethoxy-4H-[1,2,4]triazol-3-yl)-pyridin-3-yl]-(2-fluoro-4-iodo-phenyl)-amine (80 mg) was added conc. HCl (4 mL). The reaction mixture was stirred at 90° C. for 4 hr, cooled and filtered, the solid was washed with water and methanol. Yield: white solid 30 mg. LC-MS (Method A) [5.23 min; 398(M+1)]

Example 5

(2-Fluoro-4-iodo-phenyl)-[4-(5-methylsulfanyl-[1,3,4]oxadiazol-2-yl)-pyridin-3-yl]-amine

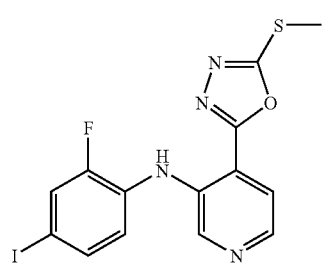

The reaction mixture of 5-[3-(2-Fluoro-4-iodo-phenylamino)-pyridin-4-yl]-3H-[1,3,4]oxadiazole-2-thione (600 mg, 1.45 mmol), Iodomethane (216 mg, 1.52 mmol) and 1 eq. NaOH (1.45 mL) in ethanol (10 mL) was stirred for overnight. The solvent was removed, ethyl acetate (50 mL) was added to the the residue, which was washed with Brine (20 mL×3). Dried over anhydrous MgSO₄ was added, filtered, and the solution evaporated.

Residue was subjected to silica gel column (EtOAc:Hexane=1:1), Yield: 245 mg. LC-MS (Method A) [5.72 min; 426(M+1)]

Example 6

(2-Fluoro-4-iodo-phenyl)-[4-(5-morpholin-4-yl-[1,3,4]oxadiazol-2-yl)-pyridin-3-yl]-amine

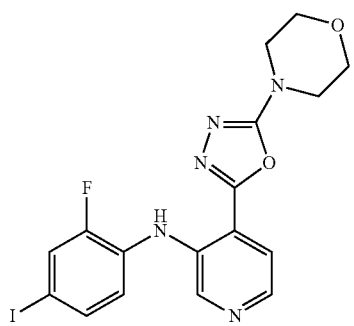

To a solution of (2-Fluoro-4-iodo-phenyl)-[4-(5-methylsulfanyl-[1,3,4]oxadiazol-2-yl)-pyridin-3-yl]-amine (100 mg, 0.23 mmol) in dioxane (5 mL) were added morphline (101 mg, 1.17 mmol). The reaction mixture was stirred at 120° C. for 8 h. The solvent was evaporated, residue was purified with prep plate (CH2Cl2:MeOH=20:1 5% TEA), collected product 24 mg. LC-MS (Method A) [5.20 min; 468(M+1)]

Example 7

(2-Fluoro-4-iodo-phenyl)-[4-(5-methylamino-[1,3,4]thiadiazol-2-yl)-pyridin-3-yl]-amine

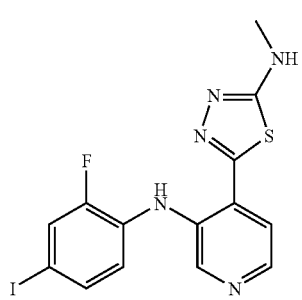

To a solution of N'-[3-(2-Fluoro-4-iodo-phenylamino)-pyridine-4-carbonyl] of hydrazinecarbothioic acid N-methylamide (150 mg, 0.34 mmol) in DMA (2 mL) added PS-Triphenyl-phosphane (353 mg, 1.35 mmol), Trichloro-acetonitrile (97 mg, 0.67 mmol), and DIEPA (0.17 mL, 1.01 mmol). The reaction mixture was stirred at 100° C. for 4 hrs, and then filtered, and and the volatiles evaporated. The crude product was purified by preparative HPLC to afford 8 mg of the desired product. LC/MS (Method A) [5.03 min; 428(M+1)].

Example 8

5-[3-(2-Fluoro-4-iodo-phenylamino)-pyridin-4-yl]-4-methyl-2,4-dihydro-[1,2,4]triazole-3-thione

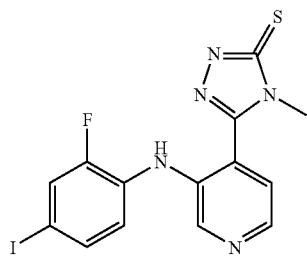

N'-[3-(2-Fluoro-4-iodo-phenylamino)-pyridine-4-carbonyl] of hydrazinecarbothioic acid N-methylamide (100 mg, 0.22 mmol) was added to 1N of aqueous NaOH solution (1 mL) and refluxed for 1 h. The pH was adjusted to 7 with 1 N HCl. Upon neutralization a white solid precipitated. The desired product (40 mg) was isolated from the mixture by filtration LC/MS (Method A) [5.69 min; 428(M+1)].

Example 9

5-[3-(2-Fluoro-4-iodo-phenylamino)-pyridin-4-yl]-4-(2-morpholin-4-yl-ethyl)-[1,2,4]triazolidine-3-thione

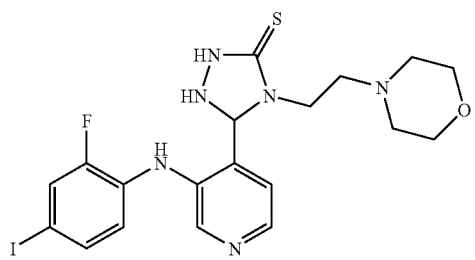

3-(2-Fluoro-4-iodo-phenylamino)-isonicotinic acid N'-(2-Morpholin-4-yl-ethyl)-thiourea-Hydrazide (100 mg, 0.22 mmol) was added to 1N aqueous NaOH solution (1 mL), and refluxed for 1 h. The pH was adjusted to 7 with 1N HCl. Upon neutralization a white solid precipitated. The desired product (45 mg) was isolated from the mixture by filtration. LC/MS (Method A) [5.13 min; 527(M+1)]

Example 10

(4-{5-[(2,2-Dimethyl-[1,3]dioxolan-4-ylmethyl)-amino]-[1,3,4]oxadiazol-2-yl}-pyridin-3-yl)-(2-fluoro-4-iodo-phenyl)-amine

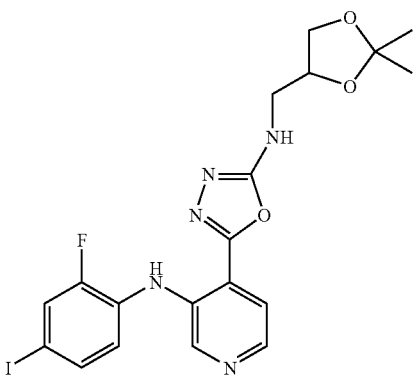

To a solution of 3-(2-Fluoro-4-iodo-phenylamino)-isonicotinic N-(2,2-Dimethyl-[1,3]dioxolan-4-yl)-formamide acidl-hydrazide (189 mg, 0.36 mmol) in DMA (2 mL) added PS-Triphenyl-phosphane (375 mg, 1.43 mmol) Trichloroacetonitrile (104 mg, 0.72 mmol) and DIEPA (0.19 mL, 1.43 mmol). The reaction mixture was stirred at 100° C. for 4 hrs. After filtration, the solution was directly subjected to preparative HPLC for purification to afford the product (130 mg). LC/MS (Method A) [5.25 min; 512(M+1)].

Example 11

3-{5-[3-(2-Fluoro-4-iodo-phenylamino)-pyridin-4-yl]-[1,3,4]oxadiazol-2-ylamino}-propane-1,2-diol

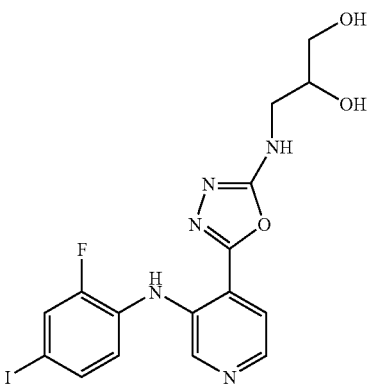

(4-{5-[(2,2-Dimethyl-[1,3]dioxolan-4-ylmethyl)-amino]-[1,3,4]oxadiazol-2-yl}-pyridin-3-yl)-(2-fluoro-4-iodo-phenyl)-amine (100 mg, 0.2 mmol) was dissolved in dichloromethane (5 mL) and TFA (3 mL) was added. The reaction mixture was stirred at RT for 4 hrs. The solvent was evaporated, and the residue was dissolved in Ethyl acetate, and washed with 1N aqueous NaOH. After solvent evaporation a residue was collected and dissolved in methanol. The product crystallized out the methanolic solution and filtered (63 mg). LC/MS (Method A) [6.61 min; 472(M+1)].

Example 12

(2-Fluoro-4-iodo-phenyl)-{4-[5-(2-morpholin-4-yl-ethylamino)-[1,3,4]thiadiazol-2-yl]-pyridin-3-yl}-amine

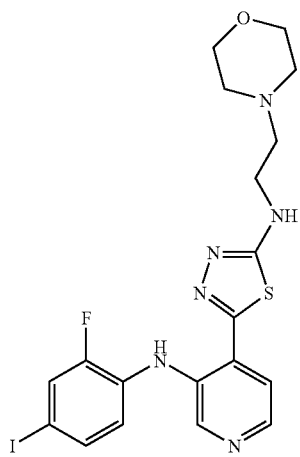

To a solution of 3-(2-Fluoro-4-iodo-phenylamino)-isonicotinic acid N'-(2-Morpholin-4-yl-ethyl)-thioureahydrazide (200 mg, 0.34 mmol) in DMA (2 mL) PS-Triphenyl-phosphane (385 mmol, 1.47 mmol) Trichloro-acetonitrile (106 mg, 0.73 mmol) DIEPA (0.19 mL, 0.76 mmol) were added. The reaction mixture was stirred at 100° C. for 4 hrs and then filtered, and the solvent was removed. The crude product was purified by preparative HPLC to afford 51 mg of pure product. LC/MS (Method A) [6.06 min; 527(M+1)].

Example 13

(2-Fluoro-4-iodo-phenyl)-[4-(5-methyl-[1,3,4]oxadiazol-2-yl)-pyridin-3-yl]-amine

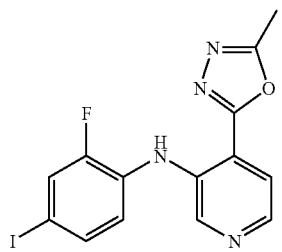

A mixture of 3-(2-Fluoro-4-iodo-phenylamino)-isonicotinic acid (200 mg, 0.54 mmol), acetic acid (32 mg, 0.54 mmol), PS-Triphenyl-phosphine (845 mg, 3.22 mmol) Trichloroacetonitrile (155 mg, 1.07 mmol) and DIEPA (0.23 mL, 1.34 mmol) in acetonitrile was stirred in a sealed tube at 100° C. for 6 hrs. The mixture was then filtered, and the filtrate was directly subjected to preparative HPLC to afford 55 mg of the desired product. LC/MS (Method A) [6.63 min; 397(M+1)].

Example 14

[4-(5-Amino-[1,3,4]oxadiazol-2-yl)-pyridin-3-yl]-(2,4-dibromo-phenyl)-amine

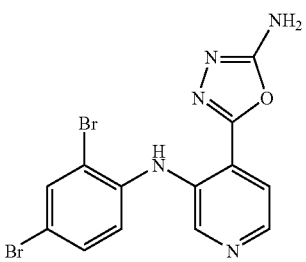

To a solution of 3-(2,4-Dibromo-phenylamino)-isonicotinic acid hydrazide (200 mg, 0.52 mmol) in DMSO (2 mL) C-(Di-imidazol-1-yl)-methyleneamine (167 mg, 1.04 mmol) was added. The reaction mixture was stirred at RT under Argon overnight, then poured into water. A solid precipitated out, which was filtered, and washed with methanol to afford the desired product (100 mg). LC/MS (Method A) [5.23 min; 412(M+1)].

Example 15

N-{5-[3-(2-Fluoro-4-iodo-phenylamino)-pyridin-4-yl]-[1,3,4]oxadiazol-2-yl}-oxalamic acid ethyl ester

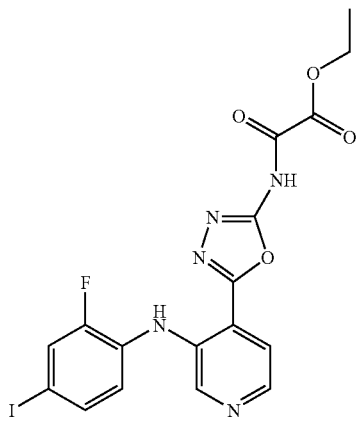

To a solution of [4-(5-Amino-[1,3,4]oxadiazol-2-yl)-pyridin-3-yl]-(2-fluoro-4-iodo-phenyl)-amine (470 mg, 1.18 mmol, 1.00 eq) in DCM (50 mL) Ethyl-diisopropyl-amine (0.72 mL; 4.14 mmol; 3.5 eq), was added and then ethyl chloro (oxo) acetate (0.2 mL; 1.78 mmol, 1.50 eq) was added dropwise at 0° C., under Argon. The reaction mixture was allowed to warm up to room temperature while stirring overnight. The mixture was then diluted with DMC (50 mL), and washed first with 5% aqueous NaHCO$_3$, and then with brine. The organic layer was dried over anhydrous MgSO$_4$, filtered, and the solvent was evaporated to afford a residue which was subjected to silica gel column chromatography using DCM:

MeOH 50:1 as eluent, to afford 220 mg of the desired product. LC/MS (Method A) [5.41 min; 498(M+1)]

Example 16

(2-Fluoro-4-iodo-phenyl)-[4-(5-methylamino-[1,3,4]oxadiazol-2-yl)-pyridin-3-yl]-amine

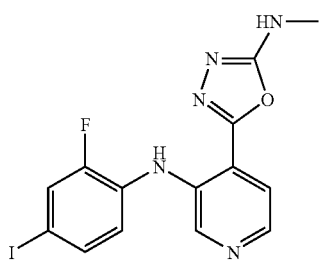

To a solution of 3-(2-Fluoro-4-iodo-phenylamino)-isonicotinic acid N'-acetyl-hydrazide (400 mg; 0.93 mmol; 1 eq) in DMA (5 mL), PS-Triphenyl-phosphine (1.22 g; 4.66 mmol; 5 eq), Trichloro-acetonitrile (269 mg; 1.86 mmol; 2 eq) and DIEPA (0.49 mL; 2.8 mmol; 3 eq) were added. The reaction mixture was stirred at 100° C. for 4 hrs. The mixture was filtered and the solution was subjected to preparative HPLC to afford the product (98 mg). LC/MS (Method A) [5.03 min; 412(M+1)]

Example 17

(3-{5-[3-(2-Fluoro-4-iodo-phenylamino)-pyridin-4-yl]-[1,3,4]oxadiazol-2-yl}-ureido)-acetic acid ethyl-ester

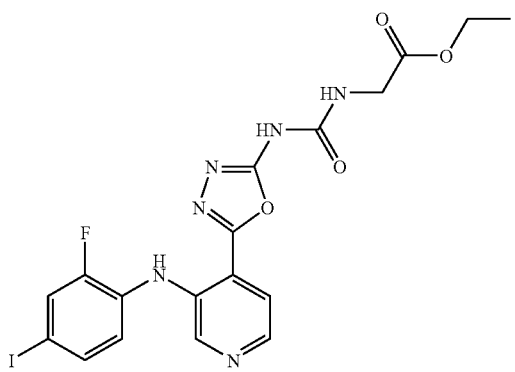

A suspension of [4-(5-Amino-[1,3,4]oxadiazol-2-yl)-pyridin-3-yl]-(2-fluoro-4-iodo-phenyl)-amine (0.200 g, 0.504 mmol) in dry THF (3 mL) was treated with ethyl isocyanatoacetate (0.077 g, 0.596 mmol). The reaction mixture was stirred at RT overnight. More isocyanatoacetate (0.083 g, 0.643 mmol) was added, and the mixture was stirred for another 72 hrs. The material was diluted with diethyl ether (2 mL), filtered and dried under high vacuum for 2 h to afford a yellow solid product (0.144 g, 0.274 mmol, 54%) LC/MS (Method A) [5.53 min; 527(M+1)]

Example 18

(2-Fluoro-4-iodo-phenyl)-{4-[5-(2-piperidin-1-yl-ethylamino)-[1,3,4]oxadiazol-2-yl]-pyridin-3-yl}-amine

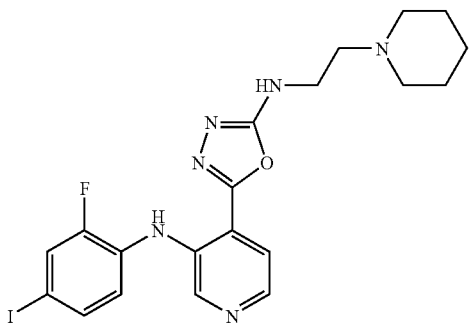

To a solution of 3-(2-Fluoro-4-iodo-phenylamino)-isonicotinic acid hydrazide (300 mg; 0.81 mmol; 1 eq) in DCM (5 mL), 1-(2-Isothiocyanato-ethyl)-piperidine (192 mg; 1.13 mmol; 1.4 eq) was added. The reaction mixture was refluxed for 4 hrs under argon. A yellow solid precipitated out and filtered to afford an intermediated that was suspended in ethanol (5 mL). Iodomethane (148 mg; 1.05 mmol; 1.3 eq) was added to the reaction mixture and stirred overnight at RT, then heated to 80° C. and stirred for another 2 hr. The mixture was filtered to give a yellow solid product 40 mg. LC/MS (Method A) [3.89 min; 509(M+1)]

Example 19

(2-Fluoro-4-iodo-phenyl)-{4-[5-(3-morpholin-4-yl-propylamino)-[1,3,4]oxadiazol-2-yl]-pyridin-3-yl}-amine

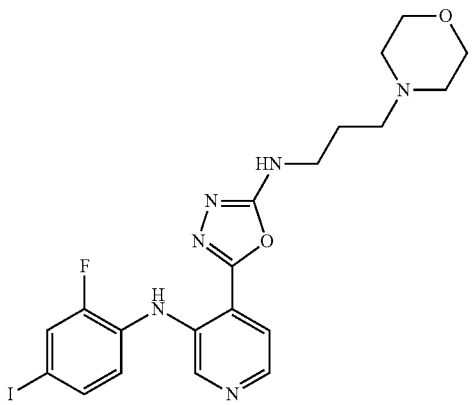

To a solution of 3-(2-Fluoro-4-iodo-phenylamino)-isonicotinic acid hydrazide (500 mg; 1.34 mmol; 1 eq) in DCM (5 mL) 4-(3-Isothiocyanato-propyl)-morpholine (300 mg; 1.61 mmol; 1.2 eq) was added. The reaction mixture was refluxed for 4 hrs under argon. A yellow solid precipitated out, which was filtered to afford an intermediate that was suspended in ethanol (5 mL). Iodomethane (190 mg; 1.34 mmol; 1.0 eq) was then added and the reaction mixture was stirred overnight at RT. It was then heated to 80° C. and stirred for another 2 hr. Filtration afforded the yellow solid product (128 mg). LC/MS (Method A) [3.73 min; 525(M+1)]

Example 20

(2-Fluoro-4-iodo-phenyl)-{4-[5-(2-morpholin-4-yl-ethylamino)-[1,3,4]oxadiazol-2-yl]-pyridin-3-yl}-amine

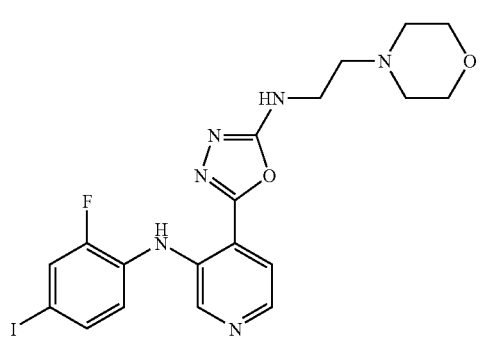

To a solution of 3-(2-Fluoro-4-iodo-phenylamino)-isonicotinic acid hydrazide (500 mg; 1.34 mmol; 1 eq) in DCM (5 mL) 4-(3-Isothiocyanato-ethyll)-morpholine (255 mg; 1.61 mmol; 1.2 eq) was added. The reaction mixture was refluxed for 4 hrs under argon. A yellow solid precipitated out, which was filtered to afford an intermediate that was suspended in ethanol (5 mL). Iodomethane (190 mg; 1.34 mmol; 1.0 eq) was then added and the reaction mixture was stirred overnight at RT. It was then heated to 80° C. and stirred for another 2 hr. Filtration afforded the yellow solid product 153 mg. LC/MS (Method A) [0.41 min; 511(M+1)]

Example 21

N-{5-[3-(2-Fluoro-4-iodo-phenylamino)-pyridin-4-yl]-[1,3,4]oxadiazol-2-yl}-acetamide

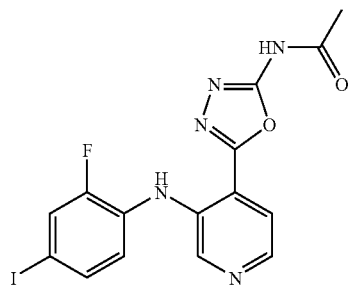

To a solution of 3-(2-Fluoro-4-iodo-phenylamino)-isonicotinic acid hydrazide (250 mg; 0.67 mmol; 1 eq) in DCM (5 mL) Acetyl isothiocyanate (80 mg; 0.8 mmol; 1.2 eq) was added. The reaction mixture was refluxed for 4 hrs under argon. A yellow solid precipitated out, which was filtered to afford an intermediate that was suspended in ethanol (5 mL). Iodomethane (95 mg; 0.67 mmol; 1.0 eq) was then added and the reaction mixture was stirred overnight at RT. It was then heated to 80° C. and stirred for another 2 hr. Filtration afforded the yellow solid product 89 mg. LC/MS (Method A) [5.30 min; 440(M+1)]

Example 22

N-{5-[3-(2-Fluoro-4-iodo-phenylamino)-pyridin-4-yl]-[1,3,4]oxadiazol-2-yl}-N',N'-dimethyl-ethane-1,2-diamine

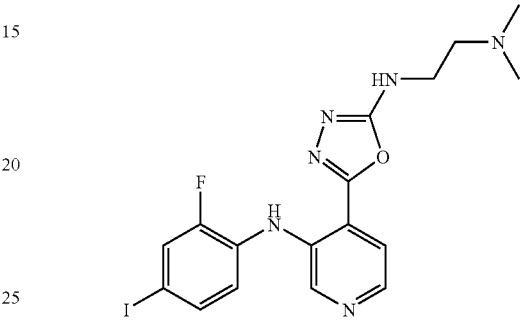

3-(2-Fluoro-4-iodo-phenylamino)-isonicotinic acid N'-(3-dimethylamino-propionyl)-hydrazide (130 mg, 0.27 mmol) was dissolved in DMA (2 mL), and then PS-Triphenyl-phosphane (420 mg, 1.6 mmol, 6 eq), Trichloro-acetonitrile (77 mg, 0.53 mmol, 2 eq) and DIEPA (0.19 mL, 1.07 mmol, 4 eq) were added. The reaction mixture was stirred at 100° C. overnight, and then filtered. The filtrate was directly subjected to preparative HPLC to afford 32 mg of the desired product. LC/MS (Method A) [3.63 min; 467(M+1)]

Example 23

(2-Fluoro-4-iodo-phenyl)-{4-[5-(2-pyrrolidin-1-yl-ethylamino)-[1,3,4]oxadiazol-2-yl]-pyridin-3-yl}-amine

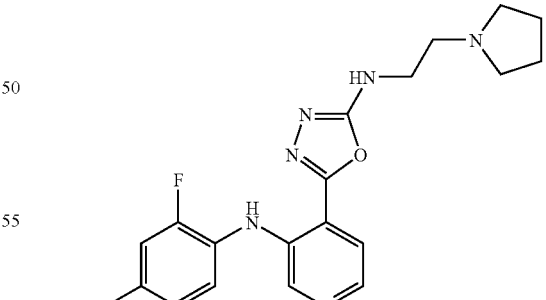

3-(2-Fluoro-4-iodo-phenylamino)-isonicotinic acid N'-(3-pyrrolidin-1-yl-propionyl)-hydrazide (138 mg, 0.27 mmol) was dissolved in DMA (2 mL), and then PS-Triphenyl-phosphane (424 mg, 1.62 mmol, 6 eq) Trichloro-acetonitrile (78 mg, 0.54 mmol, 2eq) and DIEPA (0.19 mL, 1.08 mmol, 4 eq) were added. The reaction mixture was stirred at 100° C. overnight, and then filtered. The filtrate was directly subjected to preparative HPLC to afford 26 mg of the desired product. LC/MS (Method A) [4.20 min; 495(M+1)]

Example 24

[4-(5-Amino-[1,3,4]oxadiazol-2-yl)-pyridin-3-yl]-(2-chloro-4-iodo-phenyl)-amine

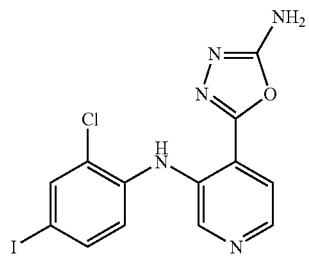

To a solution of 3-(2-Chloro-4-iodo-phenylamino)-isonicotinic acid hydrazide (150 mg, 0.39 mmol, 1 eq), in DMSO (2 mL) C-(Di-imidazol-1-yl)-methyleneamine (124 mg, 0.77 mmol, 2 eq) was added. The reaction mixture was stirred at RT under argon overnight and then poured into water. The product was isolated by filtration (135 mg). LC/MS (Method A) [5.22 min; 414(M+1)]

Example 25

[4-(5-Amino-[1,3,4]oxadiazol-2-yl)-pyridin-3-yl]-(2-fluoro-4-methoxy-phenyl)-amine

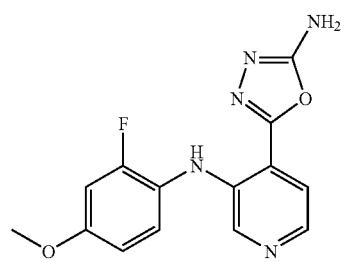

To a solution of 3-(2-Fluoro-4-methoxy-phenylamino)-isonicotinic acid hydrazide (150 mg, 0.54 mmol, 1 eq) in DMSO (2 mL) C-(Di-imidazol-1-yl)-methyleneamine (175 mg, 1.09 mmol, 2 eq) was added. The reaction mixture was stirred at RT under argon overnight and then poured into water. The product was isolated by filtration (89 mg). LC/MS (Method A) [0.52 min; 302(M+1)]

Example 26

{5-[3-(2-Fluoro-4-iodo-phenylamino)-pyridin-4-yl]-[1,3,4]oxadiazol-2-yl}-carbamic acid ethyl ester

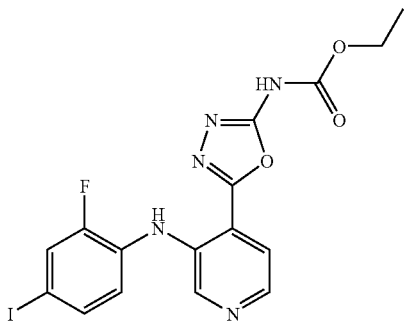

To a solution of 3-(2-Fluoro-4-iodo-phenylamino)-isonicotinic acid hydrazide (500 mg; 1.34 mmol; 1 eq) in DCM (5 mL) Isothiocyanatoethylester (2.0 g; 5.37 mmol; 1.1 eq) was added. The reaction mixture was refluxed for 4 hrs under argon. A yellow solid precipitated out that was filtered out and suspended in ethanol (20 mL). Iodomethane (0.35 mL; 5.64 mmol; 1.05 eq) was added and the reaction mixture was first stirred overnight at RT, and then heated to 80° C. while stirring for 2 hr. The product was filtered out of the mixture (1.1 g). LC/MS (Method A) [5.33 min; 470(M+1)]

Example 27

[4-(5-Amino-[1,3,4]oxadiazol-2-yl)-1-oxy-pyridin-3-yl]-(2-fluoro-4-iodo-phenyl)-amine

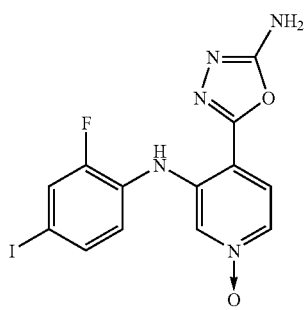

To a solution of 3-(2-Fluoro-4-iodo-phenylamino)-1-oxy-isonicotinic acid hydrazide (150 mg, 0.39 mmol, 1 eq) in DMSO (2 mL) C-(Di-imidazol-1-yl)-methyleneamine (124 mg, 0.78 mmol, 2 eq) was added. The reaction mixture was stirred at RT under argon overnight and then poured into water. The product was isolated by filtration (80 mg). LC/MS (Method A) [4.68 min; 414(M+1)]

Example 28

[4-(5-Amino-[1,3,4]oxadiazol-2-yl)-6-ethynyl-pyridin-3-yl]-(2-fluoro-4-iodo-phenyl)-amine

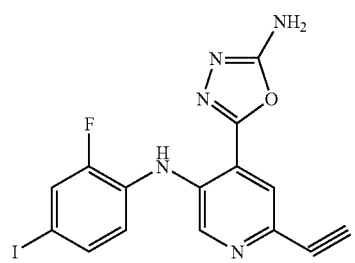

To a solution of 2-Ethynyl-5-(2-fluoro-4-iodo-phenylamino)-isonicotinic acid hydrazide (124 mg, 0.31 mmol, 1 eq) in DMSO (2 mL) C-(Di-imidazol-1-yl)-methyleneamine (101 mg, 0.63 mmol, 2 eq) was added. The reaction mixture was stirred at RT under argon overnight. and then poured into water. The solid fomed was isolated by filtration and washed with methanol to afford the product (30 mg). LC/MS (Method A) [5.15 min; 422(M+1)]

Example 29

[4-(5-Amino-[1,3,4]oxadiazol-2-yl)-pyridin-3-yl]-(4-iodo-2-methyl-phenyl)-amine

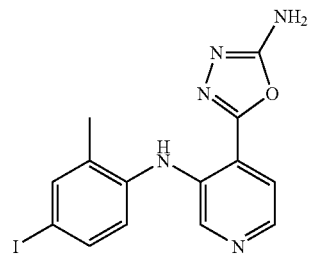

To a solution of 3-(4-Iodo-2-methyl-phenylamino)-isonicotinic acid hydrazide (200 mg, 0.54 mmol, 1 eq) in DMSO (2 mL) C-(Di-imidazol-1-yl)-methyleneamine (175 mg, 1.09 mmol, 2 eq) was added. The reaction mixture was stirred at RT under argon overnight. and then poured into water. The solid fomed was isolated by filtration and washed with methanol to afford the product 1 (45 mg). LC/MS (Method A) [4.90 min; 394(M+1)]

Example 30

[4-(5-Ethoxy-4H-[1,2,4]triazol-3-yl)-pyridin-3-yl]-(2-fluoro-4-iodo-phenyl)-amine

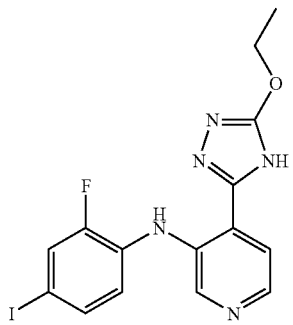

To a solution of [4-(5-Amino-[1,3,4]oxadiazol-2-yl)-pyridin-3-yl]-(2-floro-4-iodo-phenyl)-amine (150 mg, 0.38 mmol) in ethanol (10 mL) KOH 9212 mg, 3.78 mmol) was added. The reaction mixture was refluxed for 3 hrs. Then, added acetic acid was added to bring the pH to 5. The volatives were stripped and the residue was dissolved in EtOAc, and washed with 5% Na$_2$CO$_3$, and brine, and then dried over anhydrous MgSO$_4$. After filtration and solvent removal the remaining crude product was subjected to silica gel column chromatography (eluent:Hex:ane EtOAc=1:1) to afford the desired product (45 mg). [5.08 min; 394(M+1)]

Example 31

5-[3-(2-Fluoro-4-iodo-phenylamino)-pyridin-4-yl]-4H-[1,2,4]triazole-3-carboxylic acid ethyl ester

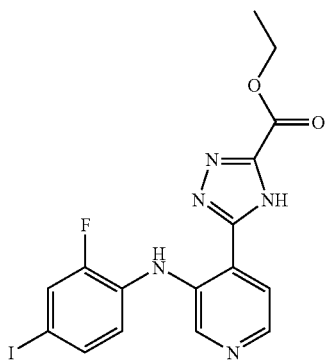

Amino-{[3-(2-fluoro-4-iodo-phenylamino)-pyridine-4-carbonyl]-hydrazono}-acetic acid ethyl ester (1.6 g, 3.4 mmo) in pyridine (10 mL) was stirred at 140° C. for 3 hrs. Cooled, poured into water, Extracted with EtOAc, Combined the organic layer, and washed with Brine, dried over MgSO$_4$, filtered, removed off solvent, got crude product, which was subjected to silica gel column (Hex:EtOAc=1:1). Collected final product 1.02 g. [5.23 min, 454 (M+1)]

Example 32

{5-[3-(2-Fluoro-4-iodo-phenylamino)-pyridin-4-yl]-4H-[1,2,4]triazol-3-yl}-methanol

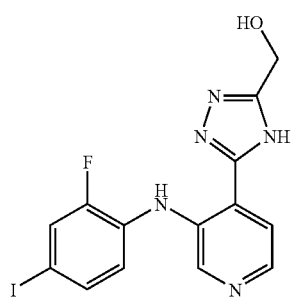

To a solution of 5-[3-(2-Fluoro-4-iodo-phenylamino)-pyridin-4-yl]-4H-[1,2,4]triazole-3-carboxylic acid ethyl ester (150 mg, 0.33 mmol, 1 eq) in THF (3 mL) LiBH4 (10.8 mg, 0.5 mmol, 1.5 eq) was added. The reaction mixture was stirred overnight at RT. The solvent was evaporated and the residue was dissolved in EtOAc, washed with brine, and dried over MgSO$_4$. After filtration and solvent removal, the crude product was purified by preparative HPLC, to afford the desired product (41 mg). [5.57 min; 454 (M+1)]

Example 33

[4-(5-Amino-4H-[1,2,4]triazol-3-yl)-pyridin-3-yl]-(4-iodo-2-methyl-phenyl)-amine

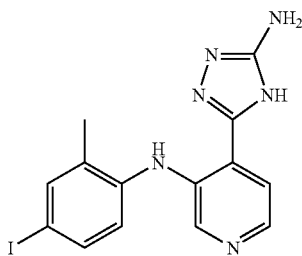

A reaction mixture of 3-(4-Iodo-2-methyl-phenylamino)-isonicotinic acid hydrazide (120 mg, 0.33 mmol, 1 eq) and C-Methylsulfanyl-methanediamine hydroiodide (104 mg, 0.47 mL, 1.45 eq) in pyridine (2 mL) in sealed tube was heated to 140° C. while stirring for 4 hrs. After cooling, it was poured into water, extracted with EtOAc, and the combined organic fractions, dried over anhydrous MgSO$_4$. After filtration and solvent removal the remaining crude product was subjected to silica gel column chromatography (eluent:Hexane EtOAc=1:1) to afford the desired product (35 mg). [4.26 min; 393(M+1)]

Example 34

[4-(5-Amino-[1,3,4]oxadiazol-2-yl)-pyridin-3-yl]-(4-bromo-2-fluoro-phenyl)-amine

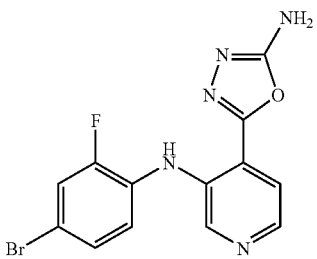

To a solution of 3-(4-Bromo-2-fluoro-phenylamino)-isonicotinic acid hydrazide (200 mg, 0.62 mmol, 1 eq) in DMSO (2 mL) C-(Di-imidazol-1-yl)-methyleneamine (198 mg, 1.23 mmol, 2 eq) was added. The reaction mixture was stirred at RT under argon overnight. It was then poured into water and the solid that precipitated out was filtered and washed with methanol to afford the desired product (195 mg). LC/MS (Method A) [0.62 min; 351(M+1)]

Example 35

[4-(5-Amino-[1,3,4]oxadiazol-2-yl)-pyridin-3-yl]-(4-bromo-2-chloro-phenyl)-amine

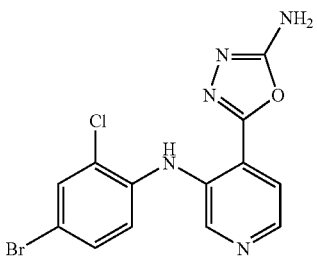

To a solution of 3-(4-Bromo-2-chloro-phenylamino)-isonicotinic acid hydrazide (200 mg, 0.59 mmol, 1 eq) in DMSO (2 mL) C-(Di-imidazol-1-yl)-methyleneamine (188 mg, 1.17 mmol, 2 eq) was added. The reaction mixture was stirred at RT under argon overnight and then poured into water. A solid precipitated out that was filtered and washed with methanol to give the desired product (125 mg). LC/MS (Method A) [4.77 min; 367(M+1)]

Example 36

5-[3-(2-Fluoro-4-iodo-phenylamino)-pyridin-4-yl]-[1,2,4]oxadiazole-3-carboxylic acid ethyl ester

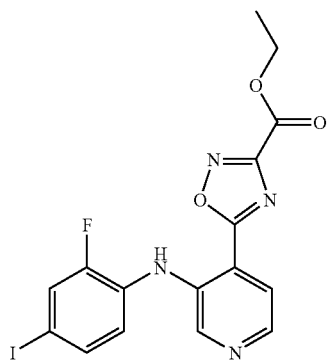

A reaction mixture of 3-(2-Fluoro-4-iodo-phenylamino)-isonicotinic acid (1000 mg, 2.79 mmol, 1.00 eq), and Di-imidazol-1-yl-methanone ((543 mg, 3.35 mmol, 1.20 eq) in DMF was stirred for 4 hrs at RT under argon. Then hydroxyamino-imino-acetic acid ethyl ester (612 mg, 4.19 mmol, 1.5 eq.) was added and the reaction mixture was stirred overnight, and then diluted with water. A yellow precipitate was formed that was filtered to afford the product (785 mg). [5.46 min; 455 (M+1)]

Example 37

(2-Fluoro-4-iodo-phenyl)-(4-[1,2,4]oxadiazol-5-yl-pyridin-3-yl)-amine

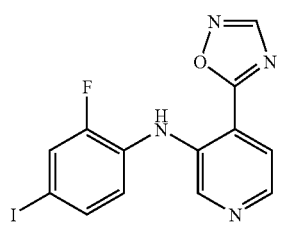

To a solution of 5-[3-(2-Fluoro-4-iodo-phenylamino)-pyridin-4-yl]-[1,2,4]oxadiazole-3-carboxylic acid ethyl ester (1.8 g, 3.96 mmol) in THF-H2O (1:1)(20 mL) LiOH (0.19 g, 7.93 mmL) was added. The reaction mixture was stirred for 2 hrs at RT. The pH was adjusted to 5 with 1N HCl and the mixture was diluted with water. A solid precipitated and was filtered to give the product (1.4 g). LC/MS (Method A) [4.39 min; 383(M+1)]

Example 38

{5-[3-(2-Fluoro-4-iodo-phenylamino)-pyridin-4-yl]-[1,2,4]oxadiazol-3-yl}-methanol

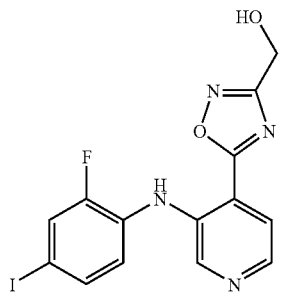

To a solution of 5-[3-(2-Fluoro-4-iodo-phenylamino)-pyridin-4-yl]-[1,2,4]oxadiazole-3-carboxylic acid ethyl ester (768 mg, 1.69 mmL, 1 eq) in THF (6 mL) LiBH$_4$ (55 mg, 2.54 mmol, 1.5 eq) was added. The reaction mixture was stirred overnight and the solvent was evaporated. The residue was dissolved in EtOAc, washed with brine, and dried with anhydrous MgSO$_4$. Filtration and removal of the solvent afforded the crude product which was subjected to silica gel column chromatography (eluent:CH$_2$Cl$_2$:MeOH 70:1) to give rise to pure product (497 mg). [5.01 min; 413 (M+1)]

Example 39

5-[3-(2-Fluoro-4-iodo-phenylamino)-pyridin-4-yl]-[1,3,4]oxadiazole-2-carboxylic acid ethyl ester

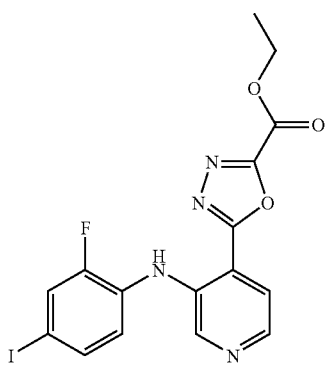

To a solution of {N'-[3-(2-Fluoro-4-iodo-phenylamino)-pyridine-4-carbonyl]-hydrazino}-oxo-acetic acid ethyl ester (1.27 g, 2.69 mmol, 1.0 eq.) in DCM (20 mL) containing pyridine (0.55 g, 6.99 mmol. 2.66 eq.) thionyl dichloride (0.26 mL, 3.5 mmol; 1.30 eq) was added at 0° C. The reaction mixture were stirred at 0° C. for 2 hrs. The solvent was evaporated, toluene was added and the reaction mixture was stirred at 110° C. for 6 hrs. Removal of the solvent resulted in a residue that was subjected to silica gel column chromatography (EtOAc:Hex=1:2) to afford the desired product (0.50 g). [5.32 min; 455 (M+1)]

Example 40

(2-Fluoro-4-iodo-phenyl)-(4-[1,3,4]oxadiazol-2-yl-pyridin-3-yl)-amine

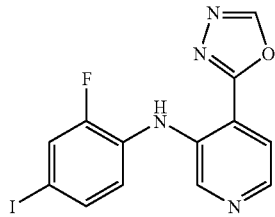

To a solution of 5-[3-(2-Fluoro-4-iodo-phenylamino)-pyridin-4-yl]-[1,3,4]oxadiazole-2-carboxylic acid ethyl ester (200 mg, 0.44 mmol) in THF-H2O (1:1) (5 mL) LiOH (32 mg, 1.32 mmol) was added. The reaction mixture was stirred for 2 hrs and then the pH was adjusted to 5 with 1N HCl. Upon dilution with water a solid precipitated. Filtration afforded the desired product (89 mg). LC/MS (Method A) [0.48 min; 383(M+1)]

Example 41

[4-(5-Amino-4H-[1,2,4]triazol-3-yl)-pyridin-3-yl]-(2-fluoro-4-iodo-phenyl)-amine

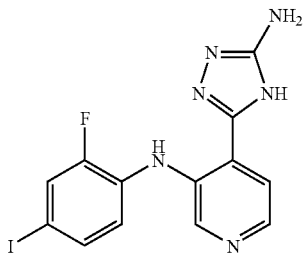

A reaction mixture of 3-(2-Fluoro-4-iodo-phenylamino)-isonicotinic acid hydrazide (100 mg, 0.27 mmol, 1 eq) and C-Methylsulfanyl-methanediamine hydroiodide (86 mg, 0.39 mmol, 1.45 eq) in pyridine (2 mL) in a sealed tube was heated at 140° C. for 4 hrs. After cooling the mixture was poured into water, extracted with EtOAc, and the combined organic fractions were dried over anhydrous MgSO4. After filtration and solvent evaporation the resulting residue was subjected to silica gel column chromatography (EtOAC:Hex=1:1) to give the desired product (46 mg). [4.99 min; 397(M+1)]

Example 42

[4-(5-Dimethylamino-[1,3,4]oxadiazol-2-yl)-pyridin-3-yl]-(2-fluoro-4-iodo-phenyl)-amine

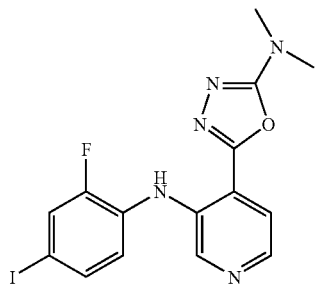

To a solution of 3-(2-Fluoro-4-iodo-phenylamino)-isonicotinic acid N'-formamid-hydrazide (100 mg, 0.23 mmol, 1 eq) in acetonitrile, PS-Triphenyl-phosphane (236 mg, 0.9 mmol, 4 eq), Trichloro-acetonitrile (0.09 mL, 0.9 mmol, 4 eq) and DIEPA (0.16 mL, 0.9 mL, 4 eq) were added. The reaction mixture was stirred at 100 C for 4 hrs. After filtration the resulting solution was directly subjected to preparative HPLC to afford the desired product (45 mg). LC/MS (Method A) [4.70 min; 426(M+1)]

Example 43

{5-[3-(2-Fluoro-4-iodo-phenylamino)-pyridin-4-yl]-[1,3,4]oxadiazol-2-ylamino}-acetic acid methyl ester

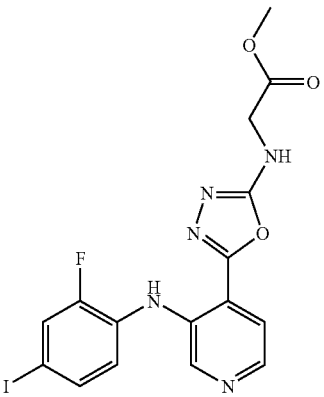

To a solution of 3-(2-Fluoro-4-iodo-phenylamino)-isonicotinic acid hydrazide (1.50 g 4.03 mmol; 1 eq) in DCM (20 mL) Isothiocyanatoethylester (0.58 g; 4.43 mmol; 1.1 eq) was added. The reaction mixture was refluxed for 4 hrs under argon. A yellow solid precipitated out and filtered to afford 2.05 g of an intermediate. 1.0 g (1.99 mmol. 1 eq) of this intermediate was suspended in ethanol (20 mL) and iodomethane (0.13 mL; 2.09 mmol; 1.05 eq) was added. The reaction mixture was stirred overnight at RT, and filtered, to isolate a solid. 100 mg (0.19 mmol) of that solid was suspended in ethanol (3 mL) and heated at 80° C. for 2 hr.

Filtration resulted in the desired product (20 mg). LC/MS (Method A) [5.09 min; 470(M+1)]

Example 44

2-{5-[3-(2-Fluoro-4-iodo-phenylamino)-pyridin-4-yl]-[1,3,4]oxadiazol-2-ylamino}-ethanol

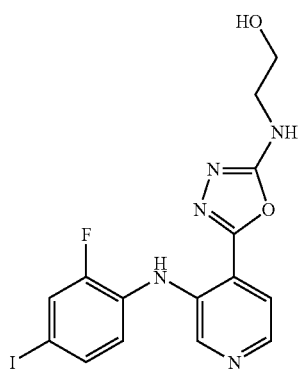

To a solution of {5-[3-(2-Fluoro-4-iodo-phenylamino)-pyridin-4-yl]-[1,3,4]oxadiazol-2-ylamino}-acetic acid methyl ester (400 mg, 0.85 mmol, 1 eq) in THF (5 mL) LiBH$_4$ (37 mg, 1.7 mmol, 2 eq) was added. The reaction mixture was stirred at RT for 20 hrs and then quenched with methanol and then added water. The solvent was partially removed and EtOAc was added. A solid precipitated out that was filtered to give the desired product (190 mg). LC/MS (Method A) [4.48 min; 442(M+1)]

Example 45

{5-[3-(2-Fluoro-4-iodo-phenylamino)-pyridin-4-yl]-[1,3,4]oxadiazol-2-ylamino}-acetic acid

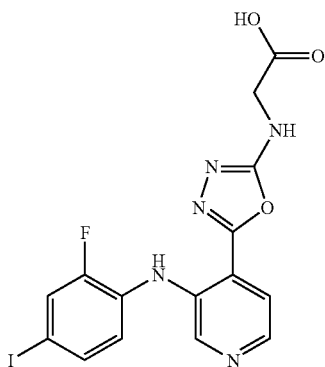

To a solution of {5-[3-(2-Fluoro-4-iodo-phenylamino)-pyridin-4-yl]-[1,3,4]oxadiazol-2-ylamino}-acetic acid methyl ester (262 mg, 0.56 mmol, 1 eq) in THF-H2O (1:1) (2 mL) LiOH (27 mg, 1.12 mmol, 2 eq) was added. The reaction mixture was stirred at RT for 2 hrs. The solvent was removed partially and more water was added. The mixture was washed with ether and the pH of the aqueous layer was adjusted to 3 with 1N HCl. A solid precipitated and filtered to afford the desired product (190 mg). LC/MS (Method A) [4.83 min; 456(M+1)]

Example 46

2-{5-[3-(2-Fluoro-4-iodo-phenylamino)-pyridin-4-yl]-[1,3,4]oxadiazol-2-ylamino}-acetamide

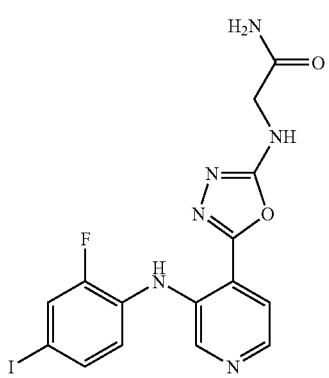

To a solution of {5-[3-(2-Fluoro-4-iodo-phenylamino)-pyridin-4-yl]-[1,3,4]oxadiazol-2-ylamino}-acetic acid (75 mg, 0.16 mmol, 1 eq) in DMF CDI (35 mg, 0.21 mmol, 1.3 eq) was added. The reaction mixture was stirred at RT under argon for 3 hrs and then amoniumacetate (30 mg, 0.41 mmol, 2.5 eq) was added. The mixture was stirred for another 2 hrs. The resulting mixture was directly purified by preparative HPLC to afford the desired product (35 mg). LC/MS (Method A) [4.57 min; 455(M+1)]

Example 47

2-{5-[3-(2-Fluoro-4-iodo-phenylamino)-pyridin-4-yl]-[1,3,4]oxadiazol-2-ylamino}-N,N-dimethyl-acetamide

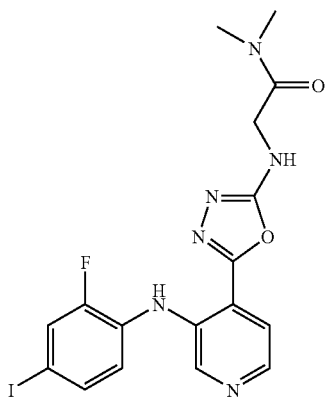

To a solution of {5-[3-(2-Fluoro-4-iodo-phenylamino)-pyridin-4-yl]-[1,3,4]oxadiazol-2-ylamino}-acetic acid (75 mg, 0.16 mmol, 1 eq) in DMF CDI (35 mg, 0.21 mmol, 1.3 eq) was added. The reaction mixture was stirred at RT under argon for 3 hrs. Then diisopropanlethylamine (352 mg, 0.41 mmol, 2.5 eq), and dimethylamine hydrichloride (40 mg, 0.41 mmol, 2.5 eq) was added and the mixture was stirred for another 2 hrs. It was then directly purified by reverse phase preparative HPLC to give the desired product (35 mg). LC/MS (Method A) [4.87 min; 483 (M+1)]

Example 48

[4-(5-Amino-[1,3,4]oxadiazol-2-yl)-5-fluoro-pyridin-3-yl]-(2-fluoro-4-iodo-phenyl)-amine

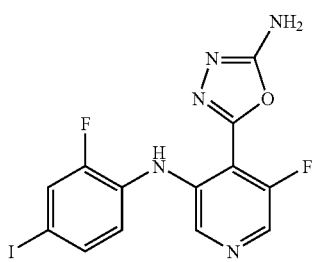

To a solution of 3-Fluoro-5-(2-fluoro-4-iodo-phenylamino)-isonicotinic acid hydrazide (100 mg 0.26 mmol, 1 eq) in DMSO (2 mL) C-(Di-imidazol-1-yl)-methyleneamine (123 mg, 0.77 mmol, 3 eq) was added. The reaction mixture was stirred at RT under argon overnight and then poured into water. A solid precipitated out that was filtered out and washed with methanol to afford the desired product (65 mg). LC/MS (Method A) [5.19 min; 416(M+1)]

Example 49

(2-Fluoro-4-iodo-phenyl)-(4-{5-[(tetrahydro-furan-2-ylmethyl)-amino]-[1,3,4]oxadiazol-2-yl}-pyridin-3-yl)-amine

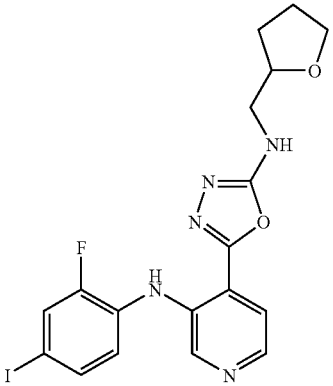

A reaction mixture of 3-(2-Fluoro-4-iodo-phenylamino)-isonicotinic acid N'-(Tetrahydro-furan-2-ylmethyl)-thiourea-hydrazide (200 mg, 0.39 mmol, 1 eq), methyliodide (0.03 mL, 0.5 mmol, 1.3 eq) and DIEPA (0.2 mL, 0.58 mmol, 1.5 eq) were stirred at RT overnight. It was then heated at 85° C. for 2 hrs. As the solvent was partially removed a solid precipitated out. It was filtered to produce the desired product (105 mg). LC/MS (Method A) [5.27 min; 482(M+1)]

Example 50

(2-Fluoro-4-iodo-phenyl)-(4-{5-[(tetrahydro-furan-2-ylmethyl)-amino]-[1,3,4]thiadiazol-2-yl}-pyridin-3-yl)-amine

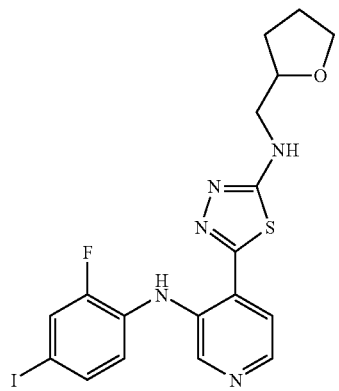

To a solution of 3-(2-Fluoro-4-iodo-phenylamino)-isonicotinic acid, N'-(Tetrahydro-furan-2-ylmethyl)-thiourea-hydrazide (260 mg, 0.50 mmol) in DMA (2 mL), PS-Triphenylphosphane (794 mg, 3.03 mmol) Trichloro-acetonitrile (146 mg, 1.01 mmol) and DIEPA (0.26 mL, 1.51 mmol) were added. The reaction mixture was stirred at 80° C. for 4 hrs and then filtered, and the solvent was removed. The residue was washed with methanol to afford the product (97 mg). LC/MS (Method A) [5.31 min; 498(M+1)]

Example 51

5-[3-(2-Fluoro-4-iodo-phenylamino)-pyridin-4-yl]-4-(tetrahydro-furan-3-ylmethyl)-2,4-dihydro-[1,2,4]triazole-3-thione

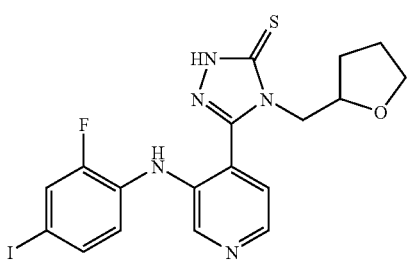

3-(2-Fluoro-4-iodo-phenylamino)-isonicotinic acid N'-(Tetrahydro-furan-2-ylmethyl)-thiourea-hydrazide (100 mg, 0.19 mmol) was treated with 1N NaOH (1 mL). The reaction mixture was heated to 110° C. in sealed tube for 2 hrs. The mixture was then neutralized with 1N HCl, filtered, and the resulting solid was washed with methanol to give the desired product (17 mg). LC/MS (Method A) [5.01 min; 498(M+1)]

Example 52

2-{5-[3-(2-Fluoro-4-iodo-phenylamino)-pyridin-4-yl]-[1,3,4]oxadiazol-2-ylamino}-propionic acid ethyl ester

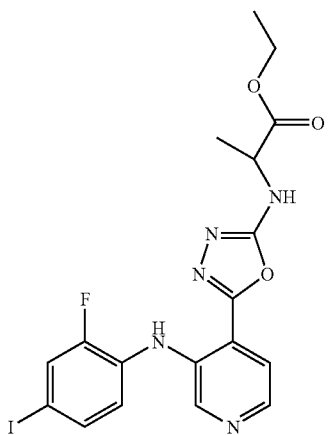

A mixture of 3-(2-Fluoro-4-iodo-phenylamino)-isonicotinic acid N'-thiocarbamic acid ethyl ester (600 mg, 1.13 mmol, 1 eq), methyliodide (0.09 mL, 1.47 mmol, 1.3 eq), and DIEPA (0.3 mL, 1.69 mmol, 1.5 eq) were stirred at RT overnight. Then it was heated at 85° C. for 2 hrs. The solvent was partially removed resulting in the precipitation of a solid that was filtered to afford the product (75 mg). LC/MS (Method A) [5.22 min; 498(M+1)]

Example 53

2-{5-[3-(2-Fluoro-4-iodo-phenylamino)-pyridin-4-yl]-[1,3,4]oxadiazol-2-ylamino}-propionic acid

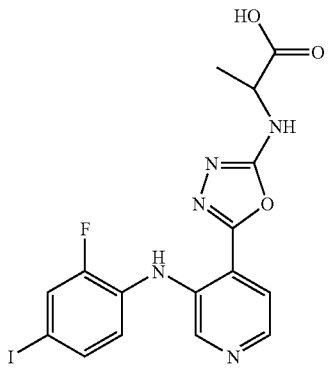

A mixture of 2-{5-[3-(2-Fluoro-4-iodo-phenylamino)-pyridin-4-yl]-[1,3,4]oxadiazol-2-ylamino}-propionic acid ethyl ester (45 mg, 0.09 mmol, 1.0 eq) and LiOH (5 mg, 0.18 mmol, 2 eq) in THF-H2O (1:1) (0.5 mL) was stirred at RT for 2 hr. The pH was adjusted to pH 5 with 1N HCl and the mixture was diluted with EtOAc, washed with brine, and dried over anhydrous MgSO$_4$. Filtration and solvent removal resulted in a residue that was washed with ether to give rise to the desired product (41 mg). LC/MS (Method A) [5.04 min; 470(M+1)]

Intermediate 4

2-(3-(2-fluoro-4-iodophenylamino)isonicotinoyl)hydrazinecarbothioamide

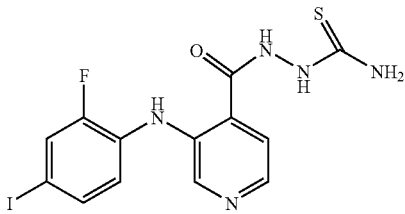

To a solution of 3-[(2-fluoro-4-iodophenyl)amino]isonicotinic acid (360 mg; 1.01 mmol) was added 1,1'-carbonylbis(1H-imidazole) (196 mg; 1.21 mmol). The mixture was stirred overnight. The dark yellow colored solution was treated with thiosemicarbazide (110 mg mg; 1.21 mmol). The reaction mixture was stirred at room temperature overnight. Water (10 mL) was added, and extracted with ethyl acetate. Concentrated and purified on Flashmaster to obtain 2-{3-[(2-fluoro-4-iodophenyl)amino]isonicotinoyl}hydrazine carbothioamide. (300 mg, 69%) MS m/z: 432 M+1

Example 54

[4-(5-Amino-[1,3,4]thiadiazol-2-yl)-pyridin-3-yl]-(2-fluoro-4-iodo-phenyl)-amine

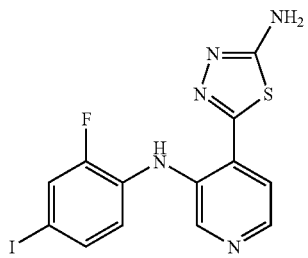

To a solution of 2-{3-[(2-fluoro-4-iodophenyl)amino]isonicotinoyl}hydrazine carbothioamide (220 mg; 0.51 mmol) in DMF (5.00 mL) were added resin bound triphenylphosphine (401 mg; 1.53 mmol), carbon tetrabromide tetrabromomethane (508 mg; 1.53 mmol), and triethyl amine (180 mg; 1.53 mmol). The mixture was heated at 50° C. for 5 h. Filtered and purified on Agilent Prep. HPLC system to get 10 mg of [4-(5-Amino-[1,3,4]thiadiazol-2-yl)-pyridin-3-yl]-(2-fluoro-4-iodo-phenyl)-amine. MS m/z: 414 M+1

Intermediate 5

2-(3-(2-fluoro-4-iodophenylamino)isonicotinoyl)-N-methylhydrazinecarboxamide

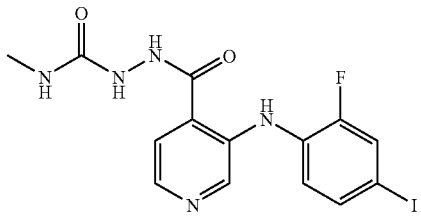

To a suspension of 3-[(2-fluoro-4-iodophenyl)amino]isonicotinohydrazide (200 mg; 0.54 mmol) in methanol (10 mL) was added (methylimino)(oxo)methane (61 mg; 1.07 mmol) (methyl Isocyanate). After few minutes the reaction mixture became homogeneous, and then an yellow colored solid, 2-{3-[(2-fluoro-4-iodophenyl)amino]isonicotinoyl}-N-methylhydrazinecarboxamide (50 mg) was separated out. The filtrate upon concentration gave 158 mg which was also pure. (208 mg, 90%) MS m/z: 429 M+1

Example 55

5-[3-(2-Fluoro-4-iodo-phenylamino)-pyridin-4-yl]-4-methyl-2,4-dihydro-[1,2,4]triazol-3-one

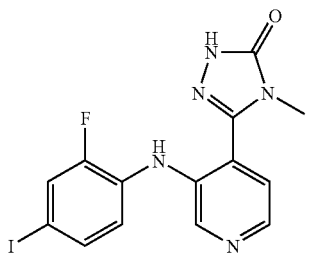

To a suspension of 2-{3-[(2-fluoro-4-iodophenyl)amino]isonicotinoyl}-N-methylhydrazinecarboxamide (165 mg; 0.38 mmol) in water (3 mL) was added 1N NaOH (3 mL). The mixture became homogeneous. The reaction mixture was heated at 120° C. for 3 days. The progress of the reaction was monitored by LCMS. Concentration of the solvent and repeated purifications gave 10 mg of 5-[3-(2-Fluoro-4-iodo-phenylamino)-pyridin-4-yl]-4-methyl-2,4-dihydro-[1,2,4]triazol-3-one Mass: MS m/z: 412 M+1

Example 56

(2-Fluoro-4-iodo-phenyl)-(4-[1,2,4]oxadiazol-3-yl-pyridin-3-yl)-amine

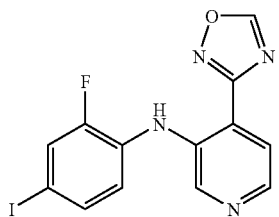

To a solution of ethyl 3-{3-[(2-fluoro-4-iodophenyl)amino]pyridin-4-yl}-1,2,4-oxadiazole-5-carboxylate (1.80 g; 3.96 mmol; 1.00 eq.) in THF-H2O (1:1) was added lithium hydroxide (0.19 g; 7.93 mmol) Stirred for 2 h at room temperature. After work up, 1.42 g of (2-Fluoro-4-iodo-phenyl)-(4-[1,2,4]oxadiazol-3-yl-pyridin-3-yl)-amine was obtained in 92% yield. MS m/z: 383 M+1

Intermediate 6

3-Bromo-5-fluoro-isonicotinic acid

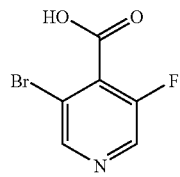

n-Butyllithium (12.5 mL, 2.5 M in THF, 31.3 mmol) was added slowly to a solution of diisopropylamine (4.4 mL, 31.3 mmol) in THF (200 mL) at 0° C., stirred for 15 minutes, and then cooled to −78° C. 3-Bromo-5-fluoro pyridine (5.0 g, 28.4 mmol) was added as a solid, and the resulting solution was stirred for 10 minutes at −78° C. Gaseous carbon dioxide was bubbled into the solution via a cannula for 30 minutes, and the resulting solution was stirred for 2 h warming from −78° C. to room temperature. The reaction solution was concentrated via rotary evaporation, diluted with 2M NaOH, and washed with EtOAc. The aqueous solution was acidified with 1 M HCl, and extracted with EtOAc. The organic extracts were washed with brine, dried over MgSO$_4$, filtered, and concentrated to afford the desired product (4.75 g, 76%) as a solid.

Intermediate 7

3-Bromo-5-(2-fluoro-phenylamino)-isonicotinic acid

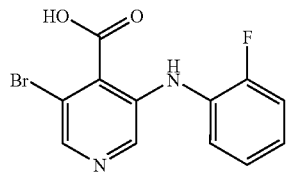

Lithium bis(trimethylsilyl)amide (54.6 mL, 1.0 M in THF, 54.6 mmol) was added to a solution of 2-fluoro aniline (3.5 mL, 36.4 mmol) in THF (100 mL) at −78° C. The resulting solution was for 1 h at −78° C. 3-Bromo-5-fluoro-isonicotinic acid (1) (4.0 g, 18.2 mmol) was added as a solid, and the reaction solution was stirred for 48 h at room temperature. The reaction solution was concentrated via rotary evaporation, diluted with satd. NaHCO$_3$, and washed with EtOAc. The aqueous solution was acidified with concentrated HCl. The resulting precipitate was filtered, washed with H$_2$O, and dried under vacuum to afford the desired product (4.2 g, 74%) as a yellow solid.

Intermediate 8

3-Bromo-5-(2-fluoro-phenylamino)-isonicotinic acid
3-Bromo-5-(2-fluoro-phenylamino)-isonicotinic acid methyl ester

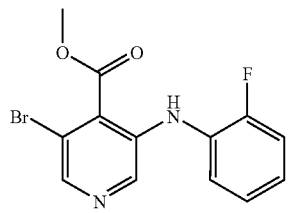

(Trimethylsilyl)diazomethane (8.1 mL, 2M in THF, 16.2 mmol) was added to a solution of 3-bromo-5-(2-fluoro-phenylamino)-isonicotinic acid (4.2 g, 13.5 mmol) in THF/MeOH (72 mL, 9/1, v/v) and stirred for 2 h at room temperature. The reaction solution was quenched with acetic acid, and then concentrated. The crude product was purified via Biotage eluting with a gradient of 0 to 50% EtOAc in hexanes to afford the desired product (4.1 g, 94%) as a yellow solid.

Intermediate 9

3-(2-Chloro-phenyl)-5-(2-fluoro-phenylamino)-isonicotinic acid methyl ester

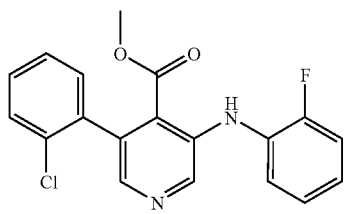

3-Bromo-5-(2-fluoro-phenylamino)-isonicotinic acid methyl ester (250 mg, 0.77 mmol), 2-chlorophenylboronic acid (0.18 g, 1.2 mmol), Pd(OAc)$_2$ (10 mg, 0.025 mmol), S-Phos (20 mg, 0.05 mmol), and K$_2$CO$_3$ (0.32 g, 2.3 mmol) were suspended in dioxane/H$_2$O (1.65 mL, 9/1, v/v) and stirred overnight at 100° C. The reaction solution was diluted with EtOAc, and filtered through an Extrelut column. The column was washed with EtOAc, and the filtrate was concentrated. The crude product was purified via Biotage eluting with a gradient of 0 to 50% EtOAc in hexanes to afford the desired product (220 mg, 80%) as a yellow oil. LC-MS (M+H=357, obsd.=357).

Intermediate 10

3-(2-Chloro-phenyl)-5-(2-fluoro-4-iodo-phenylamino)-isonicotinic acid methyl ester

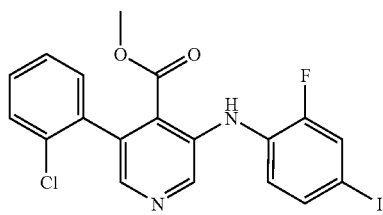

N-iodosuccinimide (236 mg, 1.05 mmol) and p-toluenesulfonic acid monohydrate (400 mg, 2.1 mmol) were added to a solution of 3-(2-chloro-phenyl)-5-(2-fluoro-phenylamino)-isonicotinic acid methyl ester (300 mg, 0.84 mmol), and stirred overnight at 60° C. The reaction mixture was quenched with Na$_2$S$_2$O$_3$ (1 mL, 10% aqueous solution), diluted with CH$_2$Cl$_2$, and filtered through an Extrelut column. The column was washed with CH$_2$Cl$_2$, and the filtrate was concentrated. The crude product was purified via Biotage eluting with a gradient of 0 to 55% EtOAc in hexanes to afford the desired product (343 mg, 85%). LC-MS (M+H=483, obsd.=483).

Intermediate 11

3-(2-Chloro-phenyl)-5-(2-fluoro-4-iodo-phenylamino)-isonicotinic acid

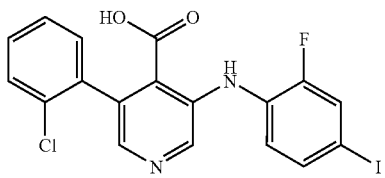

NaOH (3.6 mL, 2M solution in H₂O, 7.2 mmol) was added to a solution of 3-(2-chloro-phenyl)-5-(2-fluoro-4-iodo-phenylamino)-isonicotinic acid methyl ester (343 mg, 0.71 mmol) in MeOH (3 mL) and stirred overnight at 60° C. The MeOH was removed and the aqueous solution was acidified with concentrated HCl. The resulting precipitate was filtered, washed with H₂O, and dried under vacuum to afford the desired product (253 mg, 76%). LC-MS (M+H=469, obsd.=469).

Intermediate 12

3-(2-Chloro-phenyl)-5-(2-fluoro-4-iodo-phenylamino)-isonicotinic acid hydrazide

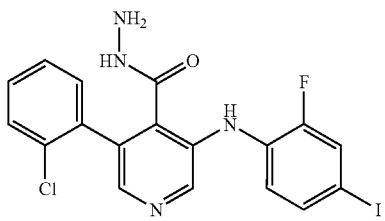

1,1'-carbonyldiimidazole (21 mg, 0.13 mmol) was added to a solution of 3-(2-chloro-phenyl)-5-(2-fluoro-4-iodo-phenylamino)-isonicotinic acid from above (40 mg, 0.09 mmol) in DMSO (1 mL), and stirred overnight at 60° C. Hydrazine hydrate (13 mg, 0.27 mmol) was added, and the reaction solution was stirred for an additional 4 h at 60° C. The reaction solution was quenched with H₂O, diluted with EtOAc, and filtered through an Extrelut column. The column was washed with EtOAc, and the filtrate was concentrated. The crude product was purified via Biotage eluting with a gradient of 0 to 70% EtOAc in hexanes to afford the desired product (17 mg, 41%). LC-MS (M+H=483, obsd.=438).

Example 57

[4-(5-Amino-[1,3,4]oxadiazol-2-yl)-5-(2-chloro-phenyl)-pyridin-3-yl]-(2-fluoro-4-iodo-phenyl)-amine

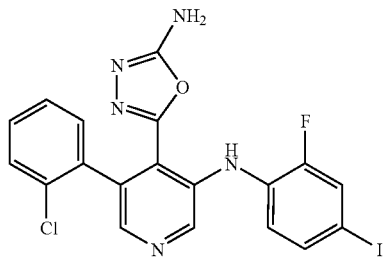

Phenyl cyanate (5 mg, 0.04 mmol) was added to a solution of 3-(2-chloro-phenyl)-5-(2-fluoro-4-iodo-phenylamino)-isonicotinic acid hydrazide (7) (17 mg, 0.04 mmol) in DMSO (1 mL), and stirred overnight at room temperature. The reaction solution was quenched with H₂O. The resulting precipitate was filtered, washed with H₂O, and dried under vacuum to afford the desired product (5 mg, 28%). LC-MS (M+H=508, obsd.=508). ¹H NMR: δ 8.92 (s, 1H), 8.47 (d, 1H), 8.03 (d, 1H), 7.74 (dd, 1H), 7.55 (m, 2H), 7.43 (m, 3H), 7.24 (t, 1H), 7.11 (s, 2H).

Intermediate 13

3-(2-Fluoro-phenyl)-5-(2-fluoro-phenylamino)-isonicotinic acid methyl ester

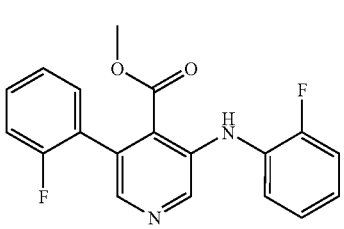

3-Bromo-5-(2-fluoro-phenylamino)-isonicotinic acid methyl ester (1.25 g, 3.84 mmol), 2-fluorophenylboronic acid (0.81 g, 5.77 mmol), Pd(OAc)₂ (30 mg, 0.12 mmol), S-Phos (90 mg, 0.24 mmol), and K₂CO₃ (1.6 g, 11.5 mmol) were suspended in dioxane/H₂O (9 mL, 9/1, v/v) and stirred overnight at 100° C. The reaction solution was diluted with EtOAc, and filtered through an Extrelut column. The column was washed with EtOAc, and the filtrate was concentrated. The crude product was purified via Biotage eluting with a gradient of 0 to 50% EtOAc in hexanes to afford the desired product (680 mg, 52%) as a yellow solid. LC-MS (M+H=341, obsd.=341).

Intermediate 14

3-(2-Fluoro-phenyl)-5-(2-fluoro-4-iodo-phenylamino)-isonicotinic acid methyl ester

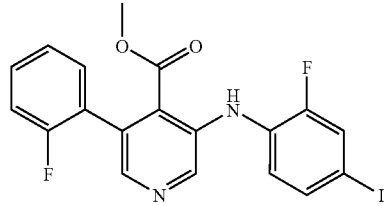

N-iodosuccinimide (400 mg, 1.76 mmol) and p-toluenesulfonic acid monohydrate (670 mg, 3.53 mmol) were added to a solution of 3-(2-fluoro-phenyl)-5-(2-fluoro-phenylamino)-isonicotinic acid methyl ester (480 mg, 1.41 mmol), and stirred overnight at 60° C. The reaction mixture was quenched with $Na_2S_2O_3$ (1 mL, 10% aqueous solution), diluted with $CH_2Cl_2$, and filtered through an Extrelut column. The column was washed with $CH_2Cl_2$, and the filtrate was concentrated. The crude product was purified via Biotage eluting with a gradient of 0 to 55% EtOAc in hexanes to afford the desired product (516 mg, 78%). LC-MS (M+H=467, obsd.=467).

Intermediate 15

3-(2-Fluoro-phenyl)-5-(2-fluoro-4-iodo-phenylamino)-isonicotinic acid

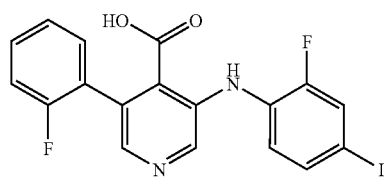

NaOH (3.2 mL, 2M solution in $H_2O$, 6.4 mmol) was added to a solution of 3-(2-fluoro-phenyl)-5-(2-fluoro-4-iodo-phenylamino)-isonicotinic acid methyl ester (300 mg, 0.64 mmol) in MeOH (3 mL) and stirred overnight at 60° C. The MeOH was removed and the aqueous solution was acidified with concentrated HCl. The resulting precipitate was filtered, washed with $H_2O$, and dried under vacuum to afford the desired product (215 mg, 74%). LC-MS (M+H=453, obsd.=453).

Intermediate 16

3-(2-Fluoro-phenyl)-5-(2-fluoro-4-iodo-phenylamino)-isonicotinic acid hydrazide

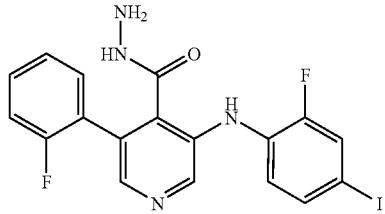

1,1'-carbonyldiimidazole (21 mg, 0.13 mmol) was added to a solution of 3-(2-fluoro-phenyl)-5-(2-fluoro-4-iodo-phenylamino)-isonicotinic acid (40 mg, 0.09 mmol) in DMSO (1 mL), and stirred overnight at 60° C. Hydrazine hydrate (13 mg, 0.27 mmol) was added, and the reaction solution was stirred for an additional 4 h at 60° C. The reaction solution was quenched with $H_2O$, diluted with EtOAc, and filtered through an Extrelut column. The column was washed with EtOAc, and the filtrate was concentrated. The crude product was purified via Biotage eluting with a gradient of 0 to 70% EtOAc in hexanes to afford the desired product (22 mg, 53%). LC-MS (M+H=467, obsd.=467).

Example 58

[4-(5-Amino-[1,3,4]oxadiazol-2-yl)-5-(2-fluoro-phenyl)-pyridin-3-yl]-(2-fluoro-4-iodo-phenyl)-amine

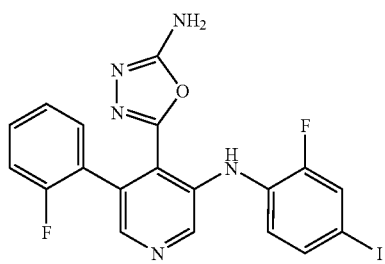

Phenyl cyanate (6 mg, 0.05 mmol) was added to a solution of 3-(2-fluoro-phenyl)-5-(2-fluoro-4-iodo-phenylamino)-isonicotinic acid hydrazide (22 mg, 0.05 mmol) in DMSO (1 mL), and stirred overnight at room temperature. The reaction solution was quenched with $H_2O$. The resulting precipitate was filtered, washed with $H_2O$, and dried under vacuum to afford the desired product (15 mg, 65%). LC-MS (M+H=492, obsd.=492). ¹H NMR: δ 8.78 (s, 1H), 8.43 (d, 1H), 8.11 (d, 1H), 7.73 (dd, 1H), 7.44 (m, 3H), 7.30 (m, 3H), 7.14 (s, 2H).

Intermediate 17

3-(2-Fluoro-4-iodo-phenylamino)-5-(2-fluoro-phenyl)-isonicotinamide

1,1'-carbonyldiimidazole (70 mg, 0.43 mmol) was added to a solution of 3-(2-fluoro-phenyl)-5-(2-fluoro-4-iodo-phenylamino)-isonicotinic acid (130 mg, 0.29 mmol) in DMSO (1 mL), and stirred overnight at 60° C. Ammonium acetate (89 mg, 1.15 mmol) was added, and the reaction solution was stirred for an additional 4 h at 60° C. The reaction solution was quenched with H₂O, diluted with EtOAc, and filtered through an Extrelut column. The column was washed with EtOAc, and the filtrate was concentrated. The crude product was purified via Biotage eluting with a gradient of 0 to 70% EtOAc in hexanes to afford the desired product (78 mg, 60%). LC-MS (M+H=452, obsd.=452).

Intermediate 18

3-(2-Fluoro-4-iodo-phenylamino)-5-(2-fluoro-phenyl)-isonicotinonitrile

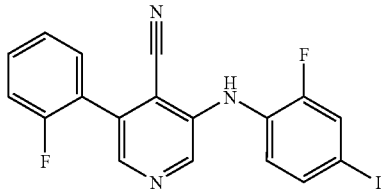

Pyridine (28 μL, 0.35 mmol) and trifluoroacetic anhydride (27 μL, 0.19 mmol) were added to a solution of 3-(2-fluoro-4-iodo-phenylamino)-5-(2-fluoro-phenyl)-isonicotinamide (78 mg, 0.17 mmol) in dioxane (2 mL) at 0° C. The resulting solution was stirred for 3 h at room temperature. The reaction was quenched with 2M NaOH and stirred for 10 minutes. The reaction solution was diluted with EtOAc and satd. NH₄Cl, and filtered through an Extrelut column. The column was washed with EtOAc, and the filtrate was concentrated to provide a precipitate. The precipitate was washed with MeOH and dried under vacuum to afford the desired product (60 mg, 80%). LC-MS (M+H=434, obsd.=434).

Example 59

(2-Fluoro-4-iodo-phenyl)-[5-(2-fluoro-phenyl)-4-(5-trimethylsilanyl-1H-[1,2,3]triazol-4-yl)-pyridin-3-yl]-amine

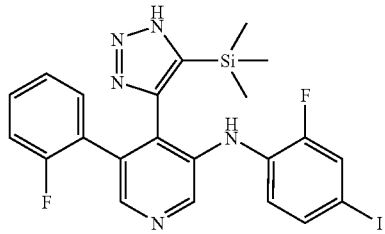

n-Butyllithium (28 μL, 2.5 M in THF, 0.07 mmol) was added to a solution of (trimethylsilyl)diazomethane (35 μL, 2.0 M in THF, 0.07 mmol) in THF (1 mL) at 0° C., and stirred for 20 minutes. 3-(2-Fluoro-4-iodo-phenylamino)-5-(2-fluoro-phenyl)-isonicotinonitrile (20 mg, 0.05 mmol) was added, and the resulting solution was stirred overnight at room temperature. The reaction solution was diluted with EtOAc and satd. NH₄Cl, and filtered through an Extrelut column. The column was washed with EtOAc, and the filtrate was concentrated. The crude product was purified via Biotage eluting with a gradient of 0 to 75% EtOAc in hexanes to afford the desired product (10 mg, 40%). LC-MS (M+H=548, obsd.=548).

Example 60

(2-Fluoro-4-iodo-phenyl)-[5-(2-fluoro-phenyl)-4-(1H-[1,2,3]triazol-4-yl)-pyridin-3-yl]-amine

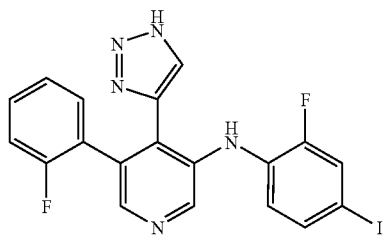

NaOH (50 μL, 2.0 M in H₂O, 0.09 mmol) was added to a solution of (2-fluoro-4-iodo-phenyl)-[5-(2-fluoro-phenyl)-4-(5-trimethylsilanyl-1H-[1,2,3]triazol-4-yl)-pyridin-3-yl]-amine (10 mg, 0.02 mmol) in MeOH (1 mL), and stirred overnight at 50° C. The reaction was quenched with satd. NH₄Cl, diluted with EtOAc, and filtered through an Extrelut column. The column was washed with EtOAc, and the filtrate was concentrated. The crude product was purified via Biotage eluting with a gradient of 0 to 75% EtOAc in hexanes to afford the desired product (6 mg, 69%) as a yellow solid. LC-MS (M+H=476, obsd.=476). ¹H NMR: δ 8.51 (s, 1H), 8.19 (s, 1H), 7.62 (dd, 1H), 7.44 (m, 1H), 7.38 (m, 2H), 7.28 (m, 2H), 7.19 (t, 1H), 6.99 (s, 1H).

Intermediate 19

2-fluoro-4-(trimethylsilyl)aniline

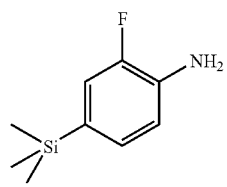

To a stirring solution of 2-fluoro-4-iodoaniline (5 g, 21.1 mmol) in dry ether (20 mL) at −78° C., Butyl lithium (2.5 M in Hexane, 25 mL) was added dropwise under nitrogen. The mixture was stirred at −78° C. for one hour. Liquid TMSCI (13.8 mL, 105.5 mmol) and DMAP was added into the mixture. The reaction was allowed to warm to amber temperature over 5 h. The reaction was then quenched with slow addition of Et₃N (4 mL) and MeOH (8 mL). The mixture was diluted with ether and washed with water, brine and dry with Na₂SO₄. The pure product was obtained by vacuum distillation (1-2 mmHg) at 100° C. (3.0 g, 78% yield). LC/MS [Method A: rt: 5.75 min; m/z: 184 (M+1)].

Intermediate 20

4-chloro-N-[2-fluoro-4-(trimethylsilyl)phenyl]pyridin-3-amine

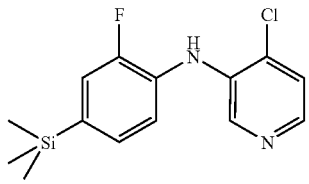

To a solution of 4-chloro-3-iodopyridine (1.37 g, 5.73 mmol) in dry toluene 25 mL, was added sequentially Pd(OAc)₂ (122.5 mg, 0.55 mmol), rac-BINAP (0.34 g, 0.55 mmol), Cs₂CO₃ (8.9 g, 27.3 mmol), and 2-fluoro-4-(trimethylsilyl)aniline (1 g, 5.45 mmol). The mixture was degassed with nitrogen twice. The mixture was then refluxed at 130° C. under nitrogen for 3 days. The mixture was filtered and the filtrate was diluted with EtOAc, washed with H₂O, brine, dried over anhydours Na₂SO₄. The organic phase was concentrated and the resulting residue was purified by flash column with 20% EtOAc-Hexane (0.3% Tab 3N in Hexane) to afford desired adduct (1.14 g, 70.1%). LC/MS [Method A: rt: 6.14 min; m/z: 295 (M+1)].

General Procedure for Suzuki Coupling:

(Ding, S.; Gray, N. S.; Wu, X.; Ding, Q.; Schultz, P. G. *J. Am. Chem. Soc.* 2002, 124, 1594-1596.)

Intermediate 21

(2-Fluoro-4-trimethylsilanyl-phenyl)-[4-(2H-pyrazol-3-yl)-pyridin-3-yl]-amine

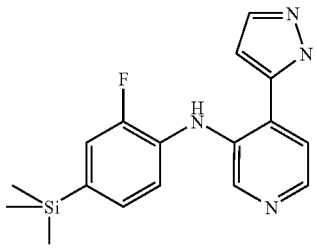

4-chloro-N-[2-fluoro-4-(trimethylsilyl)phenyl]pyridin-3-amine (70 mg, 0.24 mmol), (0.95 g, 6.8 mmol), Tris(dibenzylideneacetone)diPalladium(0) (21.7 mg, 0.02 mmol), 1,3-dimesityl-1H-imidazol-3-ium chloride (16.2 mg, 0.05 mmol) and cesium carbonate (2.76 g, 8.5 mmol) were dispended into a seal tube equipped with a stirring bar. The sealed tube was degassed by nitrogen before addition of anhydrous dioxane (14 mL). The mixture was heated at 130° C. over night. The mixture was then co-rotavapped with silica gel and applied to chromatography in silica gel. The desired product was obtained in pure form (63.2 mg, 63%). MS: m/z: 327 (M+1).

General Procedure for Iodination

Example 61

(2-Fluoro-4-iodo-phenyl)-[4-(2H-pyrazol-3-yl)-pyridin-3-yl]-amine

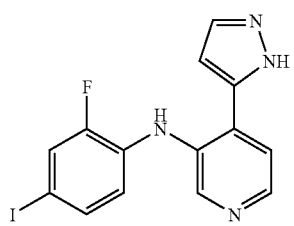

To a solution of (2-Fluoro-4-trimethylsilanyl-phenyl)-[4-(2H-pyrazol-3-yl)-pyridin-3-yl]-amine (45 mg, 0.14 mmol) in DCM (0.5 mL) was added ICl (2M, 0.21 mL, 0.41 mmol) dropwise. The mixture was stirred at RT overnight. The mixture was then diluted with DCM and washed with Na₂S₂O₃ (10%), water, brine and dried over Na₂SO₄. The organic phase was concentrated and the resulting residue was applied to chromatography in silica gel to afford product in 39% yield (52.4 mg). LC/MS [Method A: rt: 5.43 min; m/z: 381 (M+1)].

Intermediate 22

3-{[2-fluoro-4-(trimethylsilyl)phenyl]amino}isonicotinonitrile

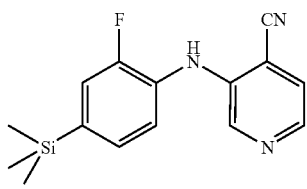

4-chloro-N-[2-fluoro-4-(trimethylsilyl)phenyl]pyridin-3-amine (122 mg, 0.41 mmol), Zn(CN)$_2$ (49 mg, 0.41 mmol) and Pd(Ph$_3$)$_4$ (48 mg, 0.04 mmol) were dispended into a seal tube equipped with a stirring bar. The seal tube was degassed by vacuum and recharging with nitrogen three times before addition of anhydrous DMF (2 mL). The mixture was heated at 130° C. for 12 h. (Alterman, M; Hallberg, A. *J. Org. Chem.* 2000, 65, 7984-7989) The mixture was diluted with EtOAc and washed with water and dried over solid Na$_2$SO$_4$. The organic phase was concentrated. The resulting residue was applied to chromatography in silica gel to give the desired product in 97% yield (118 mg). LC/MS [Method B: rt: 6.71 min; m/z: 286 (M+1)].

Intermediate 23

3-[(2-fluoro-4-iodophenyl)amino]isonicotinonitrile

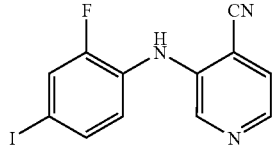

The title compound was prepared from 3-{[2-fluoro-4-(trimethylsilyl)phenyl]amino}isonicotinonitrile according the general procedure for iodination mentioned above. LC/MS [Method A: rt: 5.00 min; m/z: 340 (M+1)].

Example 62

N-(2-fluoro-4-iodophenyl)-4-(1H-tetrazol-5-yl)pyridin-3-amine

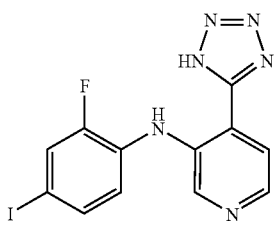

3-[(2-fluoro-4-iodophenyl)amino]isonicotinonitrile (100 mg, 0.29 mmol), ammonium chloride (28 mg, 0.52 mmol), and sodium azide (35 mg, 0.54 mmol) were dispended into a seal tube equipped with a stirring bar. The seal tube was degassed by vacuum and recharging with nitrogen three times before addition of anhydrous DMF (3 mL). The mixture was heated at 100° C. for three days. The mixture was diluted with saturated NaHCO$_3$ and washed with EtOAc. The aqueous phase was acidified with concentrated HCl to pH<1, and washed with EtOAc. The aqueous layer was dried to give the desired product. LC/MS [Method B: rt: 6.008 min; m/z: 383 (M+1)].

Example 63

N-(2-fluoro-4-iodophenyl)-4-[5-(trimethylsilyl)-1H-1,2,3-triazol-4-yl]pyridin-3-amine

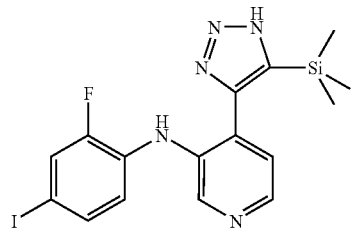

To a solution of TMSdiazomethane (2 M, 90 µL, 0.18 mmol) in ether (2 mL) at 0° C., was added butyl lithium (2.5 M, 72 µL, 0.18 mmol) dropwise. The mixture was stirred for 20 min at 0° C. 3-[(2-fluoro-4-iodophenyl)amino]isonicotinonitrile (50 mg, 0.15 mmol) was then added into the solution. The reaction was allowed to warm to room temperature and proceed for three days. The mixture was diluted with ether and washed with saturated ammonium chloride solution, water, and dried over solid Na$_2$SO$_4$. The organic phase was concentrated, and the resulting residue was applied to chromatography in silica gel to give the desired product in 40% yield (27 mg). LC/MS [Method A: rt: 0.40 min; m/z: 454 (M+1)].

Example 64

N-(2-fluoro-4-iodophenyl)-4-(1H-1,2,3-triazol-4-yl)pyridin-3-amine

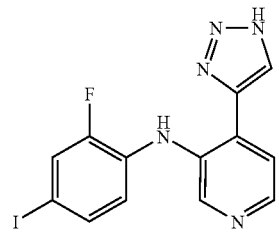

N-(2-fluoro-4-iodophenyl)-4-[5-(trimethylsilyl)-1H-1,2,3-triazol-4-yl]pyridin-3-amine (20 mg, 0.044 mmol) was added into a solution of NaOH (3.5 mg, 0.088 mmol) in THF (0.5 mL) for 5 days. The mixture was diluted with MeOH and neutralized to pH7 with acidic resin (Dowex). After filtration and the filtrate was concentrated to give pure product (11.5 mg, 69%). LC/MS [Method A: rt: 0.40 min; m/z: 381 (M+1)].

Intermediate 24

4-chloro-N-(2-fluoro-4-iodophenyl)pyridin-3-amine

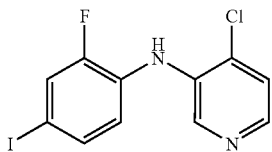

The title compound was prepared from 4-chloro-N-[2-fluoro-4-(trimethylsilyl)phenyl]pyridin-3-amine according the general procedure for iodination mentioned above. LC/MS [Method B: rt: 6.28 min; m/z: 349 (M+1)].

Example 65

(2-Fluoro-4-iodo-phenyl)-[4-(1H-pyrazol-4-yl)-pyridin-3-yl]-amine

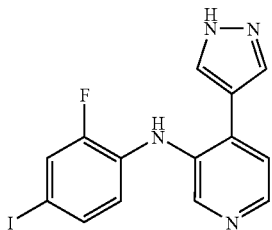

The title compound phenol was prepared from 4-chloro-N-[2-fluoro-4-(trimethylsilyl)phenyl]pyridin-3-amine according to the Suzuki Coupling conditions mentioned above. The resulting trimethylsilylated compound was then subjected to the iodination condition (see general procedure above) to afford the title compound. LC/MS [Method A: rt: 4.48 min; m/z: 381(M+1)].

Example 66

4-(3,5-Dimethyl-isoxazol-4-yl)-pyridin-3-yl]-(2-fluoro-4-iodo-phenyl)-amine

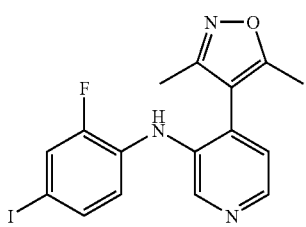

The title compound was prepared according the same procedure above. LC/MS [Method A: rt: 0.51 min; m/z: 410 (M+1)].

Functional Assays

Assay 1: MEK-1 Enzyme Assay (LANCE-HTRF)

Inhibition of human MEK1 kinase activity was monitored with a homogenous, fluorescence-based assay. The assay uses time resolved fluorescence resonance energy transfer to probe for phosphorylation of ERK1 by MEK1. The detailed procedure is described in the following:

Constititutively active MEK-1 EE (150 ng/well) and ERK-2K52A (110 ng/well) were incubated in black, 384 well Optiplates (Perkin Elmer) for 1.5 hrs at room temperature, in the presence of increasing concentrations of inhibitors. The total reaction volume was 50 ul. The inhibitors were serial diluted in kinase buffer (9 uM ATP, 50 mM Tris-Hcl pH 8.0, 10 mM MgCl2, 1 mM DTT and 100 uM Na3VO4), to a final concentration of 1% DMSO. At the end of the incubation, the enzyme reaction was quenched by adding 50 ul of assay buffer containing 50 mM Tris-Hcl, 50 mM EDTA, 0.1% BSA and a mixture of 1.25 ug/mL europium labeled anti-phosphotyrosine mAb (Perkin Elmer) and 5 ug/mL of allophycocyanin labeled anti-GST antibody (CIS-US). Plates were agitated on a plate shaker for 30 minutes and the phosphorylation of the ERK-2K52A substrate was measured by homogeneous time resolved fluorescence (HTRF) at 340 nm excitation and 665 nm (Europium)/615 nm (APC) emission filters on the VICTOR V fluorescence plate reader. Phosphorylation is expressed as a ratio of 665 nM signal×10,000/615 nM signal. To assess the inhibitory potential of the compounds, IC50-values were determined. Results are shown in Table 1, column 2, where "+++" indicates $IC_{50}$ values below or equal 3 μM, "++" indicates $IC_{50}$ values below or equal 25 μM and above 3 μM, and "+" indicates $IC_{50}$ values above 25 μM.

Assay 2: Tumor Cell Proliferation Assays (ATP Lite)

Murine colon C26 (1500 cells/well), human melanoma A375 (2000 cells/well), or human pancreatic MiaPaCa-2 cells (2000 cells/well) were plated in white, 96 well plates (Corning) in growth media (DMEM with 10% fetal bovine serum, 2 mM glutamine for C26 and MiaPaCa-2, and RPMI with 10% fetal bovine serum, 2 mM glutamine for A375) and cultured overnight at 37° C. in a humidified, 5% CO2 incubator. Inhibitors were serially diluted in 100% DMSO and subsequently added to the cells, in growth media, to reach a final concentration of 0.25% DMSO. The cells were incubated for 4 days in the presence of the test compounds and the proliferation was quantitated using the ATPlite cell proliferation kit (Packard). Results of the cell proliferation assay are shown in Table 1. columns 3-5, where "+++" indicates $IC_{50}$ values below or equal to 3 μM, "++" indicates $IC_{50}$ values below or equal to 25 μM and above 3 μM, and "+" indicates $IC_{50}$ values above 25 μM.

TABLE 1

Results of MEK enzyme assay and tumor cell proliferation assays

| Example | MEK1 | C26 | A375 | MiaPaCa2 |
|---|---|---|---|---|
| Example 1 | +++ | ++ | +++ | ++ |
| Example 2 | +++ | +++ | +++ | +++ |
| Example 3 | +++ | ++ | +++ | +++ |
| Example 4 | +++ | +++ | +++ | +++ |
| Example 5 | +++ | +++ | +++ | +++ |
| Example 6 | +++ | +++ | +++ | +++ |
| Example 7 | +++ | +++ | +++ | +++ |
| Example 8 | +++ | +++ | +++ | +++ |
| Example 9 | ++ | +++ | +++ | +++ |
| Example 10 | +++ | +++ | +++ | +++ |
| Example 11 | +++ | +++ | +++ | +++ |
| Example 12 | +++ | +++ | +++ | +++ |
| Example 13 | +++ | +++ | +++ | +++ |

TABLE 1-continued

Results of MEK enzyme assay and tumor cell proliferation assays

| Example | MEK1 | C26 | A375 | MiaPaCa2 |
|---|---|---|---|---|
| Example 14 | +++ | +++ | +++ | +++ |
| Example 15 | +++ | +++ | +++ | +++ |
| Example 16 | +++ | +++ | +++ | +++ |
| Example 17 | +++ | + | ++ | ++ |
| Example 18 | +++ | +++ | +++ | +++ |
| Example 19 | +++ | +++ | +++ | +++ |
| Example 20 | +++ | +++ | +++ | +++ |
| Example 21 | +++ | +++ | +++ | +++ |
| Example 22 | +++ | +++ | +++ | +++ |
| Example 23 | +++ | +++ | +++ | +++ |
| Example 24 | +++ | +++ | +++ | +++ |
| Example 25 | +++ | +++ | +++ | +++ |
| Example 26 | +++ | +++ | +++ | +++ |
| Example 27 | +++ | +++ | +++ | +++ |
| Example 28 | +++ | NT | NT | NT |
| Example 29 | +++ | +++ | +++ | +++ |
| Example 30 | +++ | NT | NT | NT |
| Example 31 | +++ | ++ | +++ | ++ |
| Example 32 | +++ | +++ | +++ | +++ |
| Example 33 | +++ | +++ | +++ | +++ |
| Example 34 | +++ | +++ | +++ | +++ |
| Example 35 | +++ | +++ | +++ | +++ |
| Example 36 | +++ | NT | NT | NT |
| Example 37 | +++ | +++ | +++ | +++ |
| Example 38 | +++ | +++ | +++ | ++ |
| Example 39 | +++ | + | +++ | + |
| Example 40 | +++ | +++ | +++ | +++ |
| Example 41 | +++ | +++ | +++ | +++ |
| Example 42 | +++ | +++ | +++ | +++ |
| Example 43 | +++ | +++ | +++ | ++ |
| Example 44 | +++ | +++ | +++ | +++ |
| Example 45 | +++ | ++ | +++ | ++ |
| Example 46 | +++ | +++ | +++ | +++ |
| Example 47 | +++ | +++ | +++ | +++ |
| Example 48 | +++ | +++ | +++ | +++ |
| Example 49 | +++ | +++ | +++ | +++ |
| Example 50 | +++ | +++ | +++ | +++ |
| Example 51 | +++ | ++ | +++ | ++ |
| Example 52 | +++ | +++ | +++ | +++ |
| Example 53 | +++ | +++ | +++ | ++ |
| Example 54 | +++ | +++ | +++ | +++ |
| Example 55 | +++ | +++ | +++ | +++ |
| Example 56 | +++ | + | ++ | ++ |
| Example 57 | +++ | +++ | +++ | +++ |
| Example 58 | +++ | +++ | +++ | +++ |
| Example 60 | +++ | +++ | +++ | +++ |
| Example 61 | +++ | ++ | +++ | +++ |
| Example 62 | +++ | + | + | + |
| Example 63 | +++ | +++ | +++ | +++ |
| Example 64 | +++ | +++ | +++ | +++ |
| Example 65 | +++ | +++ | +++ | +++ |
| Example 66 | +++ | NT | NT | NT |
| Example 67 | ++ | NT | NT | NT |
| Example 68 | +++ | NT | NT | NT |
| Example 69 | +++ | NT | NT | NT |
| Example 70 | + | + | ++ | + |

In vivo Efficacy Evaluation: Tumor Growth Inhibition in A375 Xenograft Studies
(Malignant Melanoma Model)

Male nude (nu/nu) mice (100 total, 24-26 g body wt) were purchased from Charles River Laboratories. Animals were injected subcutaneously above the right foreleg with $5\times10^6$ A375 cells in 100 ul of PBS. Tumors were measured with calipers 4, 7, 11 and 14 days after cells were implanted. Tumor length (l) and width (w) were measured and tumor volume was calculated with the equation $l*w^2/2$. At 16 days after cancer cells were implanted, tumors had reached an average volume of 93 mm$^3$, at which time the animals were sorted into 6 groups so that each group had the same mean tumor volume. The vehicle used for dosing the compound in suspension was 10% Tween 80 in water.

Treatments began on the afternoon of the 16th day after cancer cell injections, which was designated as Day 0. Tumor volume and body weight was measured for each animal 3 times per week until Day 14. On Day 14, all animals were euthanized, tumors removed and weighted.

The compound of Example 2 produced tumor regression at a dose of 10 mg/kg and significant tumor growth inhibition at a dose of 0.5 mg/kg.

The entire teachings of all references cited herein are hereby incorporated by reference.

The invention claimed is:

1. A compound of Formula (I),

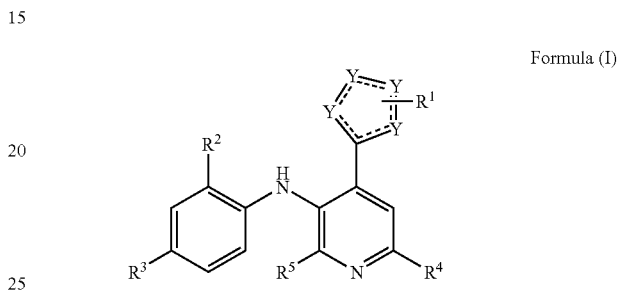

Formula (I)

as well as tautomers- and pharmaceutically acceptable salts thereof, wherein:
Y is independently selected from NR', CR', S or O, whereby at least one Y is NR';
$R^1$ is selected from hydrogen, trimethylsilyl, $C_1$-$C_6$-alkyl, $OR^6$, $C(O)OR^6$, $NR^7R^8$, $SR^6$, $NR^7S(O)(O)R'$, $NR^7C(O)R^6$, $NR^7C(O)NR^7R^6$, $NR^7C(O)OR^6$, $NR^7C(O)C(O)OR^6$, $C_1$-$C_4$-alkyl-NR'R", $C_1$-$C_4$-alkyl-heterocycloalkyl or $C_1$-$C_4$ alkyl-(OR')$_n$;
$R^2$ is halogen;
$R^3$ is selected from Cl, F or I;
$R^4$ and $R^5$ are independently selected from hydrogen, halogen, $C_1$-$C_6$ alkyl or $C_1$-$C_6$ alkoxy, wherein said alkyl or alkoxy is substituted or unsubstituted;
$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR', $C_1$-$C_4$-alkyl-NR'R", $C_1$-$C_4$-alkyl-heterocycloalkyl, $C_1$-$C_4$ alkyl-(OR')$_n$ or $C_1$-$C_4$ alkyl-C(O)NR'R", wherein said alkyl, cycloalkyl, aryl, heterocycloalkyl, and alkyl-heterocycloalkyl is substituted or unsubstituted; or
$R^7$ and $R^8$ can be taken together with the atom to which they are attached to form a 4 to 10-membered heteroaryl or heterocyclic ring, each of which is substituted or unsubstituted;
R' and R" are independently selected from hydrogen, $C_1$-$C_6$-alkyl or aryl, wherein said alkyl or aryl is substituted or unsubstituted; or
R' and R" can be taken together with the atom to which they are attached to form a 4 to 10-membered heteroaryl or heterocyclic ring, each of which is substituted or unsubstituted; and
n is 0 to 2.

2. The compound according to claim 1, wherein:
$R^1$ is selected from hydrogen, trimethylsilyl, $OR^6$, $NR^7R^8$, $NR^7C(O)R^6$, $NR^7C(O)OR^6$, or $C_1$-$C_4$ alkyl-(OR')$_n$;
$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR', $C_1$-$C_4$-alkyl-NR'R", $C_1$-$C_4$-alkyl-heterocycloalkyl, or $C_1$-$C_4$ alkyl-C(O)NR'R"; or R[7] and R[8] can be taken together with the atom to which they are attached to form a 6-membered heterocyclic ring with 1 or 2 N atoms and optionally an O atom; and R' and R" are either hydrogen or $C_1$-$C_6$-alkyl; or R' and R" can be taken together with the atom to which they are attached to form a 6-membered heterocyclic ring with 1 or 2 N atoms and optionally an O atom.

3. The compound according to claim 1 wherein:

$R^1$ is selected from hydrogen, $C_1$-$C_6$-alkyl, $OR^6$, $NR^7R^8$, $SR^6$, $NR^7S(O)(O)R'$, $NR^7C(O)R^6$, $NR^7C(O)NR^7R^6$, or $NR^7C(O)OR^6$;

$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR' or $C_1$-$C_4$ alkyl-C(O)NR'R", wherein said alkyl, cycloalkyl, aryl, heteroaryl and heterocyclyl substituted or unsubstituted; or $R^7$ and $R^8$ can be taken together with the atom to which they are attached to form a 4 to 10-membered heteroaryl or heterocyclic ring, each of which is substituted or unsubstituted; and R' and R" are independently selected from hydrogen, $C_1$-$C_6$-alkyl or aryl, wherein said alkyl or aryl is substituted or unsubstituted.

4. The compound according to claim 3, wherein:

$R^1$ is selected from $OR^6$, $NR^7R^8$ or $SR^6$;

$R^2$ is selected from F, Cl, I or Br;

$R^3$ is selected from F, Cl or I;

$R^4$ and $R^5$ are independently either hydrogen or $C_1$-$C_6$ alkyl;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR' or $C_1$-$C_4$ alkyl-C(O)NR'R", wherein said alkyl is substituted or unsubstituted; or $R^7$ and $R^8$ can be taken together with the atom to which they are attached to form a 6-membered heterocyclic ring with 1 or 2 N atoms and optionally an O atom, which is substituted or unsubstituted; and R' and R" are either hydrogen or $C_1$-$C_6$-alkyl.

5. The compound according to claim 4, wherein:

$R^2$ is F;

$R^3$ is I;

$R^4$ and $R^5$ are hydrogen;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR' or $C_1$-$C_4$ alkyl-C(O)NR'R", wherein said alkyl is substituted or unsubstituted; or $R^7$ and $R^8$ form a 6-membered heterocyclic ring with 1 or 2 N atoms and optionally an 0 atom, which is substituted or unsubstituted.

6. A compound of Formula (II),

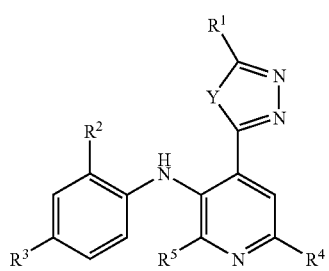

Formula (II)

as well as tautomers and pharmaceutically acceptable thereof, wherein:

Y is either NR' or O;

$R^1$ is selected from hydrogen, $C_1$-$C_6$-alkyl, $OR^6$, $NR^7R^8$, $SR^6$, $NR^7S(O)(O)R'$, $NR^7C(O)R^6$, $NR^7C(O)NR^7R^6$, or $NR^7C(O)OR^6$;

$R^2$ is halogen;

$R^3$ is selected from Cl, F or I;

$R^4$ and $R^5$ are independently selected from hydrogen, halogen, $C_1$-$C_6$ alkyl or $C_1$-$C_6$ alkoxy, wherein said alkyl or alkoxy is substituted or unsubstituted;

$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR' or $C_1$-$C_4$ alkyl-C(O)NR'R", wherein said alkyl, cycloalkyl, aryl, heteroaryl and heterocyclyl substituted or unsubstituted; or $R^7$ and $R^8$ can be taken together with the atom to which they are attached to form a 4 to 10-membered heteroaryl or heterocyclic ring, each of which is substituted or unsubstituted; and R' and R" are independently selected from hydrogen, $C_1$-$C_6$-alkyl or aryl, wherein said alkyl or aryl is substituted or unsubstituted.

7. A compound according to claim 6, wherein:

$R^1$ is selected from $OR^6$, $NR^7R^8$ or $SR^6$;

$R^2$ is selected from F, Cl, I or Br;

$R^3$ is selected from F, Cl or I;

$R^4$ and $R^5$ are independently either hydrogen or $C_1$-$C_6$ alkyl;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR' or $C_1$-$C_4$ alkyl-C(O)NR'R", wherein said alkyl is substituted or unsubstituted; or $R^7$ and $R^8$ can be taken together with the atom to which they are attached to form a 6-membered heterocyclic ring with 1 or 2 N atoms and optionally an O atom, which is substituted or unsubstituted; and R' and R" are either hydrogen or $C_1$-$C_6$-alkyl.

8. The compound according claim 7, wherein:

$R^2$ is F;

$R^3$ is I;

$R^4$ and $R^5$ are hydrogen;

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR' or $C_1$-$C_4$ alkyl-C(O)NR'R", wherein said alkyl is substituted or unsubstituted; or $R^7$ and $R^8$ form a 6-membered heterocyclic ring with 1 or 2 N atoms and optionally an 0 atom, which is substituted or unsubstituted.

9. A compound of Formula (IIa) or Formula (IIb),

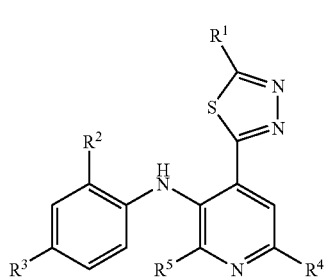

Formula (IIa)

-continued

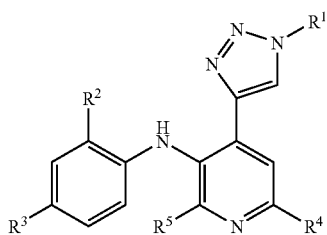

Formula (IIb)

as well as tautomers and pharmaceutically acceptable salts thereof, wherein:

R$^1$ is selected from hydrogen, trimethylsilyl, C$_1$-C$_6$-alkyl, OR$^6$, C(O)OR$^6$, NR$^7$R$^8$, SR$^6$, NR$^7$S(O)(O)R', NR$^7$C(O)R$^6$, NR$^7$C(O)NR$^7$R$^6$, NR$^7$C(O)OR$^6$, NR$^7$C(O)C(O)OR$^6$, C$_1$-C$_4$-alkyl-NR'R", C$_1$-C$_4$-alkyl-heterocycloalkyl or C$_1$-C$_4$ alkyl-(OR')$_n$;

R$^2$ is selected from halogen, C$_1$-C$_6$-alkyl or OR$^6$;

R$^3$ is halogen, trimethylsilyl, C$_1$-C$_6$-alkyl or OR$^6$;

R$^4$ and R$^5$ are independently selected from hydrogen, halogen, C$_1$-C$_6$ alkyl or C$_1$-C$_6$ alkoxy, wherein said alkyl or alkoxy is substituted or unsubstituted;

R$^6$, R$^7$ and R$^8$ are independently selected from hydrogen, C$_1$-C$_{10}$ alkyl, C$_3$-C$_{10}$ cycloalkyl, aryl, heteroaryl, heterocycloalkyl, C$_1$-C$_4$ alkyl-C(O)OR', C$_1$-C$_4$ alkyl-OR', C$_1$-C$_4$-alkyl-NR'R", C$_1$-C$_4$-alkyl-heterocycloalkyl, C$_1$-C$_4$ alkyl-(OR')$_n$ or C$_1$-C$_4$ alkyl-C(O)NR'R", wherein said alkyl, cycloalkyl, aryl, heteroaryl, heterocycloalkyl, and alkyl-heterocycloalkyl is substituted or unsubstituted; or R$^7$ and R$^8$ can be taken together with the atom to which they are attached to form a 4 to 10-membered heteroaryl or heterocyclic ring, each of which is substituted or unsubstituted;

R' and R" are independently selected from hydrogen, C$_1$-C$_6$-alkyl or aryl, wherein said alkyl or aryl is substituted or unsubstituted; or R' and R" can be taken together with the atom to which they are attached to form a 4 to 10 membered heteroaryl or heterocyclic ring, each of which is substituted or unsubstituted; and n is 0 to 2.

10. The compound according to claim 9, wherein:

R$^1$ is selected from hydrogen, trimethylsilyl, OR$^6$, NR$^7$R$^8$, NR$^7$C(O)R$^6$, NR$^7$C(O)OR$^6$, or C$_1$-C$_4$ alkyl-(OR')$_n$;

R$^2$ is selected from F or Cl;

R$^3$ is I;

R$^4$ and R$^5$ are hydrogen;

R$^6$, R$^7$ and R$^8$ are independently selected from hydrogen, C$_1$-C$_{10}$ alkyl, C$_1$-C$_4$ alkyl-C(O)OR', C$_1$-C$_4$ alkyl-OR', C$_1$-C$_4$-alkyl-NR'R", C$_1$-C$_4$-alkyl-heterocycloalkyl, or C$_1$-C$_4$ alkyl-C(O)NR'R", wherein said alkyl and alkyl-heterocycloalkyl is substituted or unsubstituted; or R$^7$ and R$^8$ can be taken together with the atom to which they are attached to form a 6-membered heterocyclic ring with 1 or 2 N atoms and optionally an O atom, which is substituted or unsubstituted; and R' and R" are either hydrogen or C$_1$-C$_6$-alkyl; or R' and R" can be taken together with the atom to which they are attached to form a 6-membered heterocyclic ring with 1 or 2 N atoms and optionally an O atom, which is substituted or unsubstituted.

11. A compound of Formula (III)

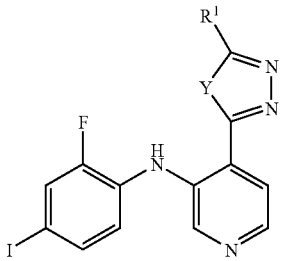

Formula (III)

as well as tautomers and pharmaceutically acceptable salts thereof, wherein:

Y is either O, or NR';

R$^1$ is selected from hydrogen, C$_1$-C$_6$-alkyl, OR$^6$, NR$^7$R$^8$ or SR$^6$ or NR$^7$S(O)(O)R';

R$^6$, R$^7$ and R$^8$ are independently selected from hydrogen, C$_1$-C$_{10}$ alkyl, C$_3$-C$_{10}$ cycloalkyl, aryl, heteroaryl, or heterocycloalkyl, C$_1$-C$_4$ alkyl-C(O)OR', C$_1$-C$_4$ alkyl-OR', C$_1$-C$_4$ alkyl-C(O)NR'R", wherein said alkyl, cycloalkyl, aryl, heteroaryl and heterocyclyl substituted or unsubstituted; or R$^7$ and R$^8$ can be taken together with the atom to which they are attached to form a 4 to 10 membered heteroaryl or heterocyclic ring, each of which is substituted or unsubstituted; and R' and R" are independently selected from hydrogen, C$_1$-C$_6$-alkyl or aryl, wherein said alkyl or aryl is substituted or unsubstituted.

12. A compound according to claim 11, wherein:

R$^1$ is selected from OR$^6$, NR$^7$R$^8$ or SR$^6$;

R$^6$, R$^7$ and R$^8$ are independently selected from hydrogen, C$_1$-C$_{10}$ alkyl, C$_1$-C$_4$ alkyl-C(O)OR', C$_1$-C$_4$ alkyl-OR' or C$_1$-C$_4$ alkyl-C(O)NR'R", wherein said alkyl is substituted or unsubstituted; or R$^7$ and R$^8$ can be taken together with the atom to which they are attached to form a 6 membered heterocyclic ring with 1 or 2 N atoms and optionally an O atom, which is substituted or unsubstituted; and R' and R" are independently either hydrogen or C$_1$-C$_6$-alkyl.

13. A compound of Formula (IIIa) or Formula (IIIb)

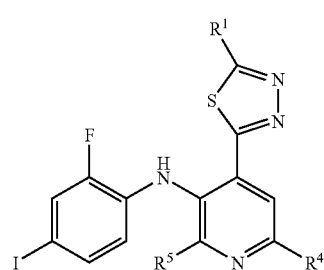

Formula (IIIa)

-continued

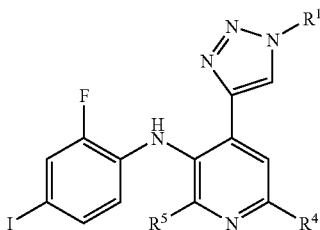

Formula (IIIb)

as well as tautomers and pharmaceutically acceptable salts thereof, wherein:
- $R^1$ is selected from hydrogen, trimethylsilyl, $C_1$-$C_6$-alkyl, $OR^6$, $C(O)OR^6$, $NR^7R^8$, $SR^6$, $NR^7S(O)(O)R'$, $NR^7C(O)R^6$, $NR^7C(O)NR^7R^6$, $NR^7C(O)OR^6$, $NR^7C(O)C(O)OR^6$, $C_1$-$C_4$-alkyl-$NR'R''$, $C_1$-$C_4$-alkyl-heterocycloalkyl or $C_1$-$C_4$ alkyl-$(OR')_n$;
- $R^4$ and $R^5$ are independently selected from hydrogen, halogen, $C_1$-$C_6$ alkyl or $C_1$-$C_6$ alkoxy, wherein said alkyl or alkoxy is substituted or unsubstituted;
- $R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-$C(O)OR'$, $C_1$-$C_4$ alkyl-$OR'$, $C_1$-$C_4$-alkyl-$NR'R''$, $C_1$-$C_4$-alkyl-heterocycloalkyl, $C_1$-$C_4$ alkyl-$(OR')_n$ or $C_1$-$C_4$ alkyl-$C(O)NR'R''$, wherein said alkyl, cycloalkyl, aryl, heteroaryl, heterocycloalkyl, and alkyl-heterocycloalkyl is substituted or unsubstituted; or
- $R^7$ and $R^8$ can be taken together with the atom to which they are attached to form a 4 to 10-membered heteroaryl or heterocyclic ring, each of which is substituted or unsubstituted;
- R' and R" are independently selected from hydrogen, $C_1$-$C_6$-alkyl or aryl, wherein said alkyl or aryl is substituted or unsubstituted; or
- R' and R" can be taken together with the atom to which they are attached to form a 4 to 10-membered heteroaryl or heterocyclic ring, each of which is substituted or unsubstituted; and
- n is 0 to 2.

14. The compound according to claim 13, wherein:
- $R^1$ is selected from hydrogen, trimethylsilyl, $OR^6$, $NR^7R^8$, $NR^7C(O)R^6$, $NR^7C(O)OR^6$, or $C_1$-$C_4$ alkyl-$(OR')_n$;
- $R^4$ and $R^5$ are hydrogen;
- $R^6$, $R^7$ and $R^8$ are independently selected from hydrogen, $C_1$-$C_{10}$ alkyl, $C_1$-$C_4$ alkyl-$C(O)OR'$, $C_1$-$C_4$ alkyl-$OR'$, $C_1$-$C_4$-alkyl-$NR'R''$, $C_1$-$C_4$-alkyl-heterocycloalkyl, or $C_1$-$C_4$ alkyl-$C(O)NR'R''$, wherein said alkyl and alkyl-heterocycloalkyl is substituted or unsubstituted; or
- $R^7$ and $R^8$ can be taken together with the atom to which they are attached to form a 6-membered heterocyclic ring with 1 or 2 N atoms and optionally an O atom, which is substituted or unsubstituted; and
- R' and R" are either hydrogen or $C_1$-$C_6$-alkyl; or
- R' and R" can be taken together with the atom to which they are attached to form a 6-membered heterocyclic ring with 1 or 2 N atoms and optionally an O atom, which is substituted or unsubstituted.

15. The compound according to claim 13, wherein:
- $R^1$ is selected from hydrogen, $C_1$-$C_6$-alkyl, $OR^6$, $NR^7R^8$ or $SR^6$ or $NR^7S(O)(O)R'$;
- $R^6$, $R^7$ and $R^8$ are independently selected from hydrogen, $C_1$-$C_{10}$ alkyl, $C_3$-$C_{10}$ cycloalkyl, aryl, heteroaryl, or heterocycloalkyl, $C_1$-$C_4$ alkyl-$C(O)OR'$, $C_1$-$C_4$ alkyl-$OR'$, $C_1$-$C_4$ alkyl-$C(O)NR'R''$, wherein said alkyl, cycloalkyl, aryl, heteroaryl and heterocyclyl substituted or unsubstituted; or
- $R^7$ and $R^8$ can be taken together with the atom to which they are attached to form a 4 to 10 membered heteroaryl or heterocyclic ring, each of which is substituted or unsubstituted; and
- R' and R" are independently selected from hydrogen, $C_1$-$C_6$-alkyl or aryl, wherein said alkyl or aryl is substituted or unsubstituted.

16. The compound according to claim 15, wherein:
- $R^1$ is selected from $OR^6$, $NR^7R^8$ or $SR^6$;
- $R^6$, $R^7$ and $R^8$ are independently selected from hydrogen, $C_1$-$C_{10}$ alkyl, $C_1$-$C_4$ alkyl-$C(O)OR'$, $C_1$-$C_4$ alkyl-$OR'$ or $C_1$-$C_4$ alkyl-$C(O)NR'R''$, wherein said alkyl is substituted or unsubstituted; or
- $R^7$ and $R^8$ can be taken together with the atom to which they are attached to form a 6 membered heterocyclic ring with 1 or 2 N atoms and optionally an O atom, which is substituted or unsubstituted; and
- R' and R" are independently either hydrogen or $C_1$-$C_6$-alkyl.

17. A compound of Formulae (IVa) or (IVb)

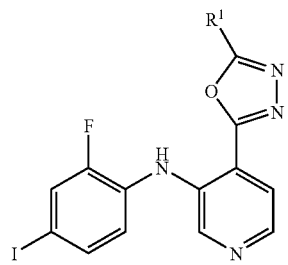

Formula (IVa)

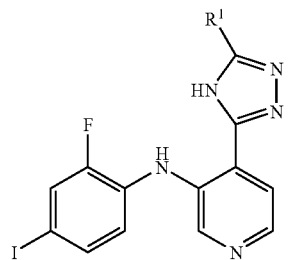

Formula (IVb)

as well as tautomers and pharmaceutically acceptable salts thereof, wherein:
- $R^1$ is selected from hydrogen, $C_1$-$C_6$-alkyl, $OR^6$, $NR^7R^8$ or $SR^6$ or $NR^7S(O)(O)R'$;
- $R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-$C(O)OR'$, $C_1$-$C_4$ alkyl-$OR'$ or $C_1$-$C_4$ alkyl-$C(O)NR'R''$, wherein said alkyl, cycloalkyl, aryl, heteroaryl and heterocyclyl substituted or unsubstituted; or
- $R^7$ and $R^8$ can be taken together with the atom to which they are attached to form a 4 to 10-membered heteroaryl or heterocyclic ring, each of which is substituted or unsubstituted; and
- R' and R" are independently selected from hydrogen, $C_1$-$C_6$-alkyl or aryl, wherein said alkyl or aryl is substituted or unsubstituted.

18. A compound according to claim 17, wherein:
$R^1$ is selected from $OR^6$, $NR^7R^8$ or $SR^6$;
$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR' or $C_1$-$C_4$ alkyl-C(O)NR'R", wherein said alkyl is substituted or unsubstituted; or
$R^7$ and $R^8$ can be taken together with the atom to which they are attached to form a 6-membered heterocyclic ring with 1 or 2 N atoms and optionally an O atom, which is substituted or unsubstituted; and
R' and R" are independently either hydrogen or $C_1$-$C_6$-alkyl.

19. A compound of Formulae (IVa) or (IVb)

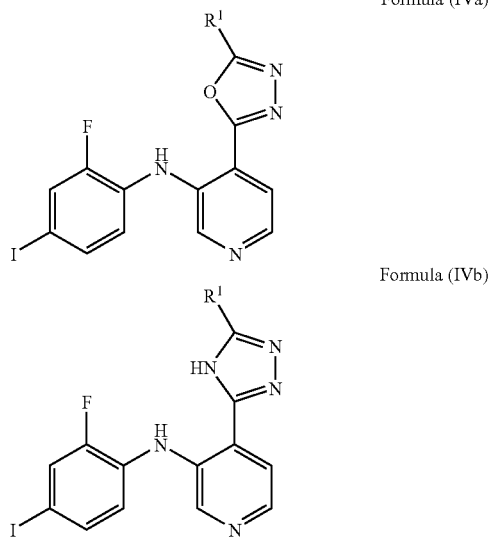

Formula (IVa)

Formula (IVb)

as well as tautomers and pharmaceutically acceptable salts thereof, wherein:
$R^1$ is selected from hydrogen, trimethylsilyl, $C_1$-$C_6$-alkyl, $OR^6$, $C(O)OR^6$, $NR^7R^8$, $SR^6$, $NR^7S(O)(O)R'$, $NR^7C(O)R^6$, $NR^7C(O)NR^7R^6$, $NR^7C(O)OR^6$, $NR^7C(O)C(O)OR^6$, $C_1$-$C_4$-alkyl-NR'R", $C_1$-$C_4$-alkyl-heterocycloalkyl or $C_1$-$C_4$ alkyl-(OR')$_n$;
$R^6$, $R^7$ and $R^8$ are independently selected from hydrogen, $C_1$-$C_{10}$ alkyl, $C_3$-$C_{10}$ cycloalkyl, aryl, heteroaryl, heterocycloalkyl, $C_1$-$C_4$ alkyl-C(O)OR', $C_1$-$C_4$ alkyl-OR', $C_1$-$C_4$-alkyl-NR'R", $C_1$-$C_4$-alkyl-heterocycloalkyl, $C_1$-$C_4$ alkyl-(OR')$_n$ or $C_1$-$C_4$ alkyl-C(O)NR'R", wherein said alkyl, cycloalkyl, aryl, heteroaryl, heterocycloalkyl, and alkyl-heterocycloalkyl is substituted or unsubstituted; or
$R^7$ and $R^8$ can be taken together with the atom to which they are attached to form a 4 to 10-membered heteroaryl or heterocyclic ring, each of which is substituted or unsubstituted;
R' and R" are independently selected from hydrogen, $C_1$-$C_6$-alkyl or aryl, wherein said alkyl or aryl is substituted or unsubstituted; or
R' and R" can be taken together with the atom to which they are attached to form a 4 to 10-membered heteroaryl or heterocyclic ring, each of which is substituted or unsubstituted; and
n is 0 to 2.

20. The compound according to claim 19, wherein:
$R^1$ is selected from hydrogen, trimethylsilyl, $OR^6$, $NR^7R^8$, $NR^7C(O)R^6$, $NR^7C(O)OR^6$, or $C_1$-$C_4$ alkyl-(OR')$_n$;
$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR', $C_1$-$C_4$-alkyl-NR'R", $C_1$-$C_4$-alkyl-heterocycloalkyl, or $C_1$-$C_4$ alkyl-C(O)NR'R", wherein said alkyl and alkyl-heterocycloalkyl is substituted or unsubstituted; or
$R^7$ and $R^8$ can be taken together with the atom to which they are attached to form a 6-membered heterocyclic ring with 1 or 2 N atoms and optionally an O atom, which is substituted or unsubstituted; and
R' and R" are either hydrogen or $C_1$-$C_6$-alkyl; or
R' and R" can be taken together with the atom to which they are attached to form a 6-membered heterocyclic ring with 1 or 2 N atoms and optionally an O atom, which is substituted or unsubstituted.

21. A pharmaceutical composition, which comprises a compound of claim 1 and a pharmaceutically acceptable carrier.

* * * * *